(12) United States Patent
Ohtake et al.

(10) Patent No.: US 6,225,306 B1
(45) Date of Patent: May 1, 2001

(54) BIPHENYL DERIVATIVES AND DRUG COMPOSITION

(75) Inventors: Yasuhiro Ohtake; Akira Naito; Kenji Naito; Hidehiko Matsukawa; Yoshiaki Saito; Hatsunori Toyofuku, all of Tokyo (JP)

(73) Assignee: Wakamoto Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/409,349

(22) Filed: Sep. 30, 1999

Related U.S. Application Data

(63) Continuation of application No. PCT/JP97/04333, filed on Nov. 27, 1997.

(30) Foreign Application Priority Data

Mar. 31, 1997 (JP) .................................................. 9-094460

(51) Int. Cl.[7] .......................... A61K 31/55; A61K 31/535; A61K 31/495; C07D 245/00; C07D 267/22
(52) U.S. Cl. ..................... 514/211.08; 514/220; 514/234; 514/250; 514/411; 540/460; 540/469; 540/479; 540/496; 540/545; 540/561
(58) Field of Search ............................ 544/234; 514/250, 514/211.08, 220, 411; 540/460, 469, 479, 496, 545, 561

(56) References Cited

U.S. PATENT DOCUMENTS

| | | | |
|---|---|---|---|
| 5,521,173 | 5/1996 | Venkatesan et al. | 514/220 |
| 5,536,718 | 7/1996 | Albright et al. | 514/220 |
| 5,700,796 | 12/1997 | Albright et al. | 514/220 |

FOREIGN PATENT DOCUMENTS

WO 97/49707   12/1997  (WO) .

OTHER PUBLICATIONS

Patent Abstracts of Japan, vol. 1996, No. 07, Jul. 31, 1996, JP 08 081460, Mar. 26, 1996.
Patent Abstracts of Japan, vol. 018, No. 482, Sep. 8, 1994, JP 06 157480, Jun. 3, 1994.
H. Ogawa, et al., j. Med. Chem., vol. 39, No. 18, pp. 3547 3555, "Orally Active, Nonpeptide Vasopressin $V_2$ Receptor Antagonists. A Novel Series of 1–[4–(Benzoylamino) Benzoyl]–2,3,4,5–Tetrahydro–1H–Benzazepines and Related Compounds", 1996.
A. Matsuhisa, et al., Chem. Pharm, Bull., vol. 45, No. 11, pp. 1870 1874, "Nonpeptide Arginine Vasopressin Antagonists for Both $V_{1A}$ and $V_2$ Receptors: Synthesis and Pharmacological Properties of 2–Phenyl–4'—[(2,3,4, 5–Tetrahydro–1H–1–Benzazepin–1–YL)Carbonyl] Benzanilide Derivatives", 1997.

*Primary Examiner*—Bruck Kifle
(74) *Attorney, Agent, or Firm*—Oblon, Spivak, McClelland, Maier & Neustadt, P.C.

(57) ABSTRACT

A biphenyl derivative represented by the following general formula (1) and a pharmaceutically acceptable salt thereof:

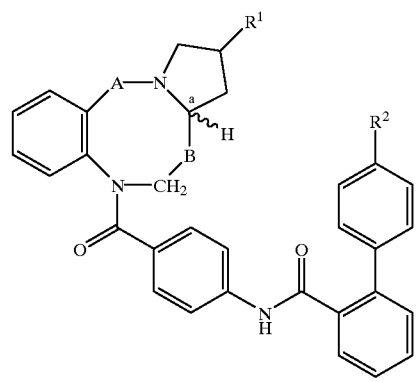

[In the formula (1), A represents a single bond, —$CH_2$—, —CO—, —CS— or —$SO_2$—; B represents a single bond or —$CH_2$—; $R^1$ represents a hydrogen atom, —OH, —$NR^{11}R^{12}$ (wherein $R^{11}$ and $R^{12}$ each independently represents a hydrogen atom or an alkyl group having 1 to 4 carbon atoms), —$OCOCH_3$, or a halogen atom; $R^2$ represents a hydrogen atom or $R^1$ and $R^2$ form a group =O together; $R^3$ represents a hydrogen atom or an alkyl group having 1 to 4 carbon atoms; provided that in the formula, the absolute configuration of the position a may be either R or S]. The compound of the present invention has considerably high safety and efficacy and is useful as, in particular, a vasopressin receptor antagonist.

9 Claims, 5 Drawing Sheets

RELATION BETWEEN THE URINE VOLUME AND THE URINARY SODIUM EXCRETION

RELATION BETWEEN THE URINE VOLUME AND THE URINARY POTASSIUM EXCRETION

RELATION BETWEEN THE URINE VOLUME AND THE URINARY CHLORINE EXCRETION

RELATION BETWEEN THE URINE VOLUME AND THE URINARY OSMOLALITY

BIPHENYL DERIVATIVES AND DRUG COMPOSITION

This application is a Continuation of International Application Ser. No. PCT/JP97/04333, filed on Nov. 27, 1997.

TECHNICAL FIELD

The present invention relates to a biphenyl derivative and pharmaceutically acceptable salts thereof as well as a drug composition comprising the same. More particularly, the present invention relates to a biphenyl derivative comprising a biphenyl group that carries a carbonylphenyl-carbamoyl group, which is further bonded to a tricyclic hetero ring and pharmaceutically acceptable salts thereof as well as a drug composition containing the same, in particular, a drug composition serving as a vasopressin receptor antagonist.

BACKGROUND ART

Vasopressin is a neuroendocrine hormone secreted from the posthypophysis and, in the periphery, plays a role of maintaining the circulatory kinetics and the body fluid homeostasis mainly by the strong vasoconstricting effect through the V1 receptor and the water resorption-promoting effect in the renal collecting tubule through the V2 receptor. In addition, vasopressin possesses various physiological effects such as an effect of promoting glycogenolysis in liver, an effect of promoting the adrenocoiticotropic hormone (ACTH)-secretion from the prehypophysis or an effect of promoting the platelet agglutination.

The excess secretion of vasopressin having such effects causes various pathemas such as conjestive heart failure Pharmacological Reviews, 1991, 43:73–108), brain edema (Stroke, 1992, 23:1767–1773), arginine-vasopressin polyrrhea syndrome (Journal of Cardiovascular Pharmacology, 1986, 8:S36–S43), hepatociurhosis (Ann. Intermn Med., 1982, 96:413–417) and hypertension. Therefore, if an excellent vasopressin antagonist is developed, such antagonist may be useful as a remedy and/or a prophylactic for these diseases caused due to the excess secretion of vasopressin, for instance, heart failure, edema such as brain edema, hydroperitoneum, pneumochysis, arginine-vasopressin polyrrhea syndrome, renal failure, pancreatitis, hypertension, hepatocirrhosis, hyponatremia, hypokalemia, diabetes, circulatory disorders, Meniere's syndrome and oxytocin-related diseases; and diuretics (IGAKU NO AYUMI, 1991, 157:166). Up to now, there have been developed a variety of vasopressin-receptor antagonists for the purpose of preventing or treating vasopressin-related diseases.

In particular, the non-peptide type compound can orally be administered unlike the peptide type one. Therefore, the former would be expected to have clinical usefulness and there have been proposed various such compounds in, for instance, Japanese Un-examined Patent Publication (hereunder referred to as "J.P. KOKAI") Nos. Hei 7-2800, Hei 4-321669, Hei 4-154765, Hei 6-172317, Hei 5-132466, Hei 5-320135, Hei 6-157480, Hei 6-211800, Hei 6-16643, Hei 7-157486 and Hei 7-179430; and Published International Patent Application (hereunder referred to as "P.I.A.") Nos. WO95/03305, WO94/12476, WO94/14796 and WO94/20473. Such technical background has been disclosed in P.I.A. No. WO97/17349.

Moreover, edema is a pathema in which the extracellular fluid is excessively accumulated in external parts of blood vessels. The causes for the crisis thereof can roughly be divided into two groups, i.e., the insufficient excretion of the extracellular fluid in the exterior of the blood vessel and the excess exudation of the extracellular fluid from blood vessels. Large amounts of the fluid in the thoracic cavity or ascites would impair systemic hemodynamics (circulatory kinetics), for instance, decreases in cardiac output, the flow rate of blood in liver, and the flow rate of blood in kidney. In addition, the disease often makes it difficult for the patients suffering from the same, to take a diet due to respiratory difficulty and/or abdominal inflation. There have thus been used diuretics for relieving and treating edema.

The so-called loop diuretics presently widely used such as Furosemide (Lasix (registered trademark)) are electrolyte-discharge type diuretics which can inhibit the resorption of water and electrolytes in the renal tubules. However, such electrolyte-discharge type diuretics suffer from a problem in that they would essentially break the electrolyte balance in the living body (Aifred Goodman Gilman et al., Goodman and Gilman's The Pharmacological Basis of Therapeutics, $8^{th}$ edition, pp.721–731, 1990) and therefore, there has recently been tried to develop so-called aquaresis which permit the selective excretion of only water.

The drugs possessing vasopressin receptor antagonism have attracted special interest recently, as drugs having aquaresis (Yamamura Yoshitaka et al., Br. J. Pharmacol., 1992, 105:787). In particular, there have been conducted various studies to develop vasopressin V2 receptor antagonists.

J.P. KOKAI No. Hei 7-2800 discloses certain benzamide derivatives, which possess vasopressin-receptor antagonism and are thus useful as medicines, in particular, vasodilators, aquaresis or the like. In these compounds, however, the hetero ring bonded to the carbonylphenyl carbamoyl group is not a tricyclic hetero ring.

P.I.A- No. WO95/03305 discloses that a fused benzazepine derivative characterized in that it has a chemical structure carrying a tricyclic heterocyclic benzazepine has vasopressin receptor antagonism and is effective as a medicine. This compound is recognized to have stronger and longer-lasting vasopressin V2 receptor antagonism as compared with OPC-31260 (P.I.A. No. WO91/05549) which is a vasopressin receptor antagonist presently in course of development. The compound has a chemical structure carrying a carbonylphenyl carbamoyl group, but the tricyclic hetero ring linked thereto is a benzazepine.

J.P. KOKAI No. 7-157486 discloses that a compound having a tricyclic diazepin ring possesses vasopressin receptor antagonism. However, this compound never has a biphenyl group.

Thus, the development of medicines possessing aquaresis has been made progress. Edema does not appear until pathema such as cancers from which many patients suffer, congestive heart failure, nephrotic syndromes and hepato-cirrhosis are advanced to some extent. Since the patients suffering therefrom feel severe pains, there have intensively been desired for the development of novel compounds which have almost no side effect, highly efficient aquaresis, in particular, vasopressin receptor antagonism and are very useful, among clinicians.

SUMMARY OF THE INVENTION

Under such circumstances, it is an object of the present invention to provide a drug composition, in particular, compounds useful as vasopressin receptor antagonists, which are completely different in the structure and effects from the diuretics presently employed, which have structure quite different from those of the compounds recently discovered and having vasopressin receptor antagonism, and which are highly efficient and have very high safety and efficiency.

The inventors of this invention have conducted various studies, have found that the compounds represented by the following general formula (1) permit the achievement of the foregoing object of the present invention and thus have completed the present invention. More specifically, the compounds of the present invention are biphenyl derivatives represented by the following general formula (1) and pharmaceutically acceptable salts thereof:

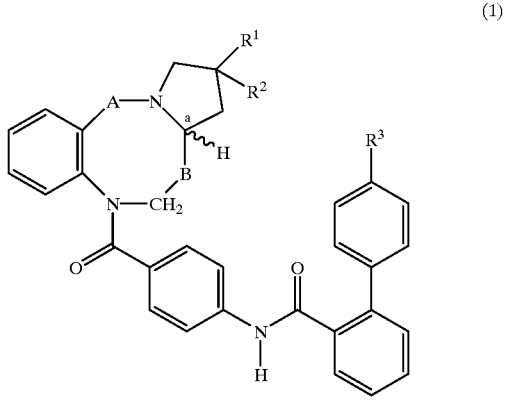

[in the formula, A represents a single bond, —CH$_2$—, —CO—, —CS— or —SO$_2$—; B represents a single bond or a group —CH$_2$—; R$^1$ represents a hydrogen atom, —OH, —NR$^{11}$R$^{12}$ (wherein R$^{11}$ and R$^{12}$ each independently represents a hydrogen atom or an alkyl group having 1 to 4 carbon atoms), —OCOCH$_3$, or a halogen atom; R$^2$ represents a hydrogen atom or R$^1$ and R$^2$ represent =O, in combination; R$^3$ represents a hydrogen atom or an alkyl group having 1 to 4 carbon atoms; provided that the absolute configuration at the position a may be either S or R.]

BEST MODE FOR CARRYING OUT THE INVENTION

Figure 1:
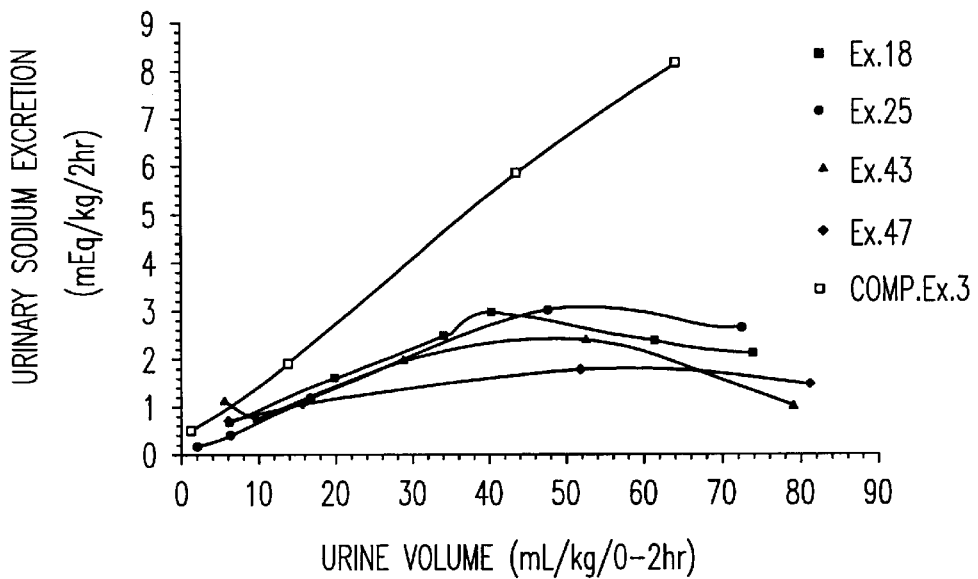
FIG. 1 shows the relations between the urine volume and the urinary sodium excretion.

The present invention will hereunder be described in more detail.

The compound of the present invention represented by the foregoing general formula (1) has various characteristic properties concerning the chemical structure such as those listed below:

1. The compound has a terminal substituted or unsubstituted biphenyl group;
2. The biphenyl group is substituted with a carbonylphenyl carbamoyl group;
3. The carbonylphenyl carbamoyl group is linked to a tricyclic hetero ring having a specific structure.

If the substituent R$^1$ is an NR$^{11}$R$^{12}$ group, R$^{11}$ and R$^{12}$ each independently represents a hydrogen atom or an alkyl group having 1 to 4 carbon atoms. The group NR$^{11}$R$^{12}$ may be an amino group or a mono- or di-alkylamino group whose carbon atom number ranges from 1 to 4. The alkyl group is not restricted to any specific one, so far as it has a carbon atom number ranging from 1 to 4 and specific examples thereof include methyl, ethyl, propyl and butyl groups, which may be linear or branched ones, with a methyl group being particularly preferred.

If the substituent R$^1$ is a halogen atom, it is not restricted to an, specific one and specific examples thereof are chlorine, bromine, fluorine and iodine, with a fluorine atom being particularly preferred.

If the substituent R$^1$ is —OH, —NR$^{11}$R$^{12}$, —OCOCH$_3$, or a halogen atom, the absolute configuration of the carbon atom to which the substituent R$^1$ is bonded may be R, S or mixture thereof.

In the compound of the present invention, R$^3$ represents a hydrogen atom or an alkyl group having 1 to 4 carbon atoms. Specific examples thereof include methyl, ethyl, propyl and butyl groups, which may be linear or branched ones, with a methyl group being particularly preferred.

In the compound of the present invention, the absolute configuration of the carbon atom through which the group B is linked with the pyrrolidine ring may be R, S or mixture thereof.

The salts of the compounds according to the present invention may be acid addition salts with inorganic or organic acids, with pharmaceutically acceptable salts thereof being preferred. Specific examples of these salts include acid addition salts with, for instance, mineral acids such as hydrochloric acid, hydrobromic acid, hydriodic acid, sulfuric acid, nitric acid or phosphoric acid; organic acids such as formic acid, acetic acid, propionic acid, oxalic acid, malonic acid, succinic acid, fumaric acid, maleic acid, lactic acid, malic acid, tartalic acid, citric acid, benzoic acid, p-toluenesulfonic acid, isethionic acid, glucuronic acid, gluconic acid, methanesulfonic acid or ethanesulfonic acid; or acidic amino acids such as aspartic acid or glutamic acid.

Specific examples of the compounds according to the present invention include those listed below:
(1) (3aR)-5-[4-[(2-phenylbenzoyl)amino]benzoyl]-1,2,3,3a,4,5-hexahydro-pyrrolo[1,2-a]quinoxaline
(2) (3aR)-5-[4-[[2-(4-tolyl)benzoyl]amino]benzoyl]-1,2,3,3a,4,5-hexahydro-pyrrolo[1,2-a]quinoxaline
(3) (3aR)-5-[4-[[2-(4-cumenyl)benzoyl]amino]benzoyl]-1,2,3,3a,4,5-hexahydropyrrolo[1,2-a]quinoxaline
(4) (3aS)-5-[4-[(2-phenylbenzoyl)amino]benzoyl]-1,2,3,3a,4,5-hexahydro-pyrrolo[1,2-a]quinoxaline
(5) (3aS)-5-[4-[[2-(4-tolyl)benzoyl]amino]benzoyl]-1,2,3,3a,4,5-hexahydropyrrolo[1,2-a]quinoxaline
(6) (3aS)-5-[4-[[2-(4-cumenyl)benzoyl]amino]benzoyl]-1,2,3,3a,4,5-hexahydropyrrolo[1,2-a]quinoxaline
(7) (2R,3aR)-2-hydroxy-5-[4-[(2-phenylbenzoyl)amino]benzoyl]-1,2,3,3a,4,5-hexahydropyrrolo[1,2-a]quinoxaline
(8) (2R,3aS)-2-hydroxy-5-[4-[2-phenylbenzoyl)amino]benzoyl]-1,2,3,3a,4,5-hexahydropyrrolo[1,2-a]quinoxaline
(9) (2R,3aR)-2-hydroxy-5-[4-[[2-(4-tolyl)benzoyl]amino]benzoyl]-1,2,3,3a,4,5-hexahydropyrolo[1,2-a]quinoxaline

(10) (2R,3aS)-2-hydroxy-5-[4-[[2-(4-tolyl)benzoyl]amino]benzoyl]-1,2,3,3a,4,5-hexahydlopyrolo[1,2-a]quinoxahine

(11) (2S, 3aR)-2-hydroxy-5-[4-[(2-phenylbenzoyl)amino]benzoyl]-1,2,3,3a,4,5-hexahydropyrrolo[1,2-a]quinoxaline

(12) (2S, 3aS)-2-hydroxy-5-[4-[(2-phenylbenzoyl)amino]benzoyl]-1,2,3,3a,4,5-hexahydropyrolo[1,2-a]quinoxaline

(13) (2S, 3aR)-2-hydroxy-5-[4-[[2-(4-tolyl)benzoyl]amino]benzoyl]-1,2,3,3a,4,5-hexahydropyrrolo[1,2-a]quinoxaline

(14) (2S, 3aS)-2-hydroxy-5-[4-[[2-(4-tolyl)benzoyl]amino]benzoyl-1,2,3,3a,4,5-hexahydropyrrolo[1,2-a]quinoxaline

(15) (2S, 3aR)-2-acetoxy-5-[4-[(2-phenylbenzoyl)amino]benzoyl]-1,2,3,3a,4,5-hexahydiopyrolo[1,2-a]quinoxaline

(16) (2S, 3aS)-2-acetoxy-5-[4-[(2-phenylbenzoyl)amino]benzoyl]-1,2,3,3a, 4,5-hexahydropyrrolo[1,2-a]quinoxaline

(17) (2S, 3aR)-2-acetoxy-5-[4-[[2-(4-tolyl)benzoyl]amino]benzoyl]-1,2,3,3a,4,5-hexahydropyrrolo 1,2-a]quinoxaline

(18) (2S, 3aS)-2-acetoxy-5-[4-[[2-(4-tolyl)benzoyl]amino]benzoyl]- 1,2,3,3a,4,5-hexahydropyrrolo[1,2-a]quinoxaline

(19) (2S, 3aR)-2-amono-5-[4-[(2-phenylbenzoyl)amino]benzoyl]-1,2,3,3a,4,5-hexahydropyrrolo[1,2-a]quinoxaline and hydrochloric acid salt thereof

(20) (2S, 3aS)-2-amino-5-[4-[(2-phenylbenzoyl)amino]benzoyl]-1,2,3,3a,4,5-hexahydropyrrolo[1,2-a]quinoxaline and hydrochloric acid salt thereof

(21) (2S, 3aR)-2-amino-5-[4-[[2-(4-tolyl)benzoyl]amino]benzoyl]-1,2,3,3a,4,5-hexahydropyrrolo[1,2-a]quinoxaline and hydrochloric acid salt thereof

(22) (2S, 3aS)-2-amino-5-[4-[[2-(4-tolyl)benzoyl]amino]benzoyl]-1,2,3,3a,4,5-hexahydropyrrolo[1,2-a]quinoxaline and hydrochloric acid salt thereof

(23) (2S, 3aR)-2-(N-ethylamino)-5-[4-[(2-phenylbenzoyl)amino]benzoyl]-1,2,3,3a,4,5-hexahydropyrrolo[1,2-a]quinoxaline and hydrpbromic acid salt thereof

(24) (2S, 3aS)-2-(N-ethylamino)-5-[4-[(2-phenylbenzoyl)amino]benzoyl]-1,2,3,3a,4,5-hexahydropyrrolo[1,2-a]quinoxaline and hydipbromic acid salt e thereof

(25) (2S, 3aR)-2-(N-ethylamino)-5-[4-[[2-(4-tolyl)benzoyl]amino]benzoyl]-1,2,3,3a,4,5-hexahydropyrrolo[1,2-a]quinoxaline and hydrochloric acid salt thereof

(26) (2S, 3aS)-2-(N-ethylamino)-5-[4-[[2-(4-tolyl)benzoyl]amino]benzoy-1,2,3,3a,4,5-hexahydropyrrolo[1,2-a]quinoxaline and hydrochloric acid salt thereof

(27) (2S, 3aR)-2-[N-(1-methylethyl)amino]-5-[4-[[2-(4-cumenyl)benzoyl]amino]benzoyl]-1,2,3,3a,4,5-hexahydropyrrolo[1,2-a]quinoxaline and acetic acid salt thereof

(28) (2S, 3aS)-2-[N-(1-methylethyl)amino]-5-(4-[[2-(4-cumenyl)benzoyl]amino]benzoyl]-1,2,3,3a,4,5-hexahydropyrrolo[1,2-a]quinoxaline and acetic acid salt thereof

(29) (2S, 3aR)-2-(N,N-dimethylamino)-5-[4-[(2-phenylbenzoyl)amino]benzoyl)-1,2,3,3a,4,5-hexahydropyrrolo[1,2-a]quinoxaline and hydrochloric acid salt thereof

(30) (2S, 3aS)-2-(N,N-dimethylamino)-5-[4-[(2-phenylbenzoyl)amino]benzoyl]-1,2,3,3a,4,5-hexahydropyrrolo[1,2-a]quinoxaline and hydrochloric acid salt thereof

(31) (2S, 3aR)-2-(N,N-dimethylamino)-5-[4-[[2-(4-tolyl)benzoyl]amino]benzoyl]-1,2,3,3a,4,5-hexahydropyrrolo[1,2-a]quinoxaline and hydrochloric acid salt thereof

(32) (2S, 3aS)-2-(N,N-dimethylamino)-5-[4-[[2-(4-tolyl)benzoyl]amino]benzoyl]-1,2,3,3a,4,5-hexahydropyrrolo[1,2-a]quinoxahine and hydrochloric acid salt thereof

(33) (2S, 3aR)-2-fluoro-5-[4-[(2-phenylbenzoyl)amino]benzoyl]-1,2,3,3a,4,5-hexahydropyrrolo[1,2-a]quinoxahine

(34) (2S, 3aS)-2-fluoro-5-[4-[(2-phenylbenzoyl)amino]benzoyl]-1,2,3,3a, 4,5-hexahydropyrrolo[1,2-a]quinoxaline

(35) (2S, 3aR)-2-fluoro-5-[4-[[2-(4-tolyl)benzoyl]amino]benzoyl]-1,2,3,3a,4,5-hexahydropyrrolo[1,2-a]quinoxaline

(36) (2S, 3aS)-2-fluoro-5-[4-[[2-(4-tolyl)benzoyl]amino]benzoyl]-1,2,3, 3a,4,5-hexahydropyrrolo[1,2-a]quinoxaline

(37) (2S, 3aR)-2-chloro-5-[4-[(2-phenylbenzoyl)amino]benzoyl]-1,2,3,3a,4,5-hexahydropyrrolo[1,2-a]quinoxaline

(38) (2S, 3aS)-2-chloro-5-[4-[(2-phenylbenzoyl)amino]benzoyl]-1,2,3,3a,4,5-hexahydropyrrolo[1,2-a]quinoxaline

(39) (2S, 3aR)-2-chloro-5-[4-[[2-(4-tolyl)benzoyl]amino]benzoyl]-1,2,3,3a,4,5-hexahydropyrrolo[1,2-a]quinoxaline

(40) (2S, 3aS)-2-chloro-5-[4-[[2-(4-tolyl)benzoyl]amino]benzoyl]1,2,3,3a,4,5-hexahydropyrrolo[1,2a]quinoxaline

(41) (3aR)-5-[4-[(2-phenylbenzoyl)amino]benzoyl]1,2,3,3a,4,5-hexahydropyrrolo[1,2-a]quinoxalin-2-one

(42) (3aR)-5-[4-[[2-(4-tolyl)benzoyl]amino]benzoyl]-1,2,3,3a,4,5-hexahydropyrrolo[1,2-a]quinoxalin-2-one

(43) (3aS)-5-[4-[(2-phenylbenzoyl)amino]benzoyl]-1,2,3,3a,4,5-hexahydropyrrolo[1,2-a]quinoxalin-2-one

(44) (3aS)-5-[4-[[2-(4-tolyl)benzoyl]amino]benzoyl]-1,2,3,3a,4,5-hexahydropyrrolo[1,2-a]quinoxalin-2-one

(45) (11aS)-10-[4-[(2-phenylbenzoyl)amino]benzoyl]-1,2,3,10,11,11a-hexahydro-5H-pyrrolo[2,1-c][1,4]benzodiazepin-5-one

(46) (11aS)-10-[4-[[2-(4-tolyl)benzoyl]amino]benzoyl]-1,2,3,10,11,11a-hexahydro-5H-pyrrolo[2,1-c][1,4]benzodiazepin-5-one

(47) (11aR)-10-[4-[(2-phenylbenzoyl)amino]benzoyl]-1,2,3,10,11,11a-hexahydro-5H-pyrrolo[2,1-c][1,4]benzodiazepin-5-one

(48) (11aR)-10-[4-[[2-(4-tolyl)benzoyl]amino]benzoyl]-1,2,3,10,11,11a-hexahydro-5H-pyrrolo[2,1-c][1,4]benzodiazepin-5-one

(49) (2S, 11aS)-2-hydroxy-10-[4-[(2-phenylbenzoyl)amino]benzoyl]-1,2,3,10,11,11a-hexahydro-5H-pyrrolo[2,1-c][1,4]benzodiazepin-5-one

(50) (2S, 11aR)-2-hydroxy-10-[4-[(2-phenylbenzoyl)amino]benzoyl]-1,2,3,10,11,11a-hexahydro-5H-pyrrolo[2,1-c][1,4]benzodiazepin-5-one

(51) (2S, 11aS)-2-hydroxy-10-[4-[[2-(4-tolyl)benzoyl]amino]benzoyl]-1,2,3,10,11,11a-hexahydro-5H-pyrrolo[2,1-c][1,4]benzodiazepin-5-one

(52) (2S, 11aR)-2-hydroxy-10-[4-[[2-(4-tolyl)benzoyl]amino]benzoyl]-1,2,3,10,11,11a-hexahydro-5H-pyrrolo[2,1-c][1,4]benzodiazepin-5-one

(53) (2R,11aS)-2-hydroxy-10-[4-[(2-phenylbenzoyl)amino]benzoyl]-1,2,3,10,11,11a-hexahydro-5H-pyrrolo[2,1-c][1,4]benzodiazepin-5-one

(54) (2R,11aR)-2-hydroxy-10-[4-[(2-phenylbenzoyl)amino]benzoyl]-1,2,3,10,11,11a-hexahydro-5H-pyrrolo[2,1-c][1,4]benzodiazepin-5-one

(55) (2R,11aS)-2-hydroxy-10-[4-[[2-(4-tolyl)benzoyl]amino]benzoyl]-1,2,3,10,11,11a-hexahydro-5H-pyrrolo[2,1-c][1,4]benzodiazepin-5-one
(56) (2R,11aR)-2-hydroxy-10-[4-[[2-(4tolyl)benzoyl]amino]benzoyl]-1,2,3,10,11,11a-hexahydro-5H-pyrrolo[2,1-c][1,4]benzodiazepin-5-one
(57) (2R,11aS)-2-acetoxy-10-[4-[(2-phenylbenzoyl)amino]benzoyl]-1,2,3,10,11,11a-hexahydro-5H-pyrrolo[2,1-c][1,4]benzodiazepin-5-one
(58) (2R,11aR)-2-acetoxy-10-[4-[(2-phenylbenzoyl)amino]benzoyl]-1,2,3,10,11,11a-hexahydro-5H-pyrrolo[2,1-c][1,4]benzodiazepin-5-one
(59) (2R,11aS)-2-acetoxy-10-[4-[[2-(4-tolyl)benzoyl]amino]benzoyl]-1,2,3,10,11,11a-hexahydro-5H-pyrrolo[2,1-c][1,4]benzodiazepin-5-one
(60) (2R,11aR)-2-acetoxy-10-[4-[[2-(4tolyl)benzoyl]amino]benzoyl]-1,2,3,10,11,11a-hexahydro-5H-pyrrolo[2,1-c][1,4]benzodiazepin-5-one
(61) (2S, 11aS)-2-acetoxy-10-[4-[(2-phenylbenzoyl)amino]benzoyl]-1,2,3,10,11,11a-hexahydro-5H-pyrrolo[2,1-c][1,4]benzodiazepin-5-one
(62) (2S, 11aR)-2-acetoxy-10-[4-[(2-phenylbenzoyl)amino]benzoyl]-1,2,3,10,11,11a-hexahydro-5H-pyrrolo[2,1-c][1,4]benzodiazepin-5-one
(63) (2S, 11aS)-2-acetoxy-10-[4-[[2-(4-tolyl)benzoyl]amino]benzoyl]-1,2,3,10,11,11a-hexahydro-5H-pyrrolo[2,1-c][1,4]benzodiazepin-5-one
(64) (2S, 11aR)-2-acetoxy-10-[4-[[2-(4-tolyl)benzoyl]amino]benzoyl]-1,2,3,10,11,11a-hexahydro-5H-pyrrolo[2,1-c][1,4]benzodiazepin-5-one
(65) (2S, 11aS)-2-amino-10-[4-[(2-phenylbenzoyl)amino]benzoyl]-1,2,3,10,11,11a-hexahydro-5H-pyrrolo[2,1-c][1,4]benzodiazepin-5-one and hydrochloric acid salt thereof
(66) (2S, 11aR)-2-amino-10-[4-[(2-phenylbenzoyl)amino]benzoyl]-1,2,3,10,11,11a-hexahydro-5H-pyrrolo[2,1-c][1,4]benzodiazepin-5-one and hydrochloric acid salt thereof
(67) (2S, 11aS)-2-amino-10-[4-[[2-(4-tolyl)benzoyl]amino]benzoyl]-1,2,3,10,11,11a-hexahydro-5H-pyrrolo[2,1-c][1,4]benzodiazepin-5-one and hydrochloric acid salt thereof
(68) (2S, 11aR)-2-amino-10-[4-[[2-(4-tolyl)benzoyl]amino]benzoyl]-1,2,3,10,11,11a-hexahydro-5H-pyrrolo[2,1-c][1,4]benzodiazepin-5-one and hydrochloric acid salt thereof
(69) (2S, 11aS)-2-(N-ethylamino)-10-[4-[(2-phenylbenzoyl)amino]benzoyl]-1,2,3,10,11,11a-hexahydro-5H-pyrrolo[2,1-c][1,4]benzodiazepin-5-one and hydrobromic acid salt thereof
(70) (2S, 11aR)-2-N-ethylamino)-10-[4-[(2-phenylbenzoyl)amino]benzoyl]-1,2,3,10,11,11a-hexahydro-5H-pyrrolo[2,1-c][1,4]benzodiazepin-5-one and hydrobromic acid salt thereof
(71) (2S, 11aS)-2-[N-(1-methylethyl)amino]-10-[4-[[2-(4-cumenyl)benzoyl]amino]benzoyl]-1,2,3,10,11,11a-hexahydro-5H-pyrrolo[2,1-c][1,4]benzodiazepin-5-one and acetic acid salt thereof
(72) (2S, 11aR)-2-[N-(1-methylethyl)amino]-10-[4-[[2-(4-cumenyl)benzoyl]amino]benzoyl]-1,2,3,10,11,11a-hexahydro-5H-pyrrolo[2,1-c][1,4]benzodiazepin-5-one and acetic acid salt thereof
(73) (2R,11aS)-2-(N,N-dimethylamino)-10-[4-[(2-phenylbenzoyl)amino]benzoyl]-1,2,3,10,11,11a-hexahydro-5H-pyrrolo[2,1-c][1,4]benzodiazepin-5-one and hydrochloric acid salt thereof
(74) (2R,11aR)-2-(N,N-dimethylamino)-10-[4-[(2-phenylbenzoyl)amino]benzoyl]-1,2,3,10,11,11a-hexahydro-5H-pyrrolo[2,1-c][1,4]benzodiazepin-5-one and hydrochloric acid salt thereof
(75) (2R,11aS)-2-(N,N-dimethylamino)-10-[4-[[2-(4-tolyl)benzoyl]amino]benzoyl]-1,2,3,10,11,11a-hexahydro-5H-pyrrolo[2,1-c][1,4]benzodiazepin-5-one and hydrochloric acid salt thereof
(76) (2R,11aR)-2-(N,N-dimethylamino)-10-[4-[[2-(4-tolyl)benzoyl]amino]benzoyl]-1,2,3,10,11,11a-hexahydro-5H-pyrrolo[2,1-c][1,4]benzodiazepin-5-one and hydrochloric acid salt thereof
(77) (2S, 11aS)-2-(N,N-dimethylamino)-10-[4-[(2-phenylbenzoyl)amino]benzoyl]-1,2,3,10,11,11a-hexahydro-5H-pyrrolo[2,1-c][1,4]benzodiazepin-5-one and hydrochloric acid salt thereof
(78) (2S, 11aR)-2-(N,N-dimethylamino)-10-[4-[(2-phenylbenzoyl)amino]benzoyl]-1,2,3,10,11,11a-hexahydro-5H-pyrrolo[2,1-c][1,4]benzodiazepin-5-one and hydrochloric acid salt thereof
(79) (2S, 11aS)-2-(N,N-diethylamino)-10-[4-[[2-(4-tolyl)benzoyl]amino]benzoyl]-1,2,3,10,11,11a-hexahydro-5H-pyrrolo[2,1-c][1,4]benzodiazepin-5-one and hydrochloric acid salt thereof
(80) (2S, 11aR)-2-(N,N-dimethylamino)-10-[4-[[2-(4-tolyl)benzoyl]amino]benzoyl]-1,2,3,10,11,11a-hexahydro-5H-pyrrolo[2,1-c][1,4]benzodiazepin-5-one and hydrochloric acid salt thereof
(81) (2S, 11aS)-2-fluoro-10-[4-[(2-phenylbenzoyl)amino]benzoyl]-1,2,3,10,11,11a-hexahydro-5H-pyrrolo[2,1-c][1,4]benzodiazepin-5-one
(82) (2S, 11aR)-2-fluoro-10-[4-[(2-phenylbenzoyl)amino]benzoyl]-1,2,3,10,11,11a-hexahydro-5H-pyrrolo[2,1-c][1,4]benzodiazepin-5-one
(83) (2S, 11aS)-2-fluoro-10-[4-[(2-(4-tolyl)benzoyl]amino]benzoyl]-1,2,3,10,11,11a-hexahydro-5H-pyrrolo[2,1-c][1,4]benzodiazepin-5-one
(84) (2S, 11aR)-2-fluoro-10-[4-[[2-(4-tolyl)benzoyl]amino]benzoyl]-1,2,3,10,11,11a-hexahydro-5H-pyrrolo[2,1-c][1,4]benzodiazepin-5-one
(85) (2S, 11aS)-2-chloro-10-[4-[(2-phenylbenzoyl)amino]benzoyl]-1,2,3,10,11,11a-hexahydro-5H-pyrrolo[2,1-c][1,4]benzodiazepin-5-one
(86) (2S, 11aR)-2-chloro-10-[4-[(2-phenylbenzoyl)amino]benzoyl]-1,2,3,10,11,11a-hexahydro-5H-pyrrolo[2,1-c][1,4]benzodiazepin-5-one
(87) (2S, 11aS)-2-chloro-10-[4-[[2-(4-tolyl)benzoyl]amino]benzoyil-1,2,3,10,11,11a-hexahydro-5H-pyrrolo[2,1-c][1,4]benzodiazepin-5-one
(88) (2S, 11aR)-2-chloro-10-[4-[[2-(4-tolyl)benzoyl]amino]benzoyl]-1,2,3,10,11,11a-hexahydro-5H-pyrrolo[2,1-c][1,4]benzodiazepin-5-one
(89) (11aS)-10-[4-(2-phenylbenzoyl)amino]benzoyl]1,2,3,10,11,11 a-hexahydro-5H-pyrrolo[2,1-c][1,4]benzodiazepin-2,5-dione
(90) (11aR)-10-[4-[(2-phenylbenzoyl)amino]benzoyl]-1,2,3,10,11,11a-hexahydro-5H-pyrrolo[2,1-c][1,4]benzodiazepin-2,5-dione
(91) (11aS)-10-[4-[[2-(4-tolyl)benzoyl]amino]benzoyl]-1,2,3,10,11,11a-hexahydro-5H-pyrrolo[2,1-c][1,4]benzodiazepin-2,5-dione
(92) (11aR)-10-[4-[[2-(4-tolyl)benzoyl]amino]benzoyl]-1,2,3,10,11,11a-hexahydro-5H-pyrrolo[2,1-c][1,4]benzodiazepin-2,5-dione
(93) (11aS)-10-[4-[(2-phenylbenzoyl)amino]benzoyl]-1,2,3,10,11,11a-hexahydro-5H-pyrrolo[2,1-c][1,4]benzodiazepin-5-thione
(94) (11aS)-10-[4-[[2-(4-tolyl)benzoyl]amino]benzoyl]-1,2,3,10,11,11a-hexahydro-5H-pyrrolo[2,1-c][1,4]benzodiazepin-5-thione

(95) (11aR)-10-[4-[(2-phenylbenzoyl)amino]benzoyl]-1,2,3,10,11,11a-hexahydro-5H-pyrrolo[2,1-c][1,4]benzodiazepin-5-thione

(96) (11aR)-10-[4-[[2-(4-tolyl)benzoyl]amino]benzoyl]-1,2,3,10,11,11a-hexahydro-5H-pyrrolo[2,1-][1,4]benzodiazepin-5-thione

(97) (2S, 11aS)-2-hydroxy-10-[4-[(2-phenylbenzoyl)amino]benzoyl]-1,2,3,10,11,11a-hexahydro-5H-pyrrolo[2,1-c][1,4]benzodiazepin-5-thione

(98) (2S, 11aR)-2-hydroxy-10-[4-[(2-phenylbenzoyl)amino]benzoyl]-1,2,3,10,11,11a-hexahydro-5H-pyrrolo[2,1-c][1,4]benzodiazepin-5-thione

(99) (2S, 11aS)-2-hydroxy-10-[4-[[2-(4-tolyl)benzoyl]amino]benzoyl]-1,2,3,10,11,11a-hexahydro-5H-pyrrolo[2,1-c][1,4]benzodiazepin-5-thione (100) (2S, 11aR)-2-hydroxy-10-[4-[[2-(4-tolyl)benzoyl]amino]benzoyl]-1,2,3,10,11,11a-hexahydro-5H-pyrrolo[2,1-c][1,4]benzodiazepin-5-thione (101) (2R,11aS)-2-hydroxy-10-[4-[(2-phenylbenzoyl)amino]benzoyl]-1,2,3,10,11,11a-hexahydro-5H-pyrrolo[2,1-c][1,4]benzodiazepin-5-thione (102) (2R,11aR)-2-hydroxy-10-[4-[(2-phenylbenzoyl)amino]benzoyl]-1,2,3,10,11,11a-hexahydro-5H-pyrrolo[2,1-c][1,4]benzodiazepin-5-thione (103) (2R,11aS)-2-hydroxy-10-[4-[[2-(4-tolyl)benzoyl]amino]benzoyl]-1,2,3,10,11,11a-hexahydro-5H-pyrrolo[2,1-c][1,4]benzodiazepin-5-thione (104) (2R,11aR)-2-hydroxy-10-[4-[[2-(4-tolyl)benzoyl]amino]benzoyl]-1,2,3,10,11,11a-hexahydro-5H-pyrrolo[2,1-c][1,4]benzodiazepin-5-thione (105) (11aS)-10-[4-[(2-phenylbenzoyl)amino]benzoyl]-1,2,3,10,11,11a-hexahydro-pyrrolo[1,2-b][1,2,5]benzothiadiazepin-5,5-dioxide (106) (11aS)-10-[4-[[2-(4-tolyl)benzoyl]amino]benzoyl]-1,2,3,10,11,11a-hexahydro-pyrrolo[1,2-b][1,2,5]benzothiadiazepin-5,5-dioxide (107) (11aR)-10-[4-[(2-phenylbenzoyl)amino]benzoyl]-1,2,3,10,11,11a-hexahydro-pyrrolo[1,2-b][1,2,5]benzothiadiazepin-5,5-dioxide (108) (11aR)-10-[4-[[2-(4-tolyl)benzoyl]amino]benzoyl]-1,2,3,10,11,11a-hexahydro-pyrrolo[1,2-b][1,2,5)benzothiadiazepin-5,5-dioxide (109) (2S, 11aS)-2-hydroxy-10-[4-[(2-phenylbenzoyl)amino]benzoyl]-1,2,3,10,11,11a-hexahydro-pyrrolo[1,2-b][1,2,5]benzothiadiazepin-5,5-dioxide (110) (2S, 11aR)-2-hydroxy-10-[4-[(2-phenylbenzoyl)amino]benzoyl]-1,2,3,10,11,11a-hexahydro-pyrrolo[1,2-b][1,2,5]benzothiadiazepin-5,5-dioxide (111) (2S, 11aS)-2-hydroxy-10-[4-[[2-(4-tolyl)benzoyl]amino]benzoyl]-1,2,3,10,11,11a-hexahydro-pyrrolo[1,2-b][1,2,5]benzothiadiazepin-5,5-dioxide (112) (2S, 11aR)-2-hydroxy-10-[4-[[2-(4-tolyl)benzoyl]amino]benzoyl]-1,2,3,10,11,11a-hexahydro-pyrrolo[1,2-b][1,2,5]benzothiadiazepin-5,5-dioxide (113) (2R,11aS)-2-hydroxy-10-[4-[(2-phenylbenzoyl)amino]benzoyl]-1,2,3,10,11,11a-hexahydro-pyrrolo[1,2-b][1,2,5]benzothiadiazepin-5,5-dioxide (114) (2R,11aR)-2-hydroxy-10-[4-[(2-phenylbenzoyl)amino]benzoyl]-1,2,3,10,11,11a-hexahydro-pyrrolo[1,2-b][1,2,5]benzothiadiazepin-5,5-dioxide (115) (2R,11aS)-2-hydroxy-10-[4-[[2-(4-tolyl)benzoyl]amino]benzoyl]-1,2,3,10,11,11a-hexahydro-pyrrolo[1,2-b][1,2,5]benzothiadiazepin-5,5-dioxide (116) (2R,11aR)-2-hydroxy-10-[4-[[2-(4-tolyl)benzoyl]amino]benzoyl]-1,2,3,10,11,11a-hexahydro-pyrrolo[1,2-b][1,2,5]benzothiadiazepin-5,5-dioxide (117) (11aS)-10-[4-[(2-phenylbenzoyl)amino]benzoyl]-1,2,3,10,11,11a-hexahydro-5H-pyrrolo[2,1-c][1,4]benzodiazepine and hydrochloric acid salt thereof (118) (11aS)-10-[4-[[2-(4-tolyl)benzoyl]amino]benzoyl]-1,2,3,10,11,11a-hexahydro-5H-pyrrolo[2,1-c][1,4]benzodiazepine and hydrochloric acid salt thereof (119) (11aR)-10-[4-[(2-phenylbenzoyl)amino]benzoyl]-1,2,3,10,11,11a-hexahydro-5H-pyrrolo[2,1-c][1,4]benzodiazepine and hydrochloric acid salt thereof (120) (11aR)-10-[4-[[2-(4-tolyl)benzoyl]amino]benzoyl]-1,2,3,10,11,11a-hexahydro-5H-pyrrolo[2,1-c][1,4]benzodiazepine and hydrochloric acid salt thereof (121) (2S, 11aS)-2-hydroxy-10-[4-[(2-phenylbenzoyl)amino]benzoyl]-1,2,3,10,11,11a-hexahydro-5H-pyrrolo[2,1-c][1,4]benzodiazepine and hydrochloric acid salt thereof (122) (2S, 11aR)-2-hydroxy-10-[4-[(2-phenylbenzoyl)amino]benzoyl]-1,2,3,10,11,11a-hexahydro-5H-pyrrolo[2,1-c][1,4]benzodiazepine and hydrochloric acid salt thereof (123) (2S, 11aS)-2-hydroxy-10-[4-[[2-(4-tolyl)benzoyl]amino]benzoyl]-1,2,3,10,11,11a-hexahydro-5H-pyrrolo[2,1-c][1,4]benzodiazepine and hydrochloric acid salt thereof (124) (2S, 11aR)-2-hydroxy-10-[4-[[2-(4-tolyl)benzoyl]amino]benzoyl]-1,2,3,10,11,11a-hexahydro-5H-pyrrolo[2,1-c][1,4]benzodiazepine and hydrochloric acid salt thereof (125) (2R,11aS)-2-hydroxy-10-[4-[(2-phenylbenzoyl)amino]benzoyl]-1,2,3,10,11,11a-hexahydro-5H-pyrrolo[2,1-c][1,4]benzodiazepine and hydrochloric acid salt thereof (126) (2R,11aR)-2-hydroxy-10-[4-[(2-phenylbenzoyl)amino]benzoyl]- 1,2,3,10,11,11a-hexahydro-5H-pyrrolo[2,1-c][1,4]benzodiazepine and hydrochloric acid salt thereof (127) (2R,11aS)-2-hydroxy-10-[4-[[2-(4-tolyl)benzoyl]amino]benzoyl]-1,2,3,10,11,11a-hexahydro-5H-pyrrolo[2,1-c][1,4]benzodiazepine and hydrochloric acid salt thereof (128) (2R,11aR)-2-hydroxy-10-[4-[[2-(4-tolyl)benzoyl]amino]benzoyl]-1,2,3,10,11,11a-hexahydro-5H-pyrrolo[2,1-c][1,4]benzodiazepine and hydrochloric acid salt thereof (129) (2R,11aS)-2-acetoxy-10-[4-[(2-phenylbenzoyl)amino]benzoyl]-1,2,3,10,11,11a-hexahydro-5H-pyrrolo[2,1-c][1,4]benzodiazepine and hydrochloric acid salt thereof (130) (2R,11aR)-2-acetoxy-10-[4-[(2-phenylbenzoyl)amino]benzoyl]-1,2,3,10,11,11a-hexahydro-5H-pyrrolo[2,1-c][1,4]benzodiazepine and hydrochloric acid salt thereof (131) (2R,11aS)-2-acetoxy-10-[4-[[2-(4-tolyl)benzoyl]amino]benzoyl]-1,2,3,10,11,11a-hexahydro-5H-pyrrolo[2,1-c][1,4]benzodiazepine and hydrochloric acid salt thereof (132) (2R,11aR)-2-acetoxy-10-[4-[[2-(4-tolyl)benzoyl]amino]benzoyl]-1,2,3,10,11,11a-hexahydro-5H-pyrrolo[2,1-c][1,4]benzodiazepine and hydrochloric acid salt thereof (133) (2S, 11aS)-2-acetoxy-10-[4-[(2-phenylbenzoyl)amino]benzoyl]-1,2,3,10,11,11a-hexahydro-5H-pyrrolo[2,1-c][1,4]benzodiazepine and hydrochloric acid salt thereof (134) (2S, 11aR)-2-acetoxy-10-[4-[(2-phenylbenzoyl)amino]benzoyl]-1,2,3,10,11,11a-hexahydro-5H-pyrrolo[2,1-c][1,4]benzodiazepine and hydrochloric acid salt thereof (135) (2S, 11aS)-2-acetoxy-10-[4-[[2-(4-tolyl)benzoyl]amino]benzoyl]-1,2,3,10,11,11a-hexahydro-5H-pyrrolo[2,1-c][1,4]benzodiazepine and hydrochloric acid salt thereof (136) (2S, 11aR)-2-acetoxy-10-[4-[[2-(4-tolyl)benzoyl]amino]benzoyl]-1,2,3,10,11,11a-hexahydro-5H-pyrrolo[2,1-c][1,4]benzodiazepine and hydrochloric acid salt thereof (137) (2R,11aS)-2-amino-10-[4-[(2-phenylbenzoyl)amino]benzoyl]-1,2,3,10,11,11a-hexahydro-5H-pyrrolo[2,1-c][1,4]benzodiazepine and hydrochloric add salt thereof (138) (2R,11aR)-2-amino-10-[4-[(2-phenylbenzoyl)amino]benzoyl]-1,2,3,10,11,11a-hexahydro-5H-pyrrolo[2,1-c][1,4]benzodiazepine and hydrochloric add salt thereof (139) (2R,11aS)-2-amino-1-[4-[[2-(4tolyl)benzoyl]amino]benzoyl]-1,2,3,10,11,11a-hexahydro-5H-pyrrolo[2,1-c][1,4]benzodiazepine and hydrochloric acid salt thereof (140) (2R,11aR)-2-amino-10-[4-[[2-(4-tolyl)benzoyl]amino]benzoyl]-1,2,3,10,11,11a-hexahydro-5H-pyrrolo[2,1-c][1,4]benzodiazepine and hydrochloric acid salt thereof (141) (2S, 11aS)-2-(N-ethylamino)-10-[4-[(2-phenylbenzoyl)amino]benzoyl]-1,2,3,10,11,11a-hexahydro-5H-pyrrolo[2,1-c][1,4]benzodiazepine and hydrobromic acid salt thereof (142) (2S, 11aR)-2-(N-ethylamino)-10-[4-[(2-phenylbenzoyl)amino]benzoyl]-1,2,3,10,11,11a-hexahydro-5H-pyrrolo[2,1-c][1,4]benzodiazepine and hydrobromic acid salt thereof (143) (2S, 11aS)-2-[N-(1-methylethyl)amino]-10-[4-[[2-(4-cumenyl)benzoyl]amino]benzoyl]-1,2,3,10,11,11a-hexahydro-5H-pyrrolo[2,1-c][1,4]benzodiazepine and hydrochloric acid salt thereof (144) (2S, 11aR)-2-[N-(1-methylethyl)amino]-10-[4-[[2-(4-cumenyl)benzoyl]amino]benzoyl]-1,2,3,10,11,11a-hexahydro-5H-pyrrolo[2,1-c][1,4]benzodiazepine and hydrochloric acid salt thereof (145) (2S, 11aS)-2-(N,N-dimethylamino)-10-[4-[(2-phenylbenzoyl)amino]benzoyl]-1,2,3,10,11,11a-hexahydro-5H-pyrrolo[2,1-c][1,4]benzodiazepine and hydrochloric acid salt thereof (146) (2S, 11aR)-2-(N,N-dimethylamino)-10-[4-[(2-phenylbenzoyl)amino]benzoyl]-1,2,3,10,11,11a-hexahydro-5H-pyrrolo[2,1-c][1,4]benzodiazepine and hydrochloric acid salt thereof (147) (2S, 11aS)-2-(N,N-dimethylamino)-10-[4-[[2-(4-tolyl)benzoyl]amino]benzoyl]-1,2,3,10,11,11a-hexahydro-5H-pyrrolo[2,1-c][1,4]benzodiazepine and hydrochloric acid salt thereof (148) (2S, 11aR)-2-(N,N-dimethylamino)-10-[4-[[2-(4-tolyl)benzoyl]amino]benzoyl]-1,2,3,10,11,11a-hexahydro-5H-pyrrolo[2,1-c][1,4]benzodiazepine and hydrochloric acid salt thereof (149) (2S, 11aS)-2-fluoro-10-[4-[(2-phenylbenzoyl)amino]benzoyl]-1,2,3,10,11,11a-hexahydro-5H-pyrrolo[2,1-c][1,4]benzodiazepine and hydrochloric acid salt thereof (150) (2S, 11aR)-2-fluoro-10-[4-[(2-phenylbenzoyl)amino]benzoyl]-1,2,3,10,11,11a-hexahydro-5H-pyrrolo[2,1-c][1,4]benzodiazepine and hydrochloric acid salt thereof (151) (2S, 11aS)-2-fluoro-10-[4-[[2-(4-tolyl)benzoyl]amino]benzoyl]-1,2,3,10,11,11a-hexahydro-5H-pyrrolo[2,1-c][1,4]benzodiazepine and hydrochloric acid salt thereof (152) (2S, 11aR)-2-fluoro-10-[4-[[2-(4-tolyl)benzoyl]amino]benzoyl]-1,2,3,10,11,11a-hexahydro-5H-pyrrolo[2,1-c][1,4]benzodiazepine an hydrochloric acid salt thereof (153) (2S, 11aS)-2-chloro-10-[4-[(2-phenylbenzoyl)amino]benzoyl]-1,2,3,10,11,11a-hexahydro-5H-pyrrolo[2,1-c][1,4]benzodiazepine and maleic acid salt thereof (154) (2S, 11aR)-2-chloro-10-[4-[(2-phenylbenzoyl)amino]benzoyl]-1,2,3,10,11,11a-hexahydro-5H-pyrrolo[2,1-c][1,4]benzodiazepine and maleic acid salt thereof (155) (2S, 11aS)-2-chloro-10-[4-[[2-(4-tolyl)benzoyl]amino]benzoyl]- 1,2,3,10,11,11a-hexahydro-5H-pyrrolo[2,1-c][1,4]benzodiazepine and maleic acid salt thereof (156) (2S, 11aR)-2-chloro-10-[4-[[2-(4-tolyl)benzoyl]amino]benzoyl]-1,2,3,10,11,11a-hexahydro-5H-pyrrolo[2,1-c][1,4]benzodiazepine and maleic acid salt thereof (157) (11aS)-10-[4-[(2-phenylbenzoyl)amino]benzoyl]-1,2,3,10,11,11a-hexahydro-5H-pyrrolo[2,1-c][1,4]benzodiazepin-2-one and hydrochloric acid salt thereof (158) (11aR)-10-[4-[(2-phenylbenzoyl)amino]benzoyl]-1,2,3,10,11,11a-hexahydro-5H-pyrrolo[2,1-c][1,4]benzodiazepin-2-one and hydrochloric acid salt thereof (159) (11aS)-10-[4-[[2-(4-tolyl)benzoyl]amino]benzoyl]-1,2,3,10,11,11a-hexahydro-5H-pyrrolo[2,1-c][1,4]benzodiazepin-2-one and hydrochloric acid salt thereof (160) (11aR)-10-[4-[[2-(4-tolyl)benzoyl]amino]benzoyl]-1,2,3,10,11,11a-hexahydro-5H-pyrrolo[2,1-c][1,4]benzodiazepin-2-one and hydrochloric acid salt thereof (161) (3aS)-6-[4-[(2-phenylbenzoyl)amino]benzoyl]-2,3,3a,4,5,6-hexahydro-1H-pyrrolo[1,2-a][1,5]benzodiazepine (162) (3aS)-6-[4-[[2-(4-tolyl)benzoyl]amino]benzoyl]-2,3,3a,4,5,6-hexahydro-1H-pyrrolo[1,2-a][1,5]benzodiazepine (163) (3aR)-6-[4-[(2-phenylbenzoyl)amino]benzoyl]-2,3,3a,4,5,6-hexahydro-1H-pyrrolo[1,2-a][1,5]benzodiazepine (164) (3aR)-6-[4-[[2-(4-tolyl)benzoyl]amino]benzoyl]-2,3,3a,4,5,6-hexahydro-1H-pyrrolo[1,2-a][1,5]benzodiazepine (165) (2S, 3aS)-2-hydroxy-6-[4-[(2-phenylbenzoyl)amino]benzoyl]-2,3,3a,4,5,6-hexahydro-1H-pyrrolo[1,2-a][1,5]benzodiazepine (166) (2S, 3aR)-2-hydroxy-6-[4-[(2-phenylbenzoyl)amino]benzoyl]-2,3,3a,4,5,6-hexahydro-1H-pyrrolo[1,2-a][1,5]benzodiazepine (167) (2S, 3aS)-2-hydroxy-6-[4-[[2-(4-tolyl)benzoyl]amino]benzoyl]-2,3,3a,4,5,6-hexahydro-1H-pyrrolo[1,2-a][1,5]benzodiazepine (168) (2S, 3aR)-2-hydroxy-6-[4-[[2-(4-tolyl)benzoyl]amino]benzoyl]-2,3,3a,4,5,6-hexahydro-1H-pyrrolo[1,2-a][1,5]benzodiazepine (169) (2R,3aS)-2-hydroxy-6-[4-[(2-phenylbenzoyl)amino]benzoyl]-2,3,3a,4,5,6-hexahydro-1H-pyrrolo[1,2-a][1,5]benzodiazepine (170) (2R,3aR)-2-hydroxy-6-[4-[(2-phenylbenzoyl)amino]benzoyl]-2,3,3a,4,5,6-hexahydro-1H-pyrrolo[1,2-a][1,5]benzodiazepine (171) (2R,3aS)-2-hydroxy-6-[4-[[2-(4-tolyl)benzoyl]amino]benzoyl]-2,3,3a,4,5,6-hexahydro-1H-pyrrolo[1,2-a][1,5]benzodiazepine (172) (2R,3aR)-2-hydroxy-6-[4-[[2-(4-tolyl)benzoyl]amino]benzoyl]-2,3,3a,4,5,6-hexahydro-1H-pyrrolo[1,2-a][1,5]benzodiazepine (173) (2R,3aS)-2-acetoxy-6-[4-[(2-phenylbenzoyl)amino]benzoyl]-2,3,3a,4,5,6-hexahydro-1H-pyrrolo[1,2-a][1,5]benzodiazepine (174) (2R,3aR)-2-acetoxy-6-[4-[(2-phenylbenzoyl)amino]benzoyl]-2,3,3a,4, 5,6-hexahydro-1H-pyrrolo[1,2-a][1,5]benzodiazepine (175) (2R,3aS)-2-acetoxy-6-[4-[[2-(4-tolyl)benzoyl]amino]benzoyl]-2,3,3a,4,5,6-hexahydro-1H-pyrrolo[1,2-a][1,5]benzodiazepine (176) (2R,3aR)-2-acetoxy-6-[4-[[2-(4-tolyl)benzoyl]amino]benzoyl]-2,3, 3a,4,5,6-hexahydro-1H-pyrrolo[1,2-a][1,5]benzodiazepine (177) (2S, 3aS)-2-acetoxy-6-[4-[(2-phenylbenzoyl)amino]benzoyl]-2,3,3a, 4,5,6-hexahydro-1H-pyrrolo[1,2-a][1,5]benzodiazepine (178) (2S, 3aR)-2-acetoxy-6-[4-[(2-phenylbenzoyl)amino]benzoyl]-2,3,3a, 4,5,6-hexahydro-1H-pyrrolo[1,2-a][1,5]benzodiazepine
(179) (2S, 3aS)-2-acetoxy-6-[4-[[2-(4-tolyl)benzoyl]amino]benzoyl]-4,5,6-hexahydro-1H-pyrrolo[1,2-a][1,5]benzodiazepine
(180) (2S, 3aR)-2-acetoxy-6-[4-[[2-(4-tolyl)benzoyl]amino]benzoyl]-2,3,3a,4,5,6-hexahydro-1H-pyrrolo[1,2-a][1,5]benzodiazepine
(181) (2R,3aS)-2-amino-6-[4-[(2-phenylbenzoyl)amino]benzoyl]-2,3,3a, 4,5,6-hexahydro-1H-pyrrolo[1,2-a][1,5]benzodiazepine and hydrochloric acid salt thereof
(182) (2R,3aR)-2-amino-6-[4-[(2-phenylbenzoyl)amino]benzoyl]-2,3,3a, 4,5,6-hexahydro-1H-pyrrolo[1,2-a][1,5]benzodiazepine and hydrochloric acid salt thereof
(183) (2R,3aS)-2-amino-6-[4-[[2-(4tolyl)benzoyl]amino]benzoyl]-2,3,3a,4,5,6-hexahydro-1H-pyrrolo[1,2-a][1,5]benzodiazepine and hydrochloric acid salt thereof
(184) (2R,3aR)-2-amino-6-[4-[[2-(4-tolyl)benzoyl]amino]benzoyl]-2,3,3a 4,5,6-hexahydro-1H-pyrrolo[1,2-a][1,5]benzodiazepine and hydrochloric acid salt thereof
(185) (2S, 3aS)-2-amino-6-[4-[(2-phenylbenzoyl)amino]benzoyl]-2,3,3a, 4,5,6-hexahydro-1H-pyrrolo[1,2-a][1,5]benzodiazepine and hydrochloric acid salt thereof
(186) (2S, 3aR)-2-amino-6-[4-[(2-phenylbenzoyl)amino]benzoyl]-2,3,3a, 4,5,6-hexahydro-1H-pyrrolo[1,2-a][1,5]benzodiazepine and hydrochloric acid salt thereof
(187) (2S, 3aS)-2-amino-6-[4-[[2-(4-tolyl)benzoyl]amino]benzoyl]-2,3,3a, 4,5,6-hexahydro-1H-pyrrolo[1,2-a][1,5]benzodiazepine and hydrochloric acid salt thereof
(188) (2S, 3aR)-2-amino-6-[4-[[2-(4-tolyl)benzoyl]amino]benzoyl]-2,3,3,3a,4,5,6-hexahydro-1H-pyrrolo[1,2-a][1,5]benzodiazepine and hydrochloric acid salt thereof
(189) (2S, 3aS)-2-(N-ethylamino)-6-[4-[(2-phenylbenzoyl)amino]benzoyl]-2,3,3a,4,5,6-hexahydro-1H-pyrrolo[1,2-a][1,5]benzodiazepine and hydrobromic acid salt thereof
(190) (2S, 3aR)-2-(N-ethylamino)-6-[4-[2-phenylbenzoyl)amino]benzoyl]-2,3,3a,4,5,6-hexahydro-1H-pyrrolo[1,2-a][1,5]benzodiazepine and hydrobromic acid salt thereof
(191) (2S, 3aS)-2-[N-(1-methylethyl)amino]-6-[4-[[2-(4-cumenyl)benzoyl]amino]benzoyl]-2,3,3a,4,5,6-hexahydro-1H-pyrrolo[1,2-a][1,5]benzodiazepine and hydrochloric acid salt thereof
(192) (2S, 3aR)-2-[N-(1-methylethyl)amino]-6-[4-[[2-(4-cumenyl)benzoyl]amino]benzoyl]-2,3,3a,4,5,6-hexahydro-1H-pyrrolo[1,2-a][1,5]benzodiazepine and hydrochloric acid salt thereof
(193) (2R,3aS)-2-(N,N-dimethylamino)-6-[4-[(2-phenylbenzoyl)amino]benzoyl]-2,3,3a,4,5,6-hexahydro-1H-pyrrolo[1,2-a][1,5]benzodiazepine and hydrochloric acid salt thereof
(194) (2R,3aR)-2-(N,N-dimethylamino)-6-[4-[(2-phenylbenzoyl)amino]benzoyl]-2,3,3a,4,5,6-hexahydro-1H-pyrrolo[1,2-a][1,5]benzodiazepine and hydrochloric acid sat thereof
(195) (2R,3aS)-2-(N,N-dimethylamino)-6-[4-[[2-(4-tolyl)benzoyl]amino]benzoyl]-2,3,3a,4,5,6-hexahydro-1H-pyrrolo[1,2-a][1,5]benzodiazepine and hydrochloric acid salt thereof
(196) (2R,3aR)-2-(N,N-dimethylamino)-6-[4-[[2-(4-tolyl)benzoyl]amino]benzoyl]-2,3,3a,4,5,6-hexahydro-1H-pyrrolo[1,2-a][1,5]benzodiazepine and hydrochloric acid salt thereof
(197) (2S, 3aR)-2-(N,N-dimethylamino)-6-[4-[(2-phenylbenzoyl)amino]benzoyl]-2,3,3a,4,5,6-hexahydro-1H-pyrrolo[1,2-a][1,5]benzodiazepine and hydrochloric acid salt thereof
(198) (2S, 3aR)-2-(N,N-dimethylamino)-6-[4-[(2-phenylbenzoyl)amino]benzoyl]-2,3,3a,4,5,6-hexahydro-1H-pyrrolo[1,2-a][1,5]benzodiazepine and hydrochloric acid salt thereof
(199) (2S, 3aS)-2-(N,N-dimethylamino)-6-[4-[[2-(4-tolyl)benzoyl]amino]benzoyl]-2,3,3a,4,5,6-hexahydro-1H-pyrrolo[1,2-a][1,5]benzodiazepine and hydrochloric acid salt thereof
(200) (2S, 3aR)-2-(N,N-dimethylamino)-6-[4-[[2-(4-tolyl)benzoyl]amino]benzoyl]-2,3,3a,4,5,6-hexahydro-1H-pyrrolo[1,2-a][1,5 ]benzodiazepine and hydrochloric acid salt thereof
(201) (2S, 3aS)-2-fluoro-6-[4-[(2-phenylbenzoyl)amino]benzoyl]-2,3,3a,4, 5,6-hexahydro-1H-pyrrolo[1,2-a][1,5]benzodiazepine
(202) (2S, 3aR)-2-fluoro-6-[4-[(2-phenylbenzoyl)amino]benzoyl]-2,3,3a,4, 5,6-hexahydro-1H-pyrrolo[1,2-a][1,5]benzodiazepine
(203) (2S, 3aS)-2-fluoro-6-[4-[[2-(4tolyl)benzoyl]amino]benzoyl]-2,3,3a 4,5,6-hexahydro-1H-pyrrolo[1,2-a][1,5]benzodiazepine
(204) (2S, 3aR)-2-fluoro-6-[4-[[2-(4-tolyl)benzoyl]amino]benzoyl]-2,3,3a4,5,6-hexahydro-1H-pyrrolo[1,2-a][1,5]benzodiazepine
(205) (2S, 3aS)-2-chloro-6-[4-[(2-phenylbenzoyl)amino]benzoyl]-2,3,3a,4,5,6-hexahydro-1H-pyrrolo[1,2-a][1,5]benzodiazepine
(206) (2S, 3aR)-2-chloro-6-[4-[(2-phenylbenzoyl)amino]benzoyl]-2,3,3a,4,5,6-hexahydro-1H-pyrrolo[1,2-a][1,5]benzodiazepine
(207) (2S, 3aS)-2-chloro-6-[4-[[2-(4-tolyl)benzoyl]amino]benzoyl]-2,3,3a4,5,6-hexahydro-1H-pyrrolo[1,2-a][1,5]benzodiazepine
(208) (2S, 3aR)-2-chloro-6-[4-[[2-(4-tolyl)benzoyl]amino]benzoyl]-2,3,3a,4,5,6-hexahydro-1H-pyrrolo[1,2-a][1,5]benzodiazepine
(209) (3aS)-6-[4-[(2-phenylbenzoyl)amino]benzoyl]-2,3,3a, 4,5,6-hexahydro-1H-pyrrolo[1,2-a][1,5]benzodiazepin-2-one
(210) (3aR)-6-[4-[(2-phenylbenzoyl)amino]benzoyl]-2,3, 3a,4,5,6-hexahydro-1H-pyrrolo[1,2-a][1,5]benzodiazepin-2-one
(211) (3aS)-6-[4-[[2-(4-tolyl)benzoyl]amino]benzoyl]-2,3, 3a,4,5,6-hexahydro-1H-pyrrolo[1,2-a][1,5]benzodiazepin-2-one
(212) (3aR)-6-[4-[[2-(4-tolyl)benzoyl]amino]benzoyl]-2,3, 3a,4,5,6-hexahydro-1H-pyrrolo[1,2-a][1,5]benzodiazepin-2-one The compound represented by the general formula (1) will hereunder be referred to as the compound (1) of the present invention. The compound (1) of the present invention and salts thereof may be synthesized by a variety of methods. The following are typical examples of such preparation methods

[Reaction Scheme 1]

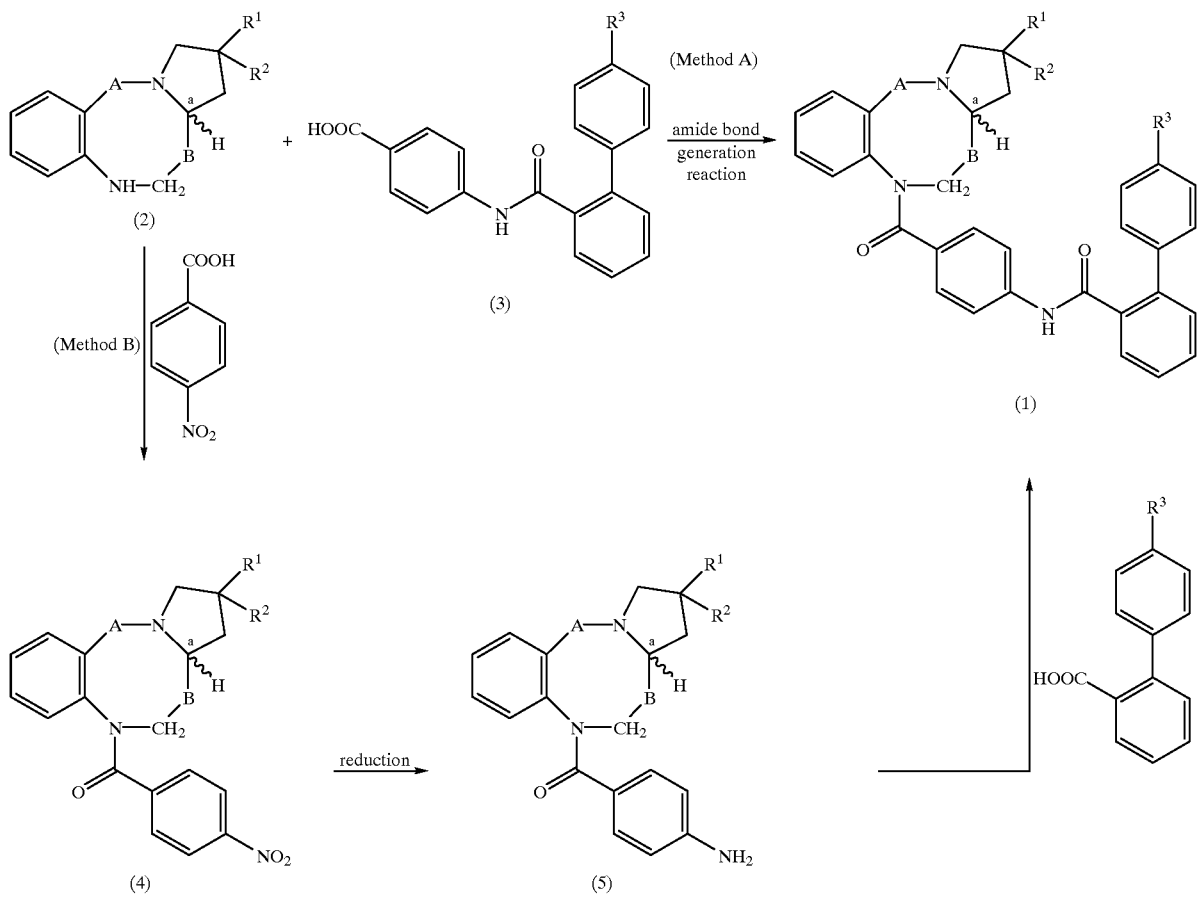

[In these formulas, $R^1$, $R^2$, $R^3$, A, B, a are the same as those defined above].

In [Reaction Scheme 1], there are disclosed a method A which comprises the step of subjecting a tricyclic compound (2) and a carboxylic acid (3) to the usual amide bond-forming reaction to give a compound (1) of the present invention; and a method B which comprises the steps of condensing a tricyclic compound (2) and 4-nitrobenzoic acid to give a compound (4), reducing the nitro group of the compound (4) to an amino group and then condensing the resulting compound (5) with a substituted or unsubstituted biphenyl carboxylic acid to thus give the compound (1) of the present invention.

The amide bond-forming reaction (the method A) may easily be put in operation using the conditions for the known amide bond-forming reaction. Such known amide bond-forming reaction can be carried out by, for instance, (i) the acid chloride method, which comprises the steps of reacting a carboxylic acid (3) with a halogenation agent such as thionyl chloride, oxalyl chloride, phosphorus pentachloride to give an acid chloride and then reacting the resulting product with a tricyclic compound (2); (ii) the carbodiimide method which comprises the step of reacting a carboxylic acid (3) with a tricyclic compound (2) in the presence of a condensation agent such as N,N'-dicyclohexyl carbodiimide, N-ethyl-N'-(3-dimethylamino-propyl) carbodiimide, carbonyl diimidazole; (i) the activated ester method which comprises the steps of converting a carboxylic acid (3) into an activated ester such as a nitro- or halogen-substituted phenyl ester, an aromatic thioester, an N-hydroxy succinic acid ester, a 1-hydroxy benzotriazole ester or an enol ester and then reacting the resulting product with a tricyclic compound (2). Other methods (iv) may likewise be used and examples thereof usable herein include a method which comprises the steps of converting a carboxylic acid (3) into a carboxylic acid anhydride using a dehydrating agent such as acetic anhydride and then reacting the anhydride with a tricyclic compound (2); a method which comprises the step of reacting an ester of a carboxylic acid (3) and a lower alcohol with a tricyclic compound (2) under high pressure and temperature conditions; and a method which comprises the step of reacting a carboxylic acid (3) with a tricyclic compound (2) in the presence of a condensation agent or a phosphorus atom-containing compound such as triphenyl phosphine, diphenyl phosphine chloride, phenyl-N-phenylphosphoramide chloridate, diethyl chlorophosphate, diethyl cyanophosphate, diphenyl phosphoric acid azide, bis(2-oxo-3-oxazolidinyl) phosphinic chloride. In particular, the acid chloride method is advantageous, because it is simple and is easily practicable.

The solvent used in the reaction may vary depending on the method selected, but examples thereof generally used include halogenated hydrocarbons such as dichloromethane, dichloroethane and chloroform; aromatic hydrocarbons such as benzene, toluene and xylene; ethers such as diethyl ether, tetrahydrofuran, dioxane and dimethoxy ethane; esters such as ethyl acetate; aprotic polar solvents such as N,N-dimethylformamide, dimethyl sulfoxide and hexamethyl phosphoric acid triamide, which may be used alone or in any combination When the reaction is put in operation, it is sometimes effective to carry out the reaction using an excess of the tricyclic compound (2) or in the presence of an organic base such as N-methylmorpholine, trimethylamine, triethylamine, N,N-dimethylamine, pyridine, 1,5-diazabicyclo[4,3,0]nonene-5 (DBN), 1,8-diazabicyclo[5,4,0]undecene-7 (DBI) or 1,4-diazabicyclo[2,2,2]octane (DABCO); or an inorganic base such as potassium carbonate, sodium carbonate, potassium hydrogencarbonate or sodium hydrogencarbonate, in order to make the progress of the reaction smooth. The reaction temperature usually ranges from about −20 to 150° C. and preferably about −5 to 50° C., while the reaction time ranges from about 5 minutes to 18 hours and preferably 5 minutes to 2 hours.

The method B for preparing the compound (1) of the present invention starting from a tricyclic compound (2) comprises the steps of reacting the compound (2) with 4-nitrobenzoic acid under the foregoing conditions for the amide bond-forming reaction to give a compound (4), reducing the nitro group of the compound (4) into an amino group to thus give a compound (5), condensing the compound (5) with a substituted or unsubstituted biphenyl carboxylic acid under the foregoing conditions for the amide bond-forming reaction to give a compound (1) of the present invention. Methods for reduction may be, for instance, chemical reduction and catalytic reduction, which may be carried out according to the usual manner. Examples of reducing agents preferably used in the chemical reduction include metals such as tin, zinc and iron; or metal compounds such as chromium chloride and chromium acetate and the reduction may be carried out under acidic, neutral or basic conditions. Examples of acids used in this case are organic acids such as formic acid, acetic acid, trifluoroacetic acid, and p-toluenesulfonic acid; or inorganic acids such as hydrochloric acid and hydrobromic acid. If a base is used, examples thereof are ammonia, ammonium chloride, and sodium hydroxide. Examples of other reducing agents include aluminum hydride compounds such as aluminum hydride, lithium aluminum hydride and sodium aluminum hydride; boron hydride compounds such as sodium boron hydride, lithium boron hydride, sodium cyanoboron hydride, borane and diborane. These other reducing agents can also provide good results. Examples of catalysts suitably used in the catalytic reduction include palladium-containing catalysts such as palladium-carbon, palladium oxide, sponge-like palladium and colloidal palladium; nickel-containing catalysts such as Raney nickel, nickel oxide and reduced nickel; and platinum-containing catalysts such as platinum plate, platinum oxide and sponge-like platinum. The reducing reaction is in general carried out in a solvent. Examples of solvent suitably used in the reduction are alcohols such as methanol, ethanol and propanol; ethers such as diethyl ether, dioxane, tetrahydrofuran and dimethoxy ethane; and water, which may be used alone or in any combination. The reaction temperature is not restricted to any specific range, but the reaction is preferably carried out with heating or cooling. The reduction is usually carried out at a temperature ranging from −20 to 50° C. for 5 minutes to 18 hours.

In the reactions according to the methods A and B, if the tricyclic compound (2) carries a hydroxyl group, the foregoing reaction is put in operation after introducing a protective group into the compound and therefore, the intended compound can be obtained after removal of the protective group. Examples of such protective groups are those disclosed in Greene & Wuts, Protective Groups in Organic Synthesis, $2^{nd}$ edition, which are appropriately selected, while taking into consideration the selected reaction conditions.

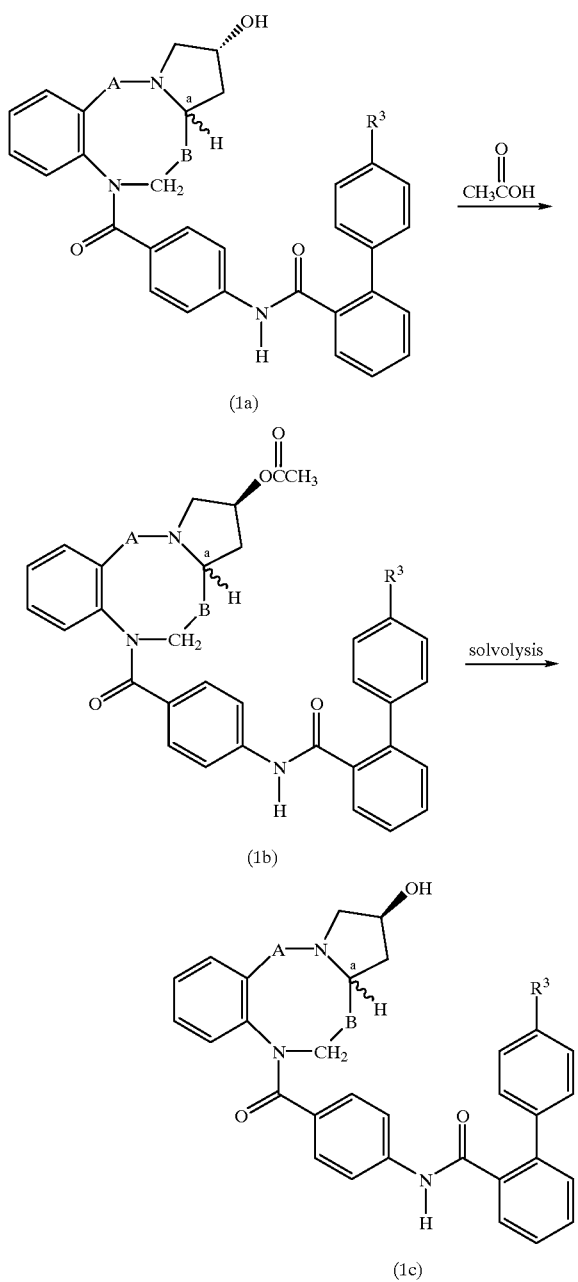

[In these formulas, $R^3$, A, B and a are the same as those defined above].

The compound (1a) which is a compound (1) of the present invention whose $R^1$ is . . . OH may be converted into a compound (1c) whose steric configuration is reversed, using the MITSUNOBU REACTION (O. Mitsunobu, Synthesis, 1–28, 1981). More specifically, the compound (1a) is reacted with acetic acid in the presence of triphenyl phosphine and azodicarboxylic acid diesters such as diethyl azodicarboxylate, diisopropyl azodicarboxylate and dibenzyl azodicarboxylate in an aprotic polar solvent such as N,N-dimethylformamide, dimethyl sulfoxide or hexamethyl phosphoric acid triamide to give an acetate derivative (1b) in which the steric configuration is reversed and then subjecting the derivative (1b) to solvoly in the presence of an acid or a base in a solvent such as water or an alcohol such as methanol or ethanol to give a compound (1c).

[Reaction Scheme 3]

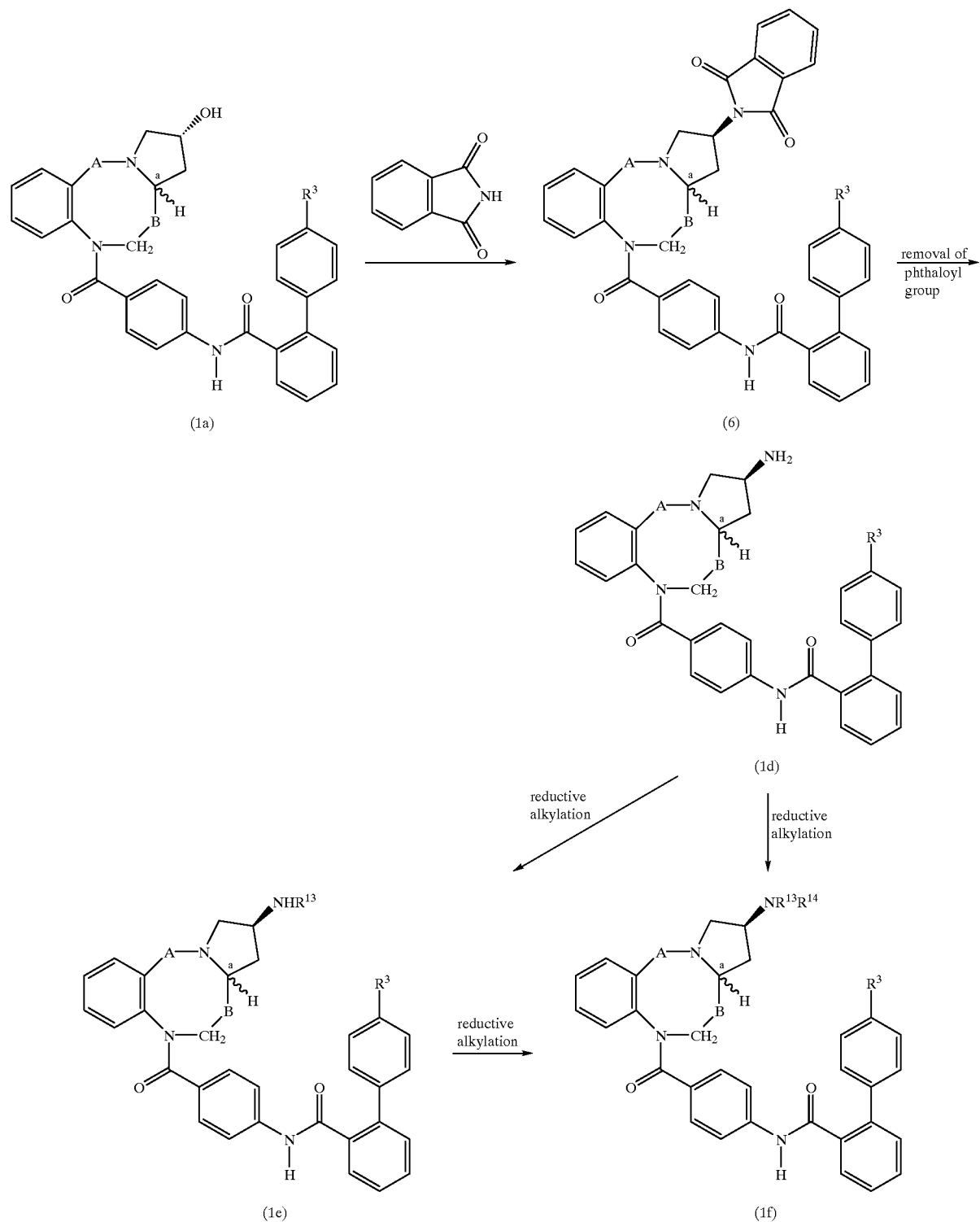

[In these formulas, $R^3$, A, B and a are the same as those defined above and $R^{13}$ and $R^{14}$ each independently represents an alkyl group having 1 to 4 carbon atoms].

The compounds (1d), (1e) and (1f) can be prepared from the compound (1a) according to the [Reaction Scheme 3]. More specifically, the compound (1a) is reacted with phthalimide in the presence of triphenyl phosphine and azodicarboxylic acid diesters such as diethyl azodicarboxylate, diisopropyl azodicarboxylate and dibenzyl azodicarboxylate in an aprotic polar solvent such as N,N-dimethylformamide, dimethyl sulfoxide or hexamethyl phosphoric acid triamide to give an imide derivative (6) in which the steric configuration is reversed and then treating the imide derivative (6) with a hydrazine compound such as hydrazine, methyl hydrazine or ethyl hydrazine to eliminate the phthaloyl group and to thus give an amine derivative (1d).

The monoalkylamine derivative (1e) can be prepared by condensing the amine derivative (1d) with a carbonyl compound such as acetaldehyde, propyl aldehyde, acetone or methyl ethyl ketone and then reducing the resulting imine with a reducing agent Examples of reducing agents are composite hydrogen-containing compounds such as lithium aluminum hydride, sodium boron hydride, sodium cyanoboron hydride and diborane; sodium, sodium amalgam and titanium chloride. The catalytic reduction using palladium, platinum, or Raney nickel as a catalyst is also effective as a method for the reduction. As an alternative method, the amino group of the amine derivative (1d) is protected with a protective group such as a benzyl group, then the protected secondary amino group is condensed with a carbonyl compound according to the aforementioned method, followed by alkylation and deblocking to give a monoalkylamine derivative (1e).

A dialkylamine derivative (1f) can be prepared by condensing a monoalkylamine derivative (1e) with a carbonyl compound according to the aforementioned method. In this respect, however, if the substituents $R^{13}$ and $R^{14}$ are methyl groups, an amine derivative (1d) is reacted with formaldehyde in the presence of a reducing agent in an appropriate solvent to give a desired dimethylamine derivative (1f) The reducing agents used in this reaction are desirably formic acid, sodium boron hydride and sodium cyanoboron hydride. The solvents used in this reaction are most preferably alcohols such as methanol and ethanol or acetonitrile.

-continued

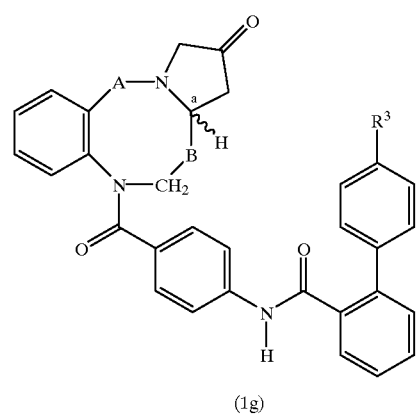

(1g)

[In these formulas, $R^3$, A, B and a are the same as those defined above].

A compound (1g) can be prepared from a compound (1a) according to the method of [Reaction Scheme 4] (oxidation reaction). The oxidation reaction can be carried out using dimethyl sulfoxide and an appropriate electrophilic activation agent in the presence or absence of a proper solvent. Examples of solvents used herein are halogenated hydrocarbons such as dichloromethane and chloroform. The amount of the dimethyl sulfoxide to be used for achieving good results ranges from equimolar amount to 100 times that of the starting compound. Examples of electrophilic activation agents used herein are N,N'-dicyclohexyl carbodiimide, acetic acid anhydride, trifluoroacetic acid anhydride, phosphorus pentachloride and oxalyl chloride The reaction is carried out at a temperature ranging from about −78° C. to the boiling point of the solvent used, preferably about −78 to 25° C. and the reaction time ranges from about 5 minutes to 48 hours, preferably about 5 minutes to 10 hours.

[Reaction Scheme 4]

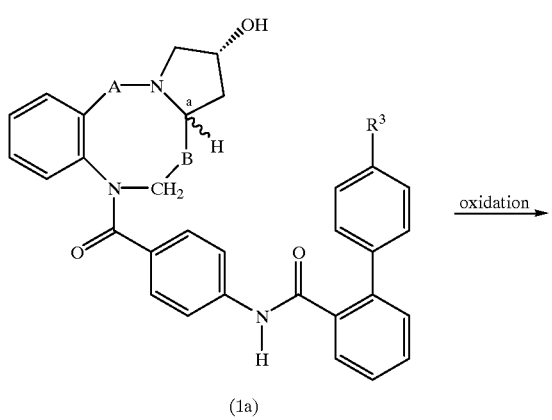

(1a)

oxidation

[Reaction Scheme 5]

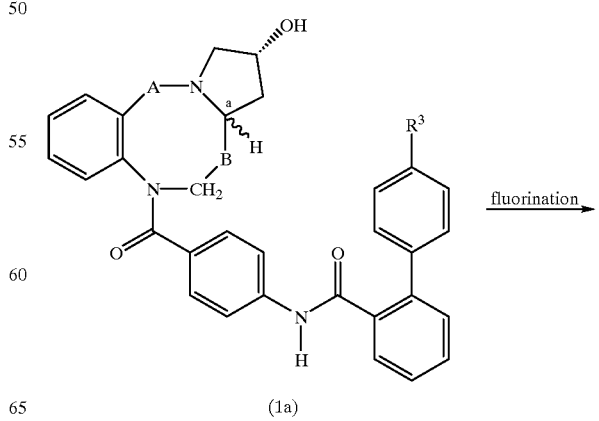

(1a)

fluorination

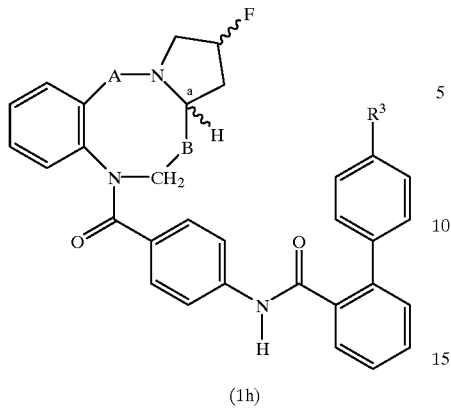

(1h)

[In these formulas, $R^3$, A, B and a are the same as those defined above].

A compound (1h) can be prepared from the corresponding compound (1a) according to the method of [Reaction Scheme 5] (fluorination reaction). An alcohol derivative (1a) can directly be fluorinated to give a desired product by reacting it with a fluorinating agent in an appropriate solvent. Examples of solvents used herein are halogenated hydrocarbons such as dichloromethane, chloroform, trichlorofluoromethane and trichloro-methane; aromatic hydrocarbons such as benzene, toluene and xylene; and ethers such as diethyl ether, tetrahydrofuran, dioxane and dimethoxy ethane. Examples of fluorinating agents herein used are diethylaminosulfur trifluoride, difluorotriphenyl phosphorane, (2-chloro-1,1,2-trifluoroethyl) diethylamine and N,N-diethyl-1,1,2,2,3,3-hexafluoropropaneamine. The amount of the fluorinating agent to be used for obtaining good results ranges from equimolar amount to 5 times the molar amount of the starting compound. The reaction temperature ranges from about −78 to 100° C., preferably about −78 to 25° C. and the reaction time ranges from about 5 to 48 hours, preferably about 5 to 18 hours. Alternatively, the hydroxyl group of the compound (1a) is treated to give an active ester such as methanesulfonic acid ester, trifluoromethanesulfonic acid ester or p-toluenesulfonic acid ester, followed by a treatment of the active ester with a fluorinating agent such as tris(dimethylamino) sulfonium difluorotrimethylsilicate or fluorinated tetrabutyl ammonium to give the corresponding compound (1h).

The tricyclic compound (2) as a starting material used in the foregoing [Reaction Scheme 1] can be prepared by the methods disclosed in literatures or any known method.

(2a)

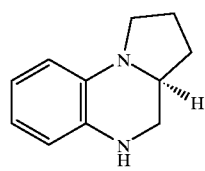

(3aS)-1,2,3,3a,4,5-Hexahydro-pyrrolo[1,2-a] quinoxaline (2a) can be prepared from 1-fluoro-2-nitrobenzene and L-proline as starting materials according to the method disclosed in Magid Abou-Gharbia, Meier E. Freed et al., J. Med. Chem., 1984, 27:1743 and U.S. Pat. No. 4,446,323. Moreover, if using D-proline, trans-4-hydroxy-L-proline, cis-4-hydroxy-D-proline, or alkyl esters thereof and hydrochloride thereof instead of the starting material L-proline according to the foregoing production method, the following compounds can be prepared: (3aR)-1,2,3,3a,4,5-hexahydro-pyrrolo[1,2-a]quinoxaline (2b); (2R,3aS)-2-hydroxy-1,2,3,3a,4,5-hexahydro-pyrrolo[1,2-a]quinoxaline (2c); and (2R,3aR)-2-hydroxy-1,2,3,3a,4,5-hexahydropyrrolo[1,2-a]quinoxaline (2d).

(2e)

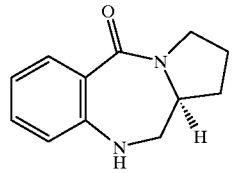

The tricyclic compounds (2e) to (2h) can be prepared by the methods A and B detailed below. (11aS)-1,2,3,10,11,11a-Hexahydro-5H-pyrrolo[2,1-c][1,4]benzodiazepin-5-one (2e) can be prepared by the method disclosed in Ahmed Kamal & N. Venugopal Rao, Chem. Commun., 385 (1996) (Method A) using L-proline methyl ester hydrochloride as a starting material. In addition, (11aS)-1,2,3,10,11,11a-hexahydro-5H-pyrrolo[2,1-c][1,4]benzodiazepin-5,11-dione can be prepared by the method disclosed in William B. Wright Jr., Herbert J. Brabander et al., J. Med. Chem., 1978, 21:1087, using L-proline and isatoic acid anhydride as starting materials. Then (11aS)-1,2,3,10,11,11a-hexahydro-5H-pyrrolo[2,1-c][1,4]benzodiazepin-5,11-dione is reduced with lithium aluminum hydride according to the method disclosed in W. Leimgruder, A. D. Batcho, F. Schenker, J. Am. Chem. Soc., 1965, 87:5793 to give the compound (2e) (Method B). Furthermore, the following compounds may be prepared using the methods A and B: (11aR)-1,2,3,10,11,11a-hexahydro-5H-pyrrolo[2,1-c][1,4]benzodiazepin-5-one (2f); (2R,11aS)-2-hydroxy-1,2,3,10,11,11a-hexahydro-5H-pyrrolo[2,1-c][1,4]benzodiazepin-5-one (2g); and (2R,11aR)-2-hydroxy-1,2,3,10,11,11a-hexahydro-5H-pyrrolo[2,1-c][1,4]benzodiazepin-5-one (2h). In this respect, however, if the starting materials used in the methods A and B carries hydroxyl groups, it is preferred to react them after protecting the group with the protective group defined above.

(2i)

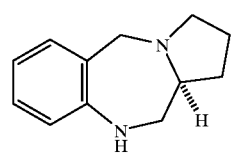

The compound (2i), (11aS)-1,2,3,10,11,11a-hexahydro-5H-pyrrolo[2,1-c][1,4]benzodiazepine may be prepared by reducing (11aS)-1,2,3,10,11,11 a-hexahydro-5H-pyrrolo[2,1-c][1,4]benzodiazepin-5,11-dione with lithium aluminum hydride according to the method disclosed in Edwin Vedejs & Namkyu Lee, J. Am. Chem. Soc., 1995,117:891 and U.S. Pat. No. 3,732,212. In this method, if using, as starting materials, (11aR)-1,2,3,10,11,11a-hexahydro-5H-pyrrolo[2,1-c][1,4]benzodiazepin-5,11-dione, (2R,11aS)-2-hydroxy-1,2,3,10,11,11a-hexahydro-5H-pyrrolo[2,1-c][1,4]benzodiazepin-5,11-dione and (2R,11aR)-2-hydroxy-1,2,3,10,11,11a-hexahydro-5H-pyrrolo[2,1-c][1,4]benzodiazepin-5,11-dione, the following compounds can be prepared: (11aR)-1,2,3,10,11,11a-hexahydro-5H-pyrrolo[2,1-c][1,4]benzodiazepine (2j), (2R,11aS)-2-hydroxy-1,2,3,10,11,11a- hexahydro-5H-pyrrolo[2,1-c][1,4]benzodiazepine (2k) and (2R,11aR)-2-hydroxy-1,2,3,10,11,11a-hexahydro-5H-pyrrolo[2,1-c][1,4]benzodiazepine (2l).

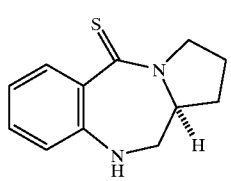

(2m)

The compound (2m), (11aS)-1,2,3,10,11,11a-hexahydro-5H-pyrrolo[2,1-c][1,4]benzodiazepin-5-thione (2m) can be prepared by converting (11aS)-1,2,3,10,11,11a-hexahydro-5H-pyrrolo[2,1-c][1,4]benzodiazepin-5-one (2e) into its thionyl derivative using phosphorus pentasulfide or Lawesson's reagent. The compounds (11aR)-1,2,3,10,11,11a-hexahydro-5H-pyrrolo[2,1-c][1,4]benzodiazepin-5-one (2f), (2R,11aS)-2-hydroxy-1,2,3,10,11,11a-hexahydro-5H-pyrrolo[2,1-c][1,4]benzodiazepin-5-one (2g) and (2R,11aR)-2-hydroxy-1,2,3,10,11,11a-hexahydro-5H-pyrrolo[2,1-c][1,4]benzodiazepin-5-one (2h) may likewise be converted into their thionyl derivatives to thus give the corresponding compounds (11aR)-1,2,3,10,11,11a-hexahydro-5H-pyrrolo[2,1-c][1,4]benzodiazepin-5-thione (2n), (2R,11aS)-2-hydroxy-1,2,3,10,11,11a-hexahydro-5H-pyrrolo[2,1-c][1,4]benzodiazepin-5-thione (2o) and (2R,11aR)-2-hydroxy-1,2,3,10,11,11a-hexahydro-5H-pyrrolo[2,1-c][1,4]benzodiazepin-5-thione (2p).

[Reaction Scheme 6]

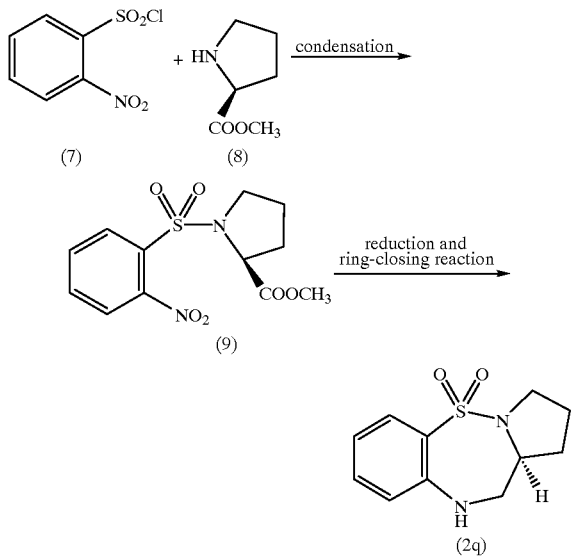

A method for preparing the compound (2q): (11aR)-1,2,3,10,11,11a-hexahydro-pyrrolo[1,2-b][1,2,5]benzothiadiazepin-5,5-dioxide (2q) is shown in [Reaction Scheme 6]. More specifically, 2-nitrobenzenesulfonyl chloride (7) is reacted with L-proline methyl ester (8) or the hydrochloride thereof in the presence of a base to give the compound (9) The compound (9) is then reduced to the aldehyde (10) using a metal hydride such as diisobutyl aluminum hydride, sodium bis(2-methoxyethoxy) aluminum hydride or sodium aluminum hydride, followed by reduction of the nitro group into an amino group and ring closure in one step through hydrogenation using palladium-carbon to give (11aR)-1,2,3,10,11,11a-hexahydro-pyrrolo[1,2-b][1,2,5]benzothiadiazepin-5,5-dioxide (2q).

[Reaction Scheme 7]

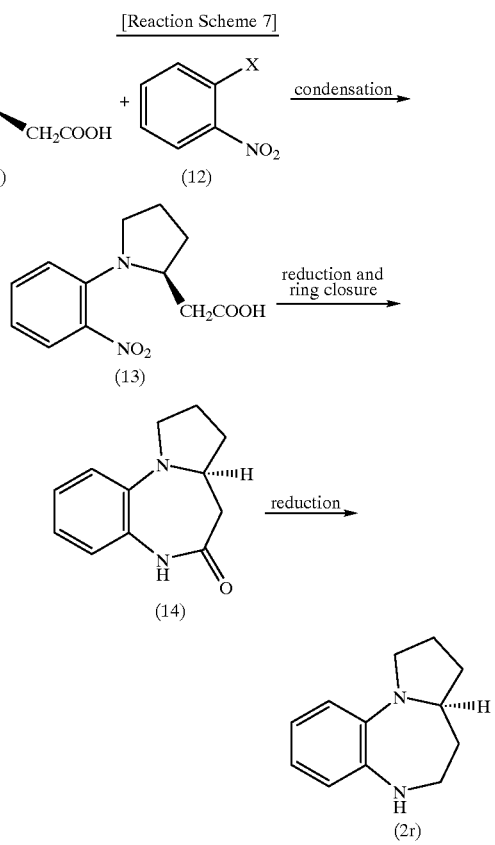

[In these formulas, X represents a halogen atom].

The compound (2r), (3aS)-2,3,3a,4,5,6-hexahydro-1H-pyrrolo[1,2-a][1,5]benzodiazepine, can be prepared by the method of [Reaction Scheme 7]. The starting material of [Reaction Scheme 7], (2S)-pyrrolidinyl acetic acid (11), can be prepared from L-proline as a starting material according to the method disclosed in R. Busson & H. Vanderhaeghe, J. Org. Chem., 1978, 43:4438. More specifically, a 1-halogeno-2-nitrobenzene (12) can be reacted with (2S)-pyrrolidinyl acetic acid (11) in the presence of a base to give the compound (13), followed by reduction of the nitro group into an amino group and ring closure in one step through hydrogenation using palladium-carbon to give the lactam (14). The tricyclic compound (2r) can simply be prepared by reducing the lactam (14) using, for instance, lithium aluminum hydride, lithium boron hydride or diborane. If using D-proline, trans-4-hydroxy-L-proline, cis-4-hydroxy-D-proline and hydrochloride thereof, as starting materials, the following compound can be prepared according to the same procedures: (3aR)-2,3,3a,4,5,6-hexahydro-1H-pyrrolo(1,2-a][1,5]benzodiazepine (2s); (2R,3aS)-2-hydroxy-2,3,3a,4,5,6-hexahydro-1H-pyrrolo[1,2-a][1,5]benzodiazepine (2t); and (2R,3aR)-2-hydroxy-2,3,3a,4,5,6-hexahydro-1H-pyrrolo[1,2-a][1,5]benzodiazepine (2u). In this respect, however, if the starting material carries a hydroxyl group, the foregoing reaction is preferably carried out after protecting the same with the foregoing protective group.

Tricyclic compounds (2c, 2d, 2g, 2h, 2k, 2l, 2o, 2p, 2t, 2u) obtained from trans-4-hydroxy-L-proline and cis-4-hydroxy-D-proline as starting materials can be treated according to the same procedures used in [Reaction Scheme 2] and [Reaction Scheme 3] to give tricyclic compounds having hydroxyl group, amino group or mono- or dialkylamino group, whose steric configuration is reversed, such as (2S, 3aS)-2-hydroxy-1,2,3,3a,4,5-hexahydro-pyrrolo[1,2-a] quinoxaline (2v); (2S, 3aR)-2-hydroxy-1,2,3,3a,4,5-hexahydro-pyrrolo[1,2-a]quinoxaline (2x); (2S, 3aS)-2-amino-1,2,3,3a,4,5-hexahydro-pyrrolo[1,2-a]quinoxaline (2y); (2S, 3aR)-2-amino-1,2,3,3a,4,5-hexahydro-pyrrolo[1,2-a]quinoxaline (2z); (2S, 3aS)-2-(N,N-dimethylamino)-1,2,3,3a,4,5-hexahydro-pyrrolo[1,2-a]quinoxaline (2aa); (2S, 3aR)-2-(N,N-dimethylamino)-1,2,3,3a,4,5-hexahydro-pyrrolo[1,2-a]quinoxaline (2ab); (2S, 11aS)-2-hydroxy-1,2,3,10,11,11a-hexahydro-5H-pyrrolo[2,1-c][1,4]benzodiazepin-5-one (2ac); (2S, 11aR)-2-hydroxy-1,2,3,10,11,11a-hexahydro-5H-pyrrolo[2,1- c][1,4]benzodiazepin-5-one (2ad); (2S, 11aS)-2-amino-1,2,3,10,11,11a-hexahydro-5H-pyrrolo[2,1-c][1,4]benzo-diazepin-5-one (2ae); (2S, 11aR)-2-amino-1,2,3,10,11,11a-hexahydro-5H-pyrrolo[2,1-c][1,4]benzodiazepin-5-one (2af); (2S, 11aS)-2-(N,N-dimethyl-amino)-1,2,3,10,11,11a-hexahydro-5H-pyrrolo[2,1-c][1,4]benzodiazepin-5-one (2ag); (2S, 11aR)-2-(N,N-dimethylamino)-1,2,3,10,11,11a-hexahydro-5H-pyrrolo[2,1-c][1,4]benzodiazepin-5-one (2ah); (2S, 11aS)-2-hydroxy-1,2,3,10,11,11a-hexahydro-5H-pyrrolo[2,1-c][1,4]benzodiazepine (2ai); (2S, 11aR)-2-hydroxy-1,2,3,10,11,11a-hexahydro-5H-pyrrolo[2,1-cl[1,4]benzodiazepine (2aj); (2S, 11aS)-2-amino-1,2,3,10,11,11a-hexahydro-5H-pyrrolo[2,1-c][1,4]benzodiazepine (2ak); (2S, 11aR)-2-amino-1,2,3,10,11,11a-hexahydro-5H-pyrrolo[2,1-c][1,4] benzodiazepine (2al); (2S, 11aS)-2-(N,N-dimethylamino)-1,2,3,10,11,11a-hexahydro-5H-pyrrolo[2,1-c][1,4]benzodiazepine (2am); (2S, 11aR)-2-(N,N-dimethylamino)-1,2,3,10,11,11a-hexahydro-5H-pyrrolo[2,1-c][1,4] benzodiazepine (2an); (2S, 3aS)-2-hydroxy-2,3,3a,4,5,6-heptahydro-1H-pyrrolo[1,2-a][1,5]benzodiazepine (2ao); (2S, 3aR)-2-hydroxy-2,3,3a,4,5,6-heptahydro-1H-pyrrolo[1,2-a][1,5]benzodiazepine (2ap); (2S, 3aS)-2-amino-2,3,3a,4,5,6-heptahydro-1H-pyrrolo[1,2-a][1,5]benzodiazepine (2aq); (2S, 3aR)-2-amino-2,3,3a,4,5,6-heptahydro-1H-pyrrolo[1,2-a][1,5]benzodiazepine (2ar); (2S, 3aS)-2-(N,N-dimethylamino)-2,3,3a,4,5,6-heptahydro-1H-pyrrolo[1,2-a][1,5]benzodiazepine (2as); (2S, 3aR)-2-(N,N-dimethylamino)-2,3,3a,4,5,6-heptahydro-1H-pyrrolo[1,2-a][1,5]benzodiazepine (2at). Moreover, intermediates, through which the tricyclic compounds (2c, 2d, 2g, 2h, 2k, 2l, 2o, 2p, 2t, 2u) each carrying a hydroxyl group are prepared, can be used in the same procedures employed in [Reaction Scheme 2] and Reaction Scheme 3] to convert them into compounds carrying hydroxyl group, amino group or mono- or dialkylamino group, whose steric configuration is reversed. The compounds thus prepared may be used in the methods disclosed in the foregoing literatures or in any known method to give tricyclic compounds (for instance, 2v to 2at).

The reaction products prepared by the foregoing preparation methods are isolated and purified in the form of free compounds, salts thereof, hydrates thereof or various solvates thereof. These salts may be prepared by subjecting them to the usual salt-forming reaction.

The isolation and purification of these compounds may be performed using the usual chemical operations such as extraction, concentration, distillation, crystallization, filtration, recrystallization, and various chromatography techniques.

The compound of the present invention is often present in the form of an isomer, which comprises a racemate, an optically active substance or a diastereomer, or mixture thereof The racemic compound may be divided into the optically pure isomers by the commonly used racemate-resolution method [such as a method comprising forming a diastereomer salt with an optically active acid (such as tartaric acid) to thus optically resolve the racemate]. In addition, a diastereomer mixture may be resolved by the usual method such as the fractional crystallization or chromatography.

As will be demonstrated in the following Test Examples, the compounds of the present invention have stronger vasopressin V2 receptor antagonism as compared with OPC-31260, which is in the process of development as a vasopressin V2 receptor antagonist. Moreover, they possess diurese substantially higher than those observed for Furosemide and OPC-31260. In addition, the diurese of the compounds of the present invention is found to be water diurese. Therefore, the compounds can be used sail as aquaresis free of any side effects such as hypokalemia and hyponatremia. For this reason, it is also an object of the present invention to provide a diuretic drug comprising the compound of the present invention as an effective component.

The compounds of the present invention would be expected as vasopressin receptor antagonists. However, they are novel compounds and therefore, there would be high possibility that they can be used in other medical applications in addition to the use as a vasopressin receptor antagonist. Accordingly, it is a still another object of the present invention to provide drug compositions comprising the compounds of the present invention or pharmaceutically acceptable salts thereof in combination with pharmaceutically acceptable carriers.

The compounds that correspond to the compounds of the present invention each having a terminal substituent (such as tolyl) other than biphenyl never show marked vasopressin receptor antagonism and diurese, Consequently, it is one of the characteristic properties, concerning the chemical structure, of the compounds of the present invention to have a biphenyl group at the terminal.

J.P. KOKAI No. Hei 7-157486 discloses a compound having a tricyclic diazepine ring. However, this tricyclic diazepine ring comprises one or two nitrogen atom-containing hetero rings in which an aromatic 5-membered ring (unsaturated) is fused. On the other hand, the tricyclic hetero ring of the compound of the present invention comprises a pyrrolidine ring (saturated) as a constituent. Accordingly, it is one of the chemical structural and pharmacological characteristic properties of the compounds of the present invention to have a tricyclic hetero ring carrying an asymmetric carbon atom due to the presence of an adjacent pyrrolidine ring.

The absolute configuration of the position a is preferably R, in case where A and B in the general formula (1) are, for instance, single bonds; and the absolute configuration of the position a is preferably S, in case where A is —CO— and B is a single bond in Formula (1), in order to ensure good vasopressin receptor antagonism and diurese of the compounds of the present invention.

When the compound of the present invention is used as a medicine, the compound may be administered, to animals including human, as such or a drug composition containing the compound in an amount ranging from 0.1 to 99.5%, preferably 0.5 to 90% together with a pharmaceutically acceptable, nontoxic and inert carrier.

Examples of carriers used in the drug composition of the present invention are solid, semi-solid or liquid diluents, fillers and other auxiliary agents for pharmaceutical preparations, which may be used alone or in any combination. The drug composition is desirably administered in the form of unit dosage form. The drug composition of the present invention can be administered through oral, intravenous or rectum routes. Of course, the drug composition is administered in the dosage form suitable for each administration route. Among these, oral administration is particularly preferred.

The dose of the compound of Formula (1) or a salt thereof to be incorporated into the vasopressin receptor antagonist of the present invention is desirably determined while taking into consideration the conditions of patients such as ages and body weights, routes of administration, symptoms and degree of severeness of each disease, but in general ranges from 5 to 1500 mg/human/day, preferably 10 to 300 mg/human/day for adult and for oral administration, as expressed in terms of the amount of the effective component. Alternatively, if the drug composition is administered intravenously, the amount of the effective component in general ranges from 0.1 to 1000 mg/human/day, preferably 1 to 600 mg/human/day. The drug composition is sometimes sufficiently effective even if it is used in a smaller amount, and it is often required to use the effective component in a greater amount. The drug composition may be administered in a divided dose for 2 to 4 times per day.

The drug composition can be orally administered in the form of unit doses such as powdered drugs, powders, tablets, sugar-coated tablets, capsules, granules, suspensions, liquid preparations, syrups, drops, sublingual tablets and others. The powdered drug may be prepared by finely pulverizing the effective substance to a desired particle size. The powder can be prepared by finely pulverizing the effective component to desired fineness and then admixing the same with a carrier for drugs, for instance, edible hydrocarbons such as starch and mannitol or the like, which is likewise finely pulverized. The drug composition may optionally comprise other additives such as flavors, preservatives, dispersing agents, coloring agents and perfumes.

The capsule can be prepared by encapsulating, into outer covers such as gelatin capsules, a powdered drug or powder formed by the foregoing method or those formed into granules as will be detailed below in connection with the tablets. It is also possible to encapsulate these powdery or granular components into capsules after admixed with a lubricant and/or a fluidizing agent such as colloidal silica, talc, magnesium stearate, potassium stearate or solid polyethylene glycol. The efficacy of the drug upon ingestion of the capsule can be improved by incorporating, into the capsule, a disintegrating agent and/or a solubilizing agent such as carboxymethyl cellulose, calcium carboxymethyl cellulose, hydroxypropyl cellulose having a low degree of substitution, sodium closcarmerose, sodium carboxystarch, calcium carbonate, sodium carbonate.

Alternatively, it is also possible to suspend or disperse fine powder of the compound of the present invention in a vegetable oil, polyethylene glycol, glycerin, a surfactant, followed by wrapping the resulting dispersion with a gelatin sheet to thus give soft capsules. The tablet may be prepared by forming a powdery mixture, then converting the mixture into granules or slugs, adding a disintegrating agent or a lubricant thereto and finally compressing the mixture. Mixing appropriately pulverized substances with the foregoing diluents or base materials may produce the powdery mixture. The powdery mixture may optionally comprise, for instance, a binder (such as sodium carboxymethyl cellulose, hydroxypropylmethyl cellulose, methyl cellulose, hydroxypropylmethyl cellulose, gelatin, polyvinyl pyrrolidone, polyvinyl alcohol), a solubilization-retarding agent (such as paraffin, waxes, hardened castor oil), a reabsorbing agent (such as quaternary salts), an adsorbing agent (such as bentonite, kaolin, dicalcium phosphate). The powdery mixture can first be moistened with a binder such as syrup, starch glue, gum arabic, a cellulose solution or a polymer solution and then forced to pass through a sieve to give granular particles. Alternatively, it is also possible to first treat in a tableting machine, followed by pulverization of the resulting slugs having incomplete shapes to give granules.

Addition of a lubricant such as stearic acid, stearic acid salts, talc or a mineral oil to the granules thus produced permits the prevention of any formation of agglomerates. The mixture thus lubricated is then subjected to tableting operations. The crude tablets thus prepared may be subjected to film coating or sugar coating treatments. Alternatively, the drug may be mixed with an inert carrier having flowability and then directly compressed without being passed through, for instance, granulation and/or slug-forming processes. In this respect, it is also possible to use, for instance, a transparent or translucent protective film consisting of a closed film of shellac, a film of sugar or a polymer material and a lustering film of wax.

Other orally administered dosage forms such as solutions, syrups and elixirs may likewise be formed into unit dosage forms so that each unit dose comprises a predetermined amount of the drug. Dissolving a desired compound in a solution containing a perfume produces the syrup and the elixir is prepared using a non-toxic alcoholic carrier. The suspension can be formulated by dispersing a desired compound in a non-toxic carrier. These drug compositions may, if necessary, comprise a solubilizing agent or an emulsifying agent (such as ethoxylated isostearyl alcohols, polyoxyethylene sorbitol esters), preservatives, taste-improving agents (such as peppermint oil, saccharin).

The unit dosage preparations for oral administration may, if necessary, be encapsulated into microcapsules. The preparations may be coated or embedded in a polymer-wax or the like to extend the effective time thereof or to impart sustained release properties to the drug. The drug composition of the present invention can be administered within tissues by formulating it into a liquid unit dosage form for subcutaneous, intramuscular or intravenous injection such as a solution or a suspension. These dosage forms are prepared by suspending or dissolving a constant amount of each compound in a non-toxic liquid carrier suitably used for injections such as aqueous or oily mediums and then sterilizing the resulting suspension or solution. Alternatively, a constant amount of each compound is dispensed into a vial, then the vial and the contents thereof are sterilized and the vial is finally sealed. It is also possible to provide a powdered or lyophilized effective component together with preparatory vials and carriers to dissolve or mix the component therewith immediately before the practical administration. A non-toxic salt or a salt solution may be added to these injections to ensure the isotonization thereof. Moreover, other additives such as a stabilizer, a preservative or an emulsifying agent may likewise be used in these injections.

The drug of the present invention can be administered through rectum using the drug in the form of a suppository which can be prepared by mixing a desired compound with water-soluble or water-insoluble solid having a low melting point such as polyethylene glycol, cacao butter, higher esters (such as myristyl ester of palmitic acid) or mixture thereof The present invention will be described in more detail with reference to the following Test Examples, Reference Examples, Examples and preparation Examples, but the present invention is not restricted to these specific Examples at all.

TEST EXAMPLE 1

Binding Study of Vasopressin ($V_1$) Receptor

The livers excised from Sprague-Dawley female rats were cut into small pieces, and were homogenized in 50 mM Tris-HCl, pH 7.4 hereunder referred to as "buffer"). The homogenate was centrifuged at 50000×g, at 4° C. for 20 minutes. The pellet was added the buffer in an amount of 10 times the volume of the pellet, the mixture was recentrifuged by the same method as described above to wash the residue. The buffer was further added to the resulting pellet so that the protein content thereof was adjusted to 10 mg/ml to thus give a crude membrane fraction of rat liver. The crude membrane fraction of rat liver was used in the following test. More specifically, 5000 µg of the crude liver membrane was incubated with [$^3$H]-Arg-vasopressin V-1 antagonist ([$^3$H] vasopressin V1 antagonist: 2 nM) and various concentration ($3\times10^{-12}$ to $10^{-6}$) of the test compounds in a 1000 µL of buffer containing 10 mM magnesium chloride, 10 mM potassium chloride and 0.1% bovine serum albumin at 25° C. for 60 minutes. Thereafter the incubation mixture was rapidly filtered by vacuum using a cell harvester. The filters were washed with buffer to remove free ligands and excess buffer, and to thus trap labeled ligand linked with the receptor on the filter paper. The filter paper was sufficiently dried and mixed with a liquid scintillator, and the amount of the [$^3$H] vasopressin V1 antagonist bonded to the membrane was determined using a liquid scintillation counter. The inhibition rate at each concentration was calculated according to the following equation:

Inhibition Rate (%)=100−[(B−N)/($B_0$−N)]×100

Wherein B represents the amount of the [$^3$H] vasopressin V1 antagonist bonded to the membrane in the presence of known amounts of the compound to be tested and the [$^3$CH] vasopressin V1 antagonist;

$B_0$ represents the amount of the [$^3$H] vasopressin V1 antagonist bonded to the membrane in the absence of the compound to be tested;

N represents the amount of the [$^3$H] vasopressin V1 antagonist bonded to the membrane in the presence of an excess of vasopressin ($10^{-6}$M).

For the compound whose inhibition rate was determined at a concentration ranging from $3\times10^{-12}$ to $10^{-6}$M, a concentration-response curve was obtained from the inhibition rate at every concentrations. The $IC_{50}$ value (the concentration required to cause 50% inhibition of the specific binding of [$^3$H]-$V_1$ antagonist) was determined. 50% inhibition of the association of the tracer and the receptor). On the other hand, for the compounds which were investigated only one concentration ($10^{-7}$ M), the inhibition rate at that concentration was defined to be the binding rate. The results thus obtained are summarized in the following Tables 1 and 2.

TEST EXAMPLE 2

Binding Study of Vasopressin ($V_2$) Receptor

The kidneys excised from Sprague-Dawley female rats were cut into small pieces, and were homogenized in 50 mM Tris-HCl, pH 7.4 (hereunder referred to as "buffer"). The homogenate was centrifuged at 50000×g, at 4° C. for 20 minutes. The pellet was added the buffer in an amount of 10 times the volume of the pellet, the mixture was recentrifuged by the same method as described above to thus wash the residue. The buffer was further added to the resulting pellet so that the protein content thereof was adjusted to 10 mg/ml to thus give a crude membrane fraction of rat kidney. The crude membrane fraction of rat kidney was used in the following test. More specifically, 5000 µg of the crude kidney membrane was incubated with [$^3$H]-Arg-vasopressin V-2 antagonist ([$^3$H] vasopressin V2 antagonist: 2 nM) and various concentration ($3\times10^{-12}$ to $10^{-6}$H) in a 1000 µL buffer containing 1 mM magnesium chloride, 2 mM potassium chloride and 0.1% bovine serum albumin at 25° C. for 60 minutes. Thereafter the incubation mixture was rapidly filtered by vacuum using a cell harvester. The filters were washed with buffer to remove free ligands and excess buffer and to thus trap labeled ligand linked with the receptor on the filter paper. The filter paper was sufficiently dried and mixed with a liquid scintillator. The amount of the [$^3$H] vasopressin V2 antagonist bonded to the membrane was determined using a liquid scintillation counter. The $IC_{50}$ value and the binding rate was determined by the same method described in Test Example 1. The results thus obtained are summarized in the following Tables 1 and 2.

In addition, the affinity of comparative Examples 1 and 2, as control compound, for vasopressin $V_2$ acceptor were determined using the same method of the procedure of Test Examples 1 and 2. The results thus obtained are summarized in the following Tables 1 and 2.

The results listed in Tables 1 and 2 indicate that the compound of the present invention possesses vasopressin V2 receptor antagonism considerably stronger than that observed for the compound of Comparative Example 2.

COMPOUND OF COMPARATIVE EXAMPLE 1

(OPC-21268: the Compound Prepared in Example 141 of EP0382185)

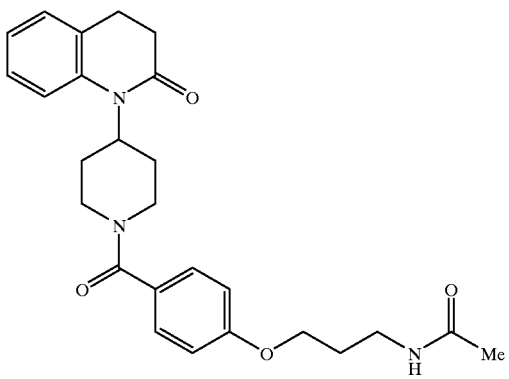

COMPOUND OF COMPARATIVE EXAMPLE 2

(OPC-31260: the Compound (hydrochloride) Prepared in Example 408 of P.I.A. No. WO91/05549)

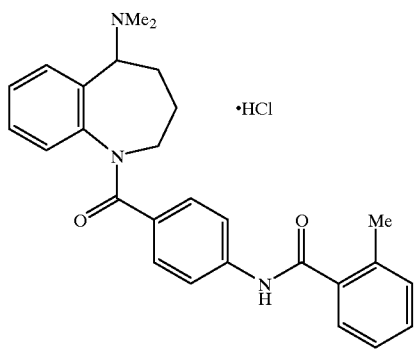

TABLE 1

Binding Rate of Vasopressin V1 and V2 Receptors

| Test Compound (Ex. No.) | Binding Rate of Vasopressin V1 Receptor ($10^{-7}$M, %) | Binding Rate of Vasopressin V2 Receptor ($10^{-7}$M, %) |
| --- | --- | --- |
| 8 | 16.3 | 100 |
| 11 | 34.0 | 100 |
| 16 | 68.2 | 100 |
| 17 | 52.4 | 100 |
| 18 | 58.3 | 100 |
| 21 | 19.5 | 100 |
| 22 | 33.5 | 100 |
| 24 | 16.5 | 100 |
| 25 | 4.1 | 100 |
| 26 | 4.0 | 100 |
| 29 | 18.9 | 99.5 |
| 37 | 2.8 | 100 |
| 38 | 4.7 | 100 |
| 41 | 6.6 | 92.0 |
| 43 | 61.6 | 100 |
| 44 | 48.2 | 96.7 |
| 47 | 59.8 | 91.9 |
| 48 | 42.3 | 96.8 |
| 49 | 88.3 | 92.8 |
| 50 | 92.4 | 97.8 |
| 52 | 95.7 | 100 |
| 53 | 63.8 | 97.9 |
| 54 | 98.6 | 95.1 |
| Comp. Ex. 1 | 13.8 | 32.4 |
| Comp. Ex. 2 | 3.4 | 91.2 |

TABLE 2

Binding Affinity for Vasopressin V1 and V2 Receptors

| Test Compound (Ex. No.) | Affinity for Vasopressin V1 Receptor, $IC_{50}$ ($\mu$M) | Affinity for Vasopressin V2 Receptor, $IC_{50}$ ($\mu$M) |
| --- | --- | --- |
| 18 | 0.066 | 0.00018 |
| 25 | >1 | 0.0016 |
| 47 | 0.062 | 0.00077 |
| Comp. Ex. 1 | 0.79 | >1 |
| Comp. Ex. 2 | >1 | 0.0077 |

TEST EXAMPLE 3

Aquaretic Effects in Normal Conscious Rat

Studies were performed with Sprague-Dawley male SPF rats (body weight: 240 to 320 g; 8-week-old). In this experiment, each group consisted of not less than 4 animals and rats were fasted over 16 to 20 hours. The animals were acclimatized in metabolic cages for one hour, then each compound to be tested was dissolved in 100% N,N-dimethylformamide or suspended in 5% gum arabic solution and administered to these animals intravenously (iv.) in a dose of 3 mg/kg or orally (p.o.) in a dose of 30 mg/kg. Immediately after the test compound or vehicle were orally administered, saline (25 ml/kg) was given orally. Spontaneous voided urines were collected for 4 hours after the administration of the compound and the amount of the urine were determined. In this case, the control group consisted of animals to which only 5% gum arabic was orally administered.

In addition, known compounds of Comparative Examples 2 and Comparative Examples 3 and 4 represented by the following formulas were used as control compounds. The results obtained are summarized in the following Table 3.

COMPOUND OF COMPARATIVE EXAMPLE 3

(Furosemide)

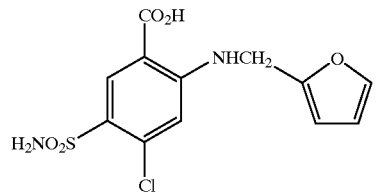

COMPOUND OF COMPARATIVE EXAMPLE 4

(the compound of Example 3 of J.P. KOKAI No. Hei 7-157486)

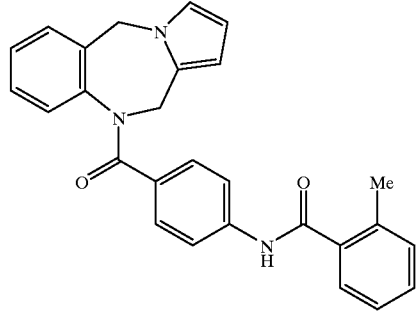

Figure 2:
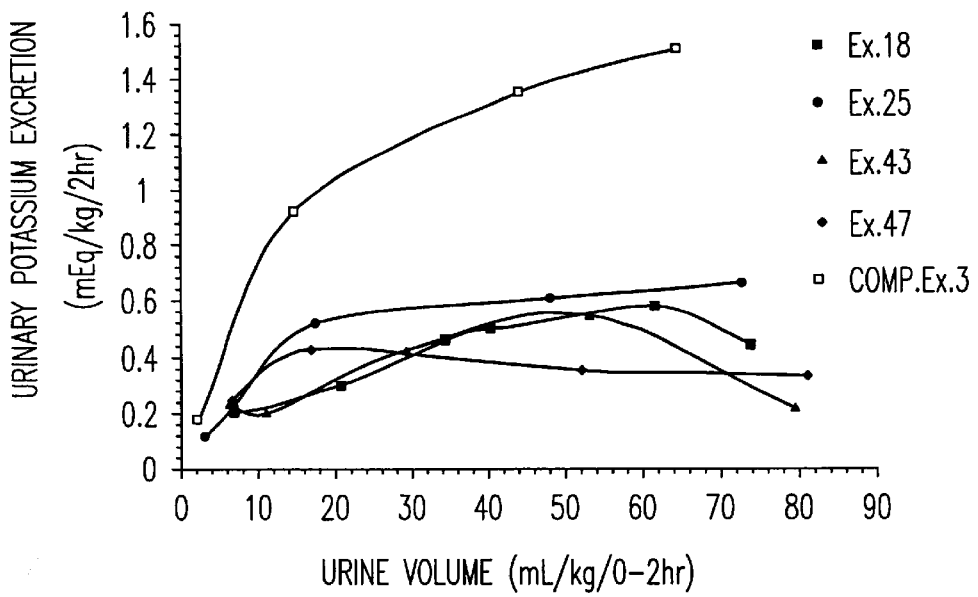
FIG. 2 shows the relations between the urine volume and the urinary potassium excretion.
Figure 3:
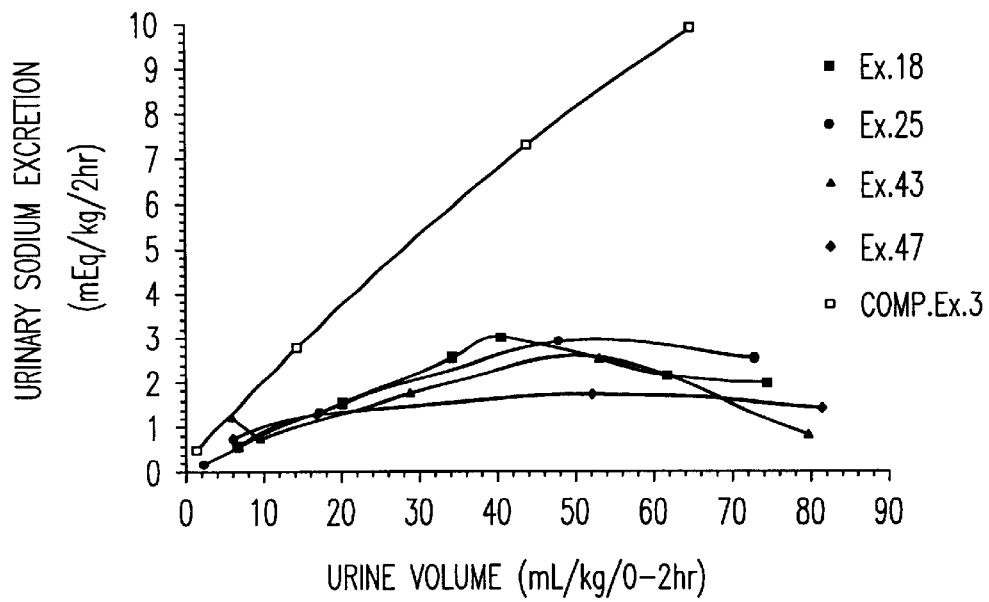
FIG. 3 shows the relations between the urine volume and the urinary chlorine excretion
Figure 4:
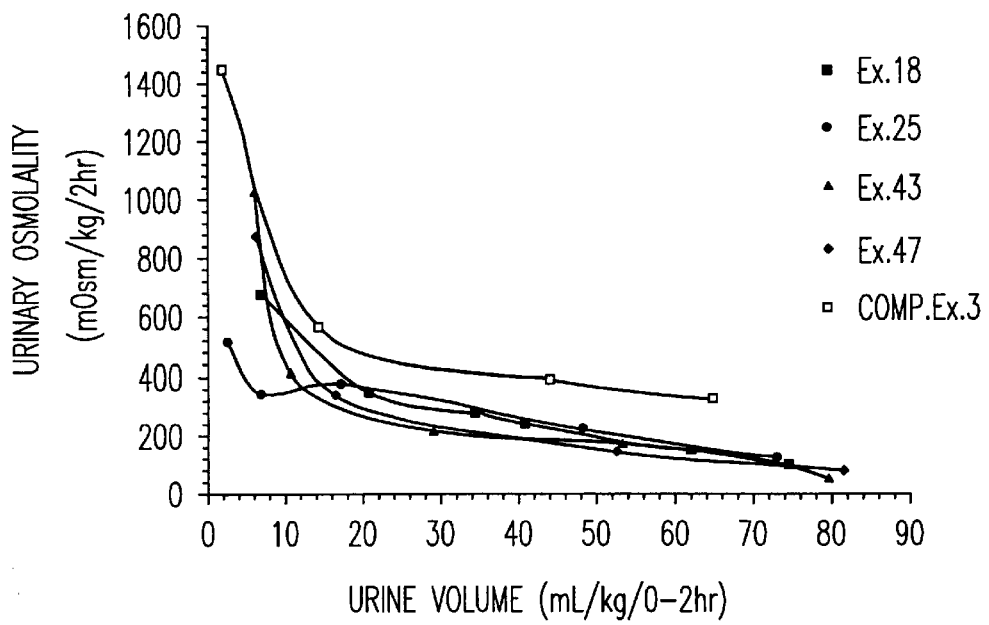
FIG. 4 shows the relations between the urine volume and the urinary osmolality.

Separately, the cumulative urine in each animal was collected for 2 hours after the administration of the compound, and analyze the amounts of sodium and potassium as electrolytes present in the urine (ion-selective electrode method), the amount of chlorine (coulometric titration) and urinary osmotic pressure (cryoscopic method). The results thus observed for typical compounds of the present invention are plotted on the accompanying drawings (FIGS. 1, 2, 3 and 4). FIGS. 1, 2 and 3 each shows the relation between the amount of urine accumulated over 2 hours (X axis), which is converted into the amount/kg body weight of the animal and observed at each dose and the amount of electrolytes present in the urine (Y axis), while FIG. 4 shows the relation between the amount of urine (X axis) and the urinary osmotic pressure (Y axis). In this test, each compound tested was used in the following dose. The compound of Comparative Example 3 was used as a control compound.

Dose of the compound prepared in Example 18 (0, 0.3, 1, 3, 10, 30 mg/kg);

Dose of the compound prepared in Example 25 (0, 0.3, 1, 3, 30 mg/kg);

Dose of the compound prepared in Example 43 (0, 0.3, 1, 3, 30 mg/kg);

Dose of the compound prepared in Example 47 (0, 0.3, 3, 30 mg/kg);

Dose of the compound of Comparative Example 3 (0, 10, 30, 100 mg/kg);

For the control group to which the compound of Comparative Example 3 was administered, it was observed that the amount of electrolytes excreted in the urine and the urinary osmotic pressure were increased approximately in proportion to the increase in the amount of the urine. On the other hand, the compounds of the present invention considerably decreased the amount of electrolytes excreted in the urine as compared with that observed for the compound of Comparative Example 3 and reduced the urinary osmotic pressure, although the former possessed strong diuresis. The foregoing results clearly indicate that the compound of the present invention possesses aquaresis or that the compound selectively excretes water, unlike the conventional diuretics.

TABLE 2

Diuresis in conscious Rats

| Test Compound (Ex. No.) | Amount of Urine Volume (ml/kg/0–4 hr.) | |
|---|---|---|
| | Dose, 3 mg/kg, i.v. | Dose, 30 mg/kg, p.o. |
| Control | 12.5 | 6.9 |
| Comp. Ex. 2 | 22.9 | 79.1 |
| Comp. Ex. 3 | 27.3 | 59.9 |
| Comp. Ex. 4 | 34.8 | 22.6 |
| 1 | 33.1 | 40.3 |
| 3 | 29.5 | 54.0 |
| 7 | 29.3 | 33.8 |
| 10 | 22.2 | 39.6 |
| 11 | 56.5 | 69.6 |
| 12 | 66.0 | 12.8 |
| 13 | 55.6 | 82.0 |
| 14 | 60.6 | 90.3 |
| 16 | 71.0 | 72.0 |
| 17 | 58.6 | 26.3 |
| 18 | 79.2 | 96.3 |
| 21 | 47.6 | 81.4 |
| 22 | 58.8 | 79.6 |
| 23 | 27.2 | 35.6 |
| 24 | 49.4 | 46.1 |
| 25 | 58.5 | 102.7 |
| 26 | 72.3 | 88.3 |
| 29 | 50.4 | 14.0 |
| 30 | 57.1 | 103.0 |
| 37 | 40.7 | 21.1 |
| 38 | 60.0 | 66.6 |
| 41 | 29.6 | 73.8 |
| 43 | 77.5 | 121.6 |
| 44 | 73.0 | 92.8 |
| 45 | 51.4 | 93.9 |
| 46 | 82.5 | 118.8 |
| 47 | 79.5 | 109.6 |
| 48 | 78.9 | 14.8 |
| 49 | 76.5 | 43.8 |
| 50 | 60.0 | 36.0 |
| 51 | 63.8 | 21.7 |
| 52 | 60.6 | 36.6 |
| 54 | 78.3 | 68.0 |
| 56 | 87.4 | 116.4 |

TEST EXAMPLE 4

Effect of Compound of the Invention in Hepatocirrhosis Model

This experiment was performed according to the method disclosed in Tsuboi et al. (Kidney International, 1994) 46:237–244). A 1:1 mixture of carbon tetrachloride and olive oil was subcutaneously administered to the dorsum of each Wistar male rat in an amount of 4 mg/kg once a week for 13 weeks to thus establish a rat model of hepatocirrhosis. Separately, only olive oil was administered to control rats. The hepatocirrhosis rats were divided into 5 groups (6 to 8 animals per group) and 5% gum arabic, the compounds of Examples 18, 25 and 30 and Comparative Example 3 were administered to these groups, respectively. Moreover, 5% gum arabic was administered to the control group (5 animals). These animals were acclimatized in a metabolic cage for 2 hours under giving feed and water ad libitus followed by oral administration of 10 mg/kg of the compound of Example 18, 25 or 30; or 30 mg/kg of the compound of Comparative Example 3, which was suspended in 5% gum arabic (2 ml/kg each). 20 minutes after the each compound or 5% gun arabic were orally administered to rats, water (30 mL/kg) was given orally. Spontaneous voided urine were collected for 4 hours after the administration of the drug and urine volume were determine. After 20 minutes from the collection of the urine, the rats were subjected to abdominal section under ether-anesthetization and the ascites thereof was absorbed in absorbent cotton to determine the wet weight of the cotton, followed by determination of the amount of the ascites (g) based on the difference in weight between the wet cotton and the dry cotton prior to the absorption of the ascites.

Figure 5:
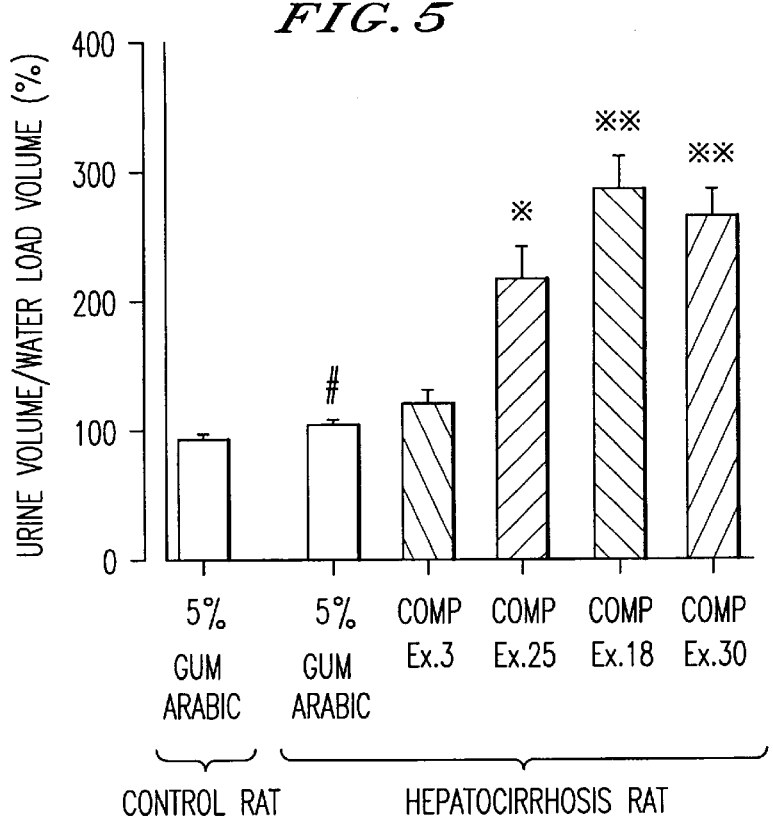
FIG. 5 shows the diuretic effect (the percentage of water load) of the compounds in a hepatocirrhosis model.
Figure 6:
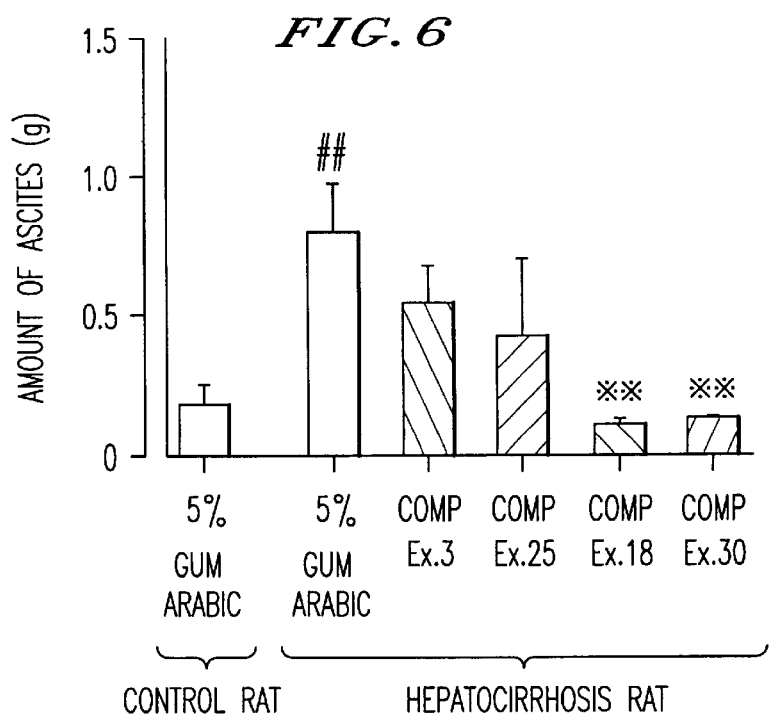
FIG. 6 shows the inhibitory effect of the compounds or the ascites volume in a hepatocirrhosis model.

These results are shown in FIGS. 5 and 6. In FIGS. 5 and 6, each numerical value was expressed in terms of the average of 5 to 8 measurements (±standard error).

In these figures, * and * * mean the significant difference relative to the 5% gum arabic-administered hepatocirrhosis rat group:

$p<0.05$ and $p<0.01$ (Donnet's Test)

And # and ## mean the significant difference relative to the control rat group:

$p<0.05$ and $p<0.01$ (Student's t-Test)

As will be seen from the results shown in FIG. 5, the diuresis was observed when the compound of the present invention was administered to the animals in pathema of hepatocirrhosis. Moreover, the results shown in FIG. 6 indicate that the compound inhibited any increase in the amount of ascites due to the hepatocirrhosis.

TEST EXAMPLE 5

Effect of the Compound of the Invention in Renal Failure Model

This test was performed according to the method of Kusaka et al. (The Japanese Journal of Pharmacology, 1995, 68:213–216). Puromycin Aminonucleoside (PAN) [100 mg/3ml (physiological saline)/kg] was intravenously administered to Wistar female rats and fall into nephrosis. On 8, 9 and 10 day after the administration of PAN, there were orally administered, to each group, 2 ml/kg of 5% gum arabic (5% AG) as the medium for suspension, 1 mg/2 ml (5% AG)/kg of the compound of Example 18, 25, 30 or 47, or 30 mg/2 ml (5% AG)/kg of the compound of Comparative Example 3, once a day. The animals were fasted, while they could freely take water in a metabolic cage, till the administration on 10 day after the completion of the administration on 9 day. After the administration on 10 day of 5% AG or the compound of Example 18, 25, 30 or 47 or Comparative Example 3 and the subsequent oral loading of 25 ml/kg of physiological saline, the cumulative urine for 6 hours after the administration on the 10 day was collected from each animal, while depriving of feed and water, and determined the amount of the urine. Immediately after the completion of the urine-collection, the rats were subjected to abdominal section under ether-anesthetization and the ascites thereof was absorbed in absorbent cotton to determine the wet weight of the cotton, followed by determination of the amount of the ascites (g) based on the difference in weight between the wet cotton and the dry cotton prior to the absorption of the ascites.

Figure 7:
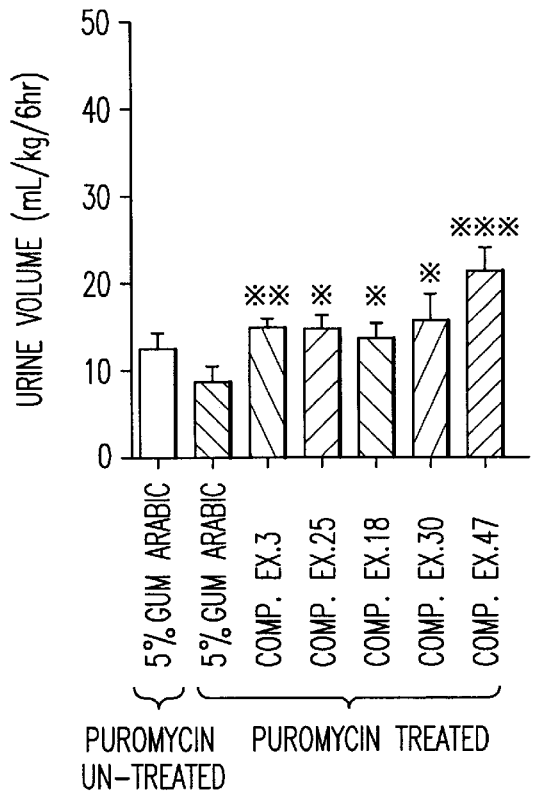
FIG. 7 shows the diurectic effect of the compounds in a renal failure model.
Figure 8:
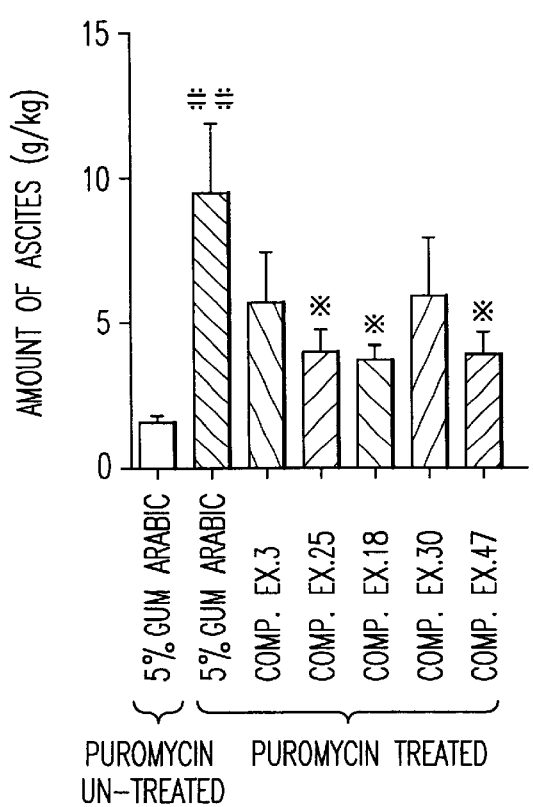
FIG. 8 shows the inhibitory effect of the compounds on the ascites volume in a renal failure model.

These results are shown in FIGS. 7 and 8. In FIGS. 7 and 8, each numerical value was expressed in terms of the average of 4 to 7 measurements (±standard error).

In these figures, *,  and * mean the significant difference relative to the 5% gum arabic-administered rat group which had been treated with Puromycin:

$p<0.05$, $p<0.01$ and $p<0.001$ (Student's t-Test)

and ## means the significant difference relative to the group free of Puromycin-treatment:

$p<0.01$ (Student's t-Test)

As will be seen from the results shown in FIG. 7, the diurese was observed when the compound of the present invention was administered to the animals in pathema of renal failure. Moreover, the results shown in FIG. 8 indicate that the compound inhibited any increase in the amount of ascites due to the renal failure.

TEST EXAMPLE 6

Effects of the Compound on Cold-Injury Trauma Rat Brain Model

This test was performed according to the method of Kagawa et al. (NOUSHINKEI GEKA (Neurosurgery), 1993, 21:1103–1107). Sprague-Dawley male rats were anesthetized by intraperitoneally administering 35 to 40 mg/kg of Pentobarbital, the scalp of the animal was opened to thus expose the parietal bone. Then a rod (diameter: 5 mm) of gun metal which had been sufficiently cooled with liquid nitrogen was brought into contact with the left hand side of the parietal bone for 60 seconds and damaged the brain through freezing and thereafter, the scalp was closed with an adhesive for surgical use. The compound of Example 18 (1 and 10 mg/2 ml/kg) dissolved in 1% Tween 80 solution was intraperitoneally administered 22.5 hours after the foregoing treatment. After 24 hours, the heads of these rats were removed to excise the brain thereof, followed by determination of the wet weight of the respective right and left cerebral hemispheres. The brain thus excised was dried at 110° C. for 24 hours to determine the dry weight of the brain. Thus, the amount of water present in the brain was evaluated on the basis of the difference between the wet and dry weights of the brain and divided by the wet weight to thus define the moisture content (B.M.C.)(%) of the brain.

B.M.C.(%)=[(wet Wt.–Dry Wt.)/Wet Wt.]×100

Wt.: weight

Further, brain edema-inhibitory rate (B.E.I.R.)(%) was evaluated according to the following equation:

B.E.I.R. (%)=[1–[(B.M.C. of Ex.18-Administered Group)–(B.M.C. of sham Operated Group)]/[(B.M.C. of Brain Edema Control Group)–(B.M.C. of sham Operated Group)]]×100

Figure 9:
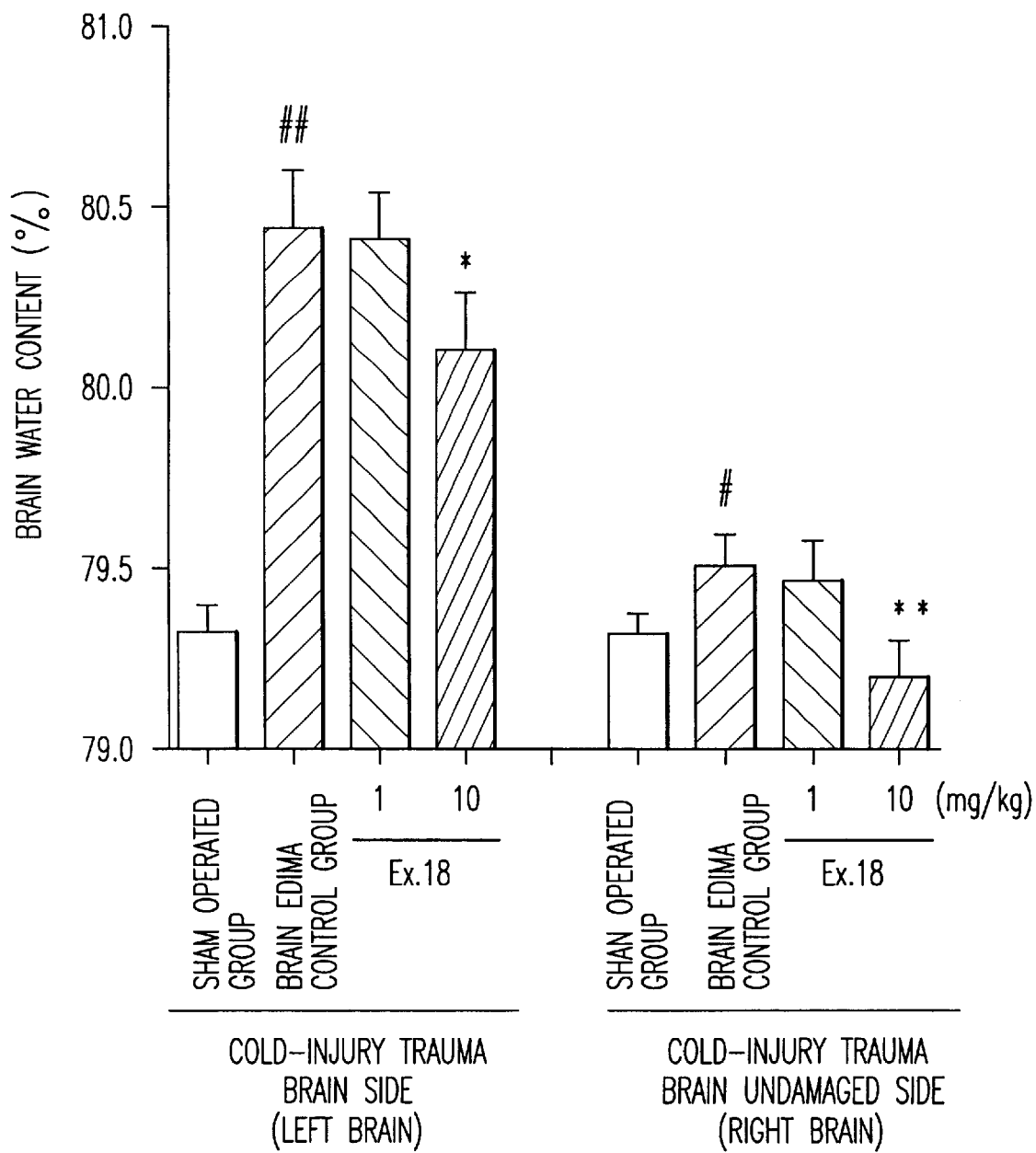
FIG. 9 shows the inhibitory effect of the compound on the brain water content in cold-injury trauma rat brain model.

The results thus obtained are shown in FIG. 9. In FIG. 9, each numerical value was expressed in terms of the average of 10 measurements (±standard error).

In these figures, * and ** mean the significant differences relative to the brain edema control rat group:

$p<0.05$ and $p<0.01$ (Williams Test)

and # and ## mean the significant differences relative to the falsely operated rat group:

$p<0.05$ and $p<0.01$ (Student's t-Test)

As will be seen from the results shown in FIG. 9, that the compound inhibited any increase in the moisture content of the brain due to the brain edema.

TEST EXAMPLE 7

Acute Toxicity Test

To groups of male ICR mice (6-week-old) each consisting of 5 animals, there were orally administered the compounds of Examples 13, 18, 25 and 30 and Comparative Examples 2 and 5 suspended in 5% gum arabic solution at doses of 150, 500 and 1500 mg/kg, followed by observation of the general symptoms of these animals during 7 days after the administration to thus evaluate the number of death. In this respect, mice were given feed and water ad libitum throughout this test except for the term extending from 16 to 20 hours before the administration and 4 hours after the administration. The results of this test are summarized in the following Table 4.

The animals to which the compounds of the present invention were administered did not die at all even at the highest dose of 1500 mg/kg. On the other hand, 4 out of 5 mice were dead at a dose of 1500 mg/kg of Comparative Example 2. At a dose of 1500 and 500 mg/kg of Comparative Example 5, 2 out of 5 mice were dead. The foregoing results clearly indicate that the compounds of the present invention are excellent in safety. Compound of Comp. Ex. 5 (YM-087: the compound (hydrochloride) of Example 18(2) of P.I.A No. WO95/03305):

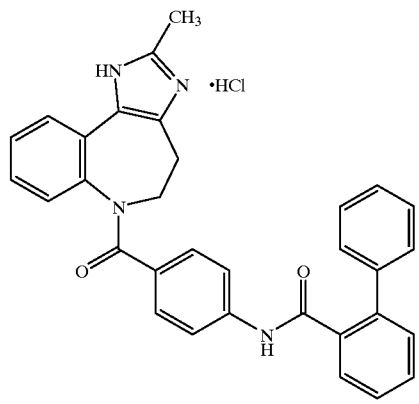

TABLE 4

Acute Toxicity Test (the number of death out of 5 or 6 animals)

| Test Compound | Dose | | |
|---|---|---|---|
| (Example No.) | 150 mg/kg | 500 mg/kg | 1500 mg/kg |
| Example 13 | — | 0/5 | 0/5 |
| Example 18 | 0/6 | 0/6 | 0/6 |
| Example 25 | 0/6 | 0/6 | 0/6 |
| Example 30 | 0/6 | 0/6 | 0/6 |
| Comparative Example 2 | 0/5 | 0/5 | 4/5 |
| Comparative Example 5 | 0/5 | 2/5 | 2/5 |

REFERENCE EXAMPLE 1

1-(2-Nitrophenyl)-L-proline

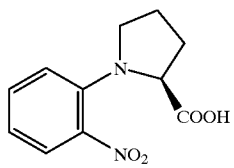

There were dissolved, in 25 ml of dimethyl sulfoxide, 1 g of L-proline and 1.23 g of 1-fluoro-2-nitrobenzene, then 1.65 ml of triethylamine was added to the resulting solution and the mixture was stirred with heating at 60° C. for 16 hours. The reaction solution was cooled to room temperature then poured into ice water and washed with ether. The aqueous phase was acidified with hydrochloric acid and extracted with ether. After washing the organic phase with water, the phase was dried over anhydrous magnesium sulfate and then concentrated. The resulting residue was treated by silica gel column chromatography, followed by elution with methanol/chloroform (1/49) to give 1.65 g (yield: 80.3%) of the title compound.

$^1$H-N.M.R. (CDCl$_3$) δ: 1.90–2.24 (3 H, m), 2.44–2.56 (1 H, m), 3.02–3.11 (1 H, m), 3.51–3.62 (1 H, m), 4.41 (1H, t, J=7.0 Hz), 6.86–6.95 (2 H, m), 7.41 (1H, ddd, J=8.1, 7.3, 1.8 Hz), 7.75 (1H, dd, J=8.1, 1.8 Hz); I.R. (neat) vcm$^{-1}$: 2970, 1730, 1605, 1500, 1360, 1218.

REFERENCE EXAMPLE 2

1-(2-Nitrophenyl)-D-proline

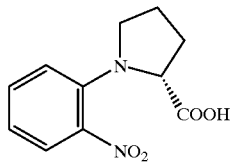

The same procedures used in Reference Example 1 were repeated except for using D-proline and 1-fluoro-2-nitrobenzene to give the title compound. Yield 82.3%.

$^1$H-N.M.R. (CDCl$_3$) δ: 1.90–2.24 (3 H, m), 2.44–2.56 (1 H, m), 3.02–3.11 (1 H, m), 3.51–3.62 (1 H, m), 4.41 (1H, t, J=7.0 Hz), 6.86–6.95 (2 H, m), 7.41 (1H, ddd, J=8.1, 7.3, 1.8 Hz), 7.75 (1H, dd, J=8.1, 1.8 Hz); I.R. (neat) vcm$^{-1}$: 2970, 1730, 1605, 1500, 1360, 1280.

REFERENCE EXAMPLE 3

(2S, 4R)-4-Hydroxy-1-(2-nitrophenyl) Proline

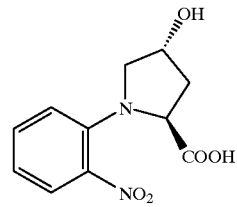

The same procedures used in Reference Example 1 were repeated except for using trans-4-hydroxy-L-proline and 1-fluoro-2-nitrobenzene to give the title compound. Yield 71.1%.

$^1$H-N.M.R. (CDCl$_3$) δ: 2.21–2.25 (1 H, m), 2.45–2.53 (1 H, m), 2.70 (1H, dd, J=11.0, 1.5 Hz), 3.79 (1H, dd, J=11.0, 3.6 Hz), 4.20–5.55 (3 H, m), 6.72–6.82 (1 H, m), 6.91–6.97 (1 H, m), 7.32–7.40 (1 H, m), 7.73 (1H, dd, J=8.1, 1.5 Hz); I.R. (KBr) vcm$^{-1}$: 3440, 1750, 1605, 1560, 1505, 1480, 1440, 1270, 1175.

REFERENCE EXAMPLE 4

Cis-4-Hydhoxy-D-Proline Methyl Ester Hydrochloride

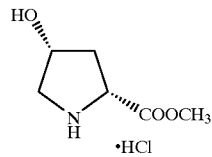

Cis-4-hydroxy-D-proline hydrochloride (disclosed in J. Org. Chem., 1981, 46:2954; 15.53 g) was suspended in 180 ml of methanol and 21.7 ml of thionyl chloride was dropwise added to the resulting suspension over one hour while cooling the suspension to −20° C. After the completion of the dropwise addition, the mixture was stirred at room temperature for one and half hours. The reaction solution was concentrated, then ether was added to the resulting residue, the crystals thus separated were filtered off, washed with ether and dried to give 15.35 g (yield 91.3%) of the title compound.

$^1$H-N.M.R. (DMSO-d$_6$) δ: 2.13–2.23 (1 H, m), 2.26–2.38 (1 H, m), 3.14–3.30 (3 H, m), 3.75 (3 H, s), 4.35–4.43 (1 H, m), 4.45–4.56 (1 H, m), 8.80–9.32 (1 H, m), 10.35–10.87 (1 H, m); I.R. (KBr) vcm$^{-1}$: 3400, 3000, 1725, 1580, 1380, 1250, 1095.

REFERENCE EXAMPLE 5

Trans-4-Hydroxy-L-Proline Methyl Ester Hydrochloride

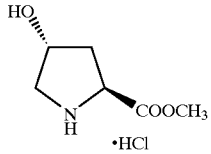

A solution prepared by dissolving 13.9 g of trans-4-hydroxy-L-proline in 150 ml of methanol was cooled to −20° C. and then 25 ml of thionyl chloride was dropwise added to the solution. After the completion of the dropwise addition, the resulting mixture was stirred at 40° C. for 30 minutes. The reaction solution was concentrated, followed by addition of ether to the resulting residue, filtration of the crystals thus precipitated, washing the crystals with ether and drying them to give 18.86 g (yield 98.0%) of the title compound.

$^1$H-N.M.R. (DMSO-d$_6$) δ: 2.03–2.26 (2 H, m), 3.03–3.12 (1 H, m), 3.37 (1 H, dd, J=12.1, 4.4 Hz), 3.76 (3H, s), 4.38–4.51 (2 H, m), 5.61 (1 H, brs), 8.75–9.25 (1 H, m), 10.25–10.75 (1 H, m); I.R. (KBr) vcm$^{-1}$: 3370, 2950, 1740, 1585, 1360, 1285, 1245.

REFERENCE EXAMPLE 6

(2R,4R)-4-Hydroxy-1-(2-Nitrophenyl) Proline Methyl Ester

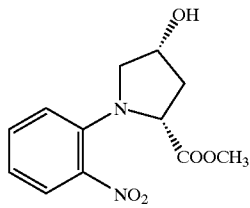

The same procedures used in Reference Example 1 were repeated except for using the cis-4-hydroxy-D-proline methyl ester hydrochloride prepared in Reference Example 4 and 1-fluoro-2-nitrobenzene to give the title compound. Yield 97.2%.

$^1$H-N.M.R. (CDCl$_3$) δ: 2.16–2.26 (1 H, m), 2.50–2.62 (1 H, m), 2.91 (1H, d, J=9.0 Hz), 3.41–3.48 (1 H, m), 3.57 (1 H, dd, J=10.5, 5.4 Hz), 3.75 (3 H, s), 4.40–4.55 (2 H, m), 6.81–6.89 (2 H, m), 7.35–7.43 (1 H, m), 7.64–7.79 (1 H, m); I.R. (neat) vcm$^{-1}$: 3450, 1740, 1605, 1510, 1350, 1280, 1210, 1180.

REFERENCE EXAMPLE 7

(2S, 4R-4-Hydroxy-1-(2-Nitrophenyl) Proline Methyl Ester

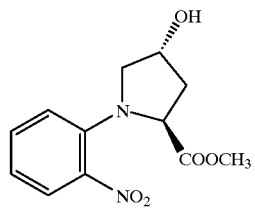

The same procedures used in Reference Example 1 were repeated except for using the trans-4-hydroxy-L-proline methyl ester hydrochloride prepared in Reference Example 5 and 1-fluoro-2-nitrobenzene to give the title compound. Yield 92.2%.

$^1$H-N.M.R. (CDCl$_3$) δ: 1.74 (1H, d, J=4.0 Hz), 2.20–2.35 (1 H, m), 2.43–2.55 (1 H, m), 2.82–2.92 (1 H, m), 3.70 (3 H, s), 3.86 (1 H, dd, J=11.0, 3.7 Hz), 4.55–4.77 (2 H, m), 6.81–6.99 (2 H, m), 7.34–7.47 (1 H, m), 7.77 (1 H, dd, J=8.4, 1.8 Hz); I.R. (neat) vcm$^{-1}$: 3480, 1735, 1605, 1510, 1360, 1275, 1205, 1175.

REFERENCE EXAMPLE 8

(2R,4S)-4-Hydroxy-1-(2-Nitrophenyl) Proline

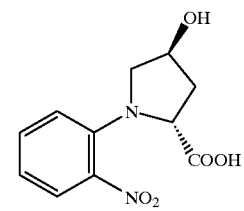

To 10 ml of anhydrous toluene, there were added 0.93 g of the (2R, 4R)-4-hydroxy-1-(2-nitrophenyl) proline methyl ester prepared in Reference Example 6, 1.8 g of triphenyl phosphine, 0.42 g of acetic acid and 0.25 g of triethylamine and then 1.4 g of diisopropyl azodicarboxylate was dropwise added to the resulting mixture over one hour with ice-cooling. After stirring the mixture for 16 hours with heating to 60° C. and cooling it to room temperature, 8 ml of a 1.3N sodium hydroxide solution was added to the mixture, followed by stirring the mixture for additional 4 hours at room temperature. The pH of the reaction solution was adjusted to 7 with concentrated hydrochloric acid, the insolubles precipitated were filtered off, the resulting filtrate was fractionated and the aqueous phase obtained was washed with ether. Then the aqueous phase was acidified with hydrochloric acid, followed by extraction with ethyl acetate, washing with water and drying over anhydrous magnesium sulfate. After concentration of the ethyl acetate extract, the resulting residue was recrystallized from ethyl acetate-chloroform to give 0.66 g (yield 74.8%) of the title compound.

$^1$H-N.M.R. (DMSO-d$_6$) δ: 2.00–2.12 (1 H, m), 2.30 (1 H, dd, J=12.7, 6.8 Hz), 2.51–2.58 (1 H, m), 3.58 (1 H, dd, J=10.7, 3.4 Hz), 4.33–4.39 (1 H, m), 4.51 (1 H, dd, J=9.8, 6.8 Hz), 5.03 (1 H, brs), 6.82 (1 H, t, J=8.3 Hz), 6.91 (1H, d, J=8.3 Hz), 7.42–7.51 (1 H, m), 7.73 (1 H, dd, J=8.3, 1.5 Hz), 12.9 (1 H, brs); I.R. (KBr) vcm$^{-1}$: 3440, 1750, 1605, 1560, 1505, 1480, 1440, 1270, 1175.

REFERENCE EXAMPLE 9

(3aS)-1,2,3,3a,4,5-Hexahydro-Pyrrolo[1,2-a]
Quinoxalin-4-One

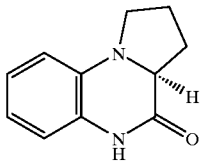

The 1-(2-nitrophenyl)-L-proline (1.56 g) obtained in Reference Example 1 was catalytically reduced at ordinary temperature, in the presence of 0.6 g of a 10% palladium-carbon catalyst, in 150 ml of methanol. After completion of the reaction, the catalyst was removed and then the reaction solution was concentrated to dryness to give 1.04 g (yield 83.3%) of the title compound.

$^1$H-N.M.R. (CDCl$_3$) δ: 1.98–2.37 (4 H, m), 3.15–3.4 (1 H, m), 3.43–3.54 (1 H, m), 3.68–3.77 (1 H, m), 6.60 (1H, d, J=7.7 Hz), 6.71–6.79 (2 H, m), 6.94–7.02 (1 H, m), 8.19 (1 H, brs); I.R. (KBr) vcm$^{31}$ $^1$: 2970, 1680, 1610, 1510, 1440, 1405, 1365.

REFERENCE EXAMPLE 10

(3aR)-1,2,3,3a,4,5-Hexahydro-Pyrrolo[1,2-a]
Quinoxalin-4-one

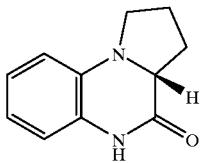

The same procedures used in Reference Example 9 were repeated except for using the compound: 1-(2-nitrophenyl)-D-proline prepared in Reference Example 2 to give the title compound. Yield 95.9%.

$^1$H-N.M.R. (CDCl$_3$) δ: 1.98–2.37 (4 H, m), 3.15–3.24 (1 H, m), 3.43–3.54 (1 H, m), 3.68–3.77 (1 H, m), 6.60 (1H, d, J=7.7 Hz), 6.71–6.79 (2 H, m), 6.94–7.02 (1 H, m), 8.19 (1 H, brs); I.R. (KBr) vcm$^{-1}$: 2970, 1680, 1610, 1510, 1440, 1405, 1365.

REFERENCE EXAMPLE 11

(2R,3aS,-2-Hydroxy-1,2,3,3a,4.5-Hexahydro-
Pyrrolo[1,2-a]Quinoxalin-4-one

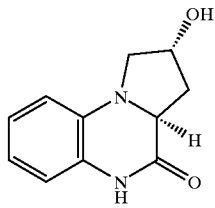

The same procedures used in Reference Example 9 were repeated except for using the compound: (2S, 4R)-4-hydroxy-1-(2-nitrophenyl) proline prepared in Reference Example 3 to give the title compound. Yield 90.7%.

$^1$H-N.M.R. (DMSO-d$_6$) δ: 1.96–2.14 (2 H, m), 3.00 (1 H, dd, J=10.3, 2.4 Hz), 3.65 (1 H, dd, J=10.3, 5.6 Hz), 3.85 (1 H, dd, J=9.8, 6.6 Hz), 4.39–4.48 (1H, m), 6.53 (1H, d, J=7.8 Hz), 6.61–6.69 (1 H, m), 6.80 (1 H, dd, J=7.8, 1.5 Hz), 6.86 (1 H, td, J=7.8, 1.5 Hz), 10.30 (1 H, brs); I.R. (KBr) vcm$^{-1}$: 3400, 1680, 1520, 1440, 1420, 1380, 1320.

REFERENCE EXAMPLE 12

(2R,3aR)-2-Hydroxy-1,2,3,3a,4,5-Hexahydro-
Pyrrolo[1,2-a]Quinoxalin-4-one

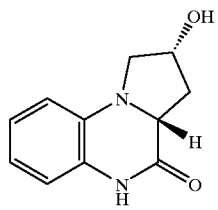

The same procedures used in Reference Example 9 were repeated except for using the compound: (2R,4R)-4-hydroxy-1-(2-nitrophenyl) proline methyl ester prepared in Reference Example 6 to give the title compound. Yield 81.9%.

$^1$H-N.M.R. (CDCl$_3$) δ: 2.03 (1 H, brs), 2.31–2.42 (1 H, m), 2.55–2.68 (1 H, m), 3.30 (1 H, dd, J=10.3, 5.1 Hz), 3.48–3.54 (1 H, m), 3.62 (1 H, t, J=8.1 Hz), 4.55–4.62 (1 H, m), 6.61 (1H, d, J=7.1 Hz), 6.72–6.82 (2 H, m), 6.93–7.01 (1 H, m), 8.20 (1 H, brs); I.R. (KBr) vcm$^{-1}$: 3440, 3200, 1695, 1610, 1505, 1430, 1400, 1350, 1320, 1005.

REFERENCE EXAMPLE 13

(2S, 3aR)-2-Hydroxy-1,2,3,3a,4,5-Hexahydro-
Pyrrolo[1,2-a]Quinoxalin-4-one

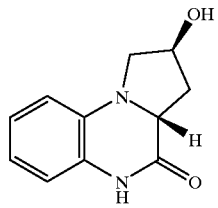

The same procedures used in Reference Example 9 were repeated except for using the compound: (2R,4S)-4-hydroxy-1-(2-nitrophenyl) proline prepared in Reference Example 8 to give the title compound. Yield 85.1%.

$^1$H-N.M.R. (DMSO-d$_6$) δ: 1.96–2.14 (2 H, m), 3.00 (1 H, dd, J=10.3, 2.4 Hz), 3.65 (1 H, dd, J=10.3, 5.6 Hz), 3.85 (1 H, dd, J=9.8, 6.6 Hz), 4.39–4.48 (1H, m), 6.53 (1H, d, J=7.8 Hz), 6.61–6.69 (1 H, m), 6.80 (1 H, dd, J=7.8, 1.5 Hz), 6.86 (1 H, td, J=7.8, 1.5 Hz), 10.30 (1 H, brs); I.R. (KBr) vcm$^{-1}$: 3400, 1680, 1520, 1440, 1420, 1380, 1320.

REFERENCE EXAMPLE 14

(3aS)-1,2,3,3a,4,5-Hexahydro-Pyrrolo[1,2-a]Quinoxaline

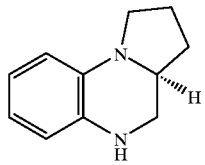

A solution of 1.04 g of (3aS)-1,2,3,3a,4,5-hexahydro-pyrrolo[1,2-a]quinoxalin-4-one prepared in Reference Example 9 in 30 ml of anhydrous tetrahydrofuran was dropwise added, with ice-cooling, to a suspension of 0.53 g of lithium aluminum hydride in 30 ml of anhydrous tetrahydrofuran over 30 minutes. After the dropwise addition, the mixture was refluxed with heating for 2 hours. The reaction solution was ice-cooled, then 100 ml of ethyl acetate was gradually added thereto and the mixture was further stirred at room temperature for 15 hours. Water was added to the reaction liquid and the separated insolubles were filtered off through a Celite layer. The resulting organic phase was washed with water, dried over anhydrous magnesium sulfate and then concentrated. The resulting residue was subjected to silica gel column chromatography treatment and eluted with chloroform/ethyl acetate (99/1) to give 0.95 g (yield 98.1%) of the title compound.

$^1$H-N.M.R. (CDCl$_3$) δ: 1.40–1.52 (1 H, m), 1.89–2.13 (3 H, m), 2.80–2.89 (1 H, m), 3.20–3.38 (2 H, m), 3.43–3.93 (3 H, m), 6.41–6.46 (1 H, m), 6.51–6.59 (2 H, m), 6.67–6.74 (1 H, m); I.R. (KBr) vcm$^{-1}$: 3330, 2830, 1595, 1510, 1370, 1315, 1260.

REFERENCE EXAMPLE 15

(3aR)-1,2,3,3a,4,5-Hexahydro-Pyrrolo[1,2-a]Quinoxaline

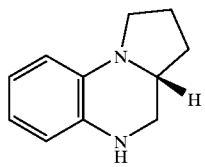

The same procedures used in Reference Example 14 were repeated except for using the compound (3aR)-1,2,3,3a,4,5-hexahydro-pyrrolo[1,2-a]quinoxalin-4-one prepared in Reference Example 10 to give the title compound. Yield 96.9%.

$^1$H-N.M.R. (CDCl$_3$) δ: 1.40–1.52 (1 H, m), 1.89–2.13 (3 H, m), 2.80–2.89 (1 H, m), 3.20–3.38 (2 H, m), 3.43–3.93 (3 H, m), 6.41–6.46 (1 H, m), 6.51–6.59 (2 H, m), 6.67–6.74 (1 H, m); I.R. (KBr) vcm$^{-1}$: 3330, 2830, 1595, 1510, 1370, 1315, 1260.

REFERENCE EXAMPLE 16

(2R,3aS)-2-Hydroxy-1,2,3,3a,4,5-Hexahydro-Pyrrolo[1,2-a]Quinoxaline

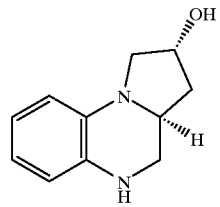

The same procedures used in Reference Example 14 were repeated except for using the compound (2R,3aS)-2-hydroxy-1,2,3,3a,4,5-hexahydro-pyrrolo[1,2-a]quinoxalin-4-one prepared in Reference Example 11 to give the title compound. Yield 85.0%.

$^1$H-N.M.R. (CDCl$_3$) δ: 1.58–1.69 (1 H, m), 2.06–2.15 (1 H, m), 2.76–2.86 (1 H, m), 3.33 (1H, d, =10.6 Hz), 3.51–3.59 (2 H, m), 3.78–3.90 (1 H, m), 4.59 (1 H, t, J=4.6 Hz), 6.43 (1H, d, J=7.3 Hz), 6.52–6.60 (2H, m), 6.67–6.75 (1 H, m); I.R. (KBr) vcm$^{-2}$: 3520, 3350, 2850, 1600, 1520, 1460, 1440, 1360, 1320, 1260.

REFERENCE EXAMPLE 17

(2R,3aR)-2-Hydroxy-1,2,3,3a,4,5-Hexahydro-Pyrrolo[1,2-a]Quinoxaline

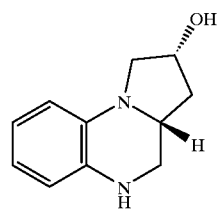

The same procedures used in Reference Example 14 were repeated except for using the compound (2R,3aR)-2-hydroxy-1,2,3,3a,4,5-hexahydro-pyrrolo[1,2-a] quinoxalin-4-one prepared in Reference Example 12 to give the title compound. Yield 63.6%.

$^1$H -N.M.R. (CDCl$_3$) δ: 1.55 (1 H, ddd, J=13.9, 9.2, 6.2 Hz), 2.39–2.51 (1 H, m), 3.11 (1 H, t, J=9.2Hz), 3.25–3.54 (5 H, m), 4.55–4.65 (1 H, m), 6.43 (1H, dd, J=7.7, 1.5 Hz), 6.51–6.7 2 (3 H, m); I.R. (KBr) vcm$^{-1}$: 3330, 2840, 1600, 1515, 1505, 1360, 1315.

REFERENCE EXAMPLE 18

(2S, 3aR)-2-Hydroxy-1,2,3,3a,4,5-Hexahydro-Pyrrolo[1,2-a]Quinoxaline

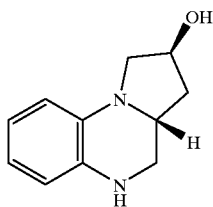

The same procedures used in Reference Example 14 were repeated except for using the compound (2S, 3aR)-2-hydroxy-1,2,3,3a,4,5-hexahydro-pyrrolo[1,2-a]quinoxalin-4-one prepared in Reference Example 13 to give the title compound. Yield 62.2%.

¹H-N.M.R. (CDCl₃) δ: 1.58–1.68 (1 H, m), 2.04–2.14 (1 H, m), 2.74–2.85 (1 H, m), 3.31 (1H, d, =10.8 Hz), 3.48–3.57 (2 H, m), 3.75–3.90 (1 H, m), 4.56–4.62 (1 H, m), 6.41 (1H, d, J=7.3 Hz), 6.52–6.60 (2 H, m), 6.66–6.75 (1 H, m); I.R. (KBr) vcm⁻¹: 3520, 3350, 2850, 1600, 1520, 1460, 1440, 1360, 1320, 1260.

REFERENCE EXAMPLE 19

(11aS)-1,2,3,10,11,11a-Hexahydro-5H-Pyrrolo[2,1-c][1,4]Benzodiazepin-5,11-Dione

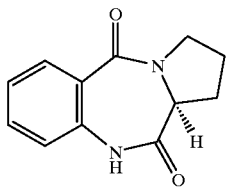

(Method A): (a-1)

A mixed solution containing 6.8 g of 2-nitrobenzoic acid and 6 ml of thionyl chloride was heated with refluxing for one hour. After allowing the reaction solution to cool, the excess of the thionyl chloride was distilled off under reduced pressure. The resulting acid chloride was dissolved in 15 ml of dichloromethane, followed by dropwise addition of this solution to a solution of 5.6 g of L-proline methyl ester hydrochloride and 10.2 g of triethylamine in 80 ml of dichloromethane at 0° C. over 20 minutes in a nitrogen gas atmosphere and stirring of the mixture at room temperature for 2 hours. The reaction solution was washed with, in order, water, a saturated aqueous solution of sodium hydrogencarbonate, a 1N hydrochloric acid solution and a saturated sodium chloride solution, then dried and concentrated under reduced pressure. The resulting residue was treated by silica gel column chromatography and then eluted with ethyl acetate/chloroform (1/99) mixed solvent to give 6.4 g (yield 68.5/) of (2S)-1-(2-nitrobenzoyl) proline methyl ester as a red oily substance.

¹H-N.M.R. (CDCl₃) δ: 1.88–2.15 (4 H, m), 3.1 8–3.29 (1 H, m), 3.31–3.42 (1 H, m), 3.18 (3 H, s), 4.77 (1 H, dd, J=8.8, 4.4 Hz), 7.51–7.62 (2 H, m), 7.7 0–7.78 (1 H, m), 8.16–8.22 (1 H, m); I.R. (neat) vcm⁻¹: 2950, 1740, 1640, 1530, 1420, 1345, 1200, 1170.

(a-2)

To a solution of 6.4 g of (2S)-1-(2-nitrobenzoyl) proline methyl ester in 250 ml of methanol, there was added 1.5 g of a 10% palladium-carbon catalyst and then the resulting mixture was stirred at room temperature for 6 hours in a hydrogen gas atmosphere. The catalyst present in the reaction solution was filtered off and the filtrate was concentrated under reduced pressure to give 3.8 g (yield 75.2%) of the title compound as white crystals.

¹H-N.M.R. (CDCl₃) δ: 2.00–2.08 (3 H, m), 2.72–2.81 (1 H, m), 3.55–3.68 (1 H, m), 3.77–3.87 (1 H, m), 4.05–4.12 (1 H, m), 6.99 (1 H, dd, J=8.3, 0.9 Hz), 7.22–7.31 (1 H, m), 7.44–7.52 (1 H, m), 8.02 (1 H, dd, J=8.3, 0.9 Hz), 8.23 (1 H, s); I.R. (KBr) vcm⁻¹: 3240, 1700, 1680, 1630, 1620, 1480, 1450, 1420, 1265.

(Method B)

Isatoic anhydride (3.0 g) and L-proline (2.1 g) were suspended in 60 ml of N,N-dimethylformamide and the suspension was stirred with heating at 130° C. for 2.5 hours. After allowing the reaction solution to cool, it was concentrated under reduced pressure, followed by washing the precipitated crystals with water and drying them to give 2.6 g (yield 65.3%) of the title compound.

REFERENCE EXAMPLE 20

(11aR)-1,2,3,10,11,11a-Hexahydro-5H-Pyrrolo[2,1-c][1,4]Benzodiazepin-5,11-Dione

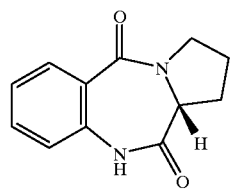

The same procedures used in the method B in Reference Example 19 were repeated except for the use of isatoic anhydride and D-proline to form the title compound. Yield 78.9%.

¹ H-N.M.R. (CDCl₃) δ: 2.00–2.08 (3 H, m), 2.7 2–2.81 (1 H, m), 3.55–3.68 (1 H, m), 3.77–3.87 (1 H, m), 4.05–4.12 (1 H, m), 6.99 (1 H, dd, J=8.3, 0.9 Hz) 7.22–7.31 (1 H, m), 7.44–7.52 (1 H, m), 8.02 (1 H, dd, J=8.3, 0.9 Hz), 8.23 (1 H, s); I.R. (KBr) vcm⁻¹: 3240, 1700, 1680, 1630, 1620, 1480, 1450, 1420, 1265.

REFERENCE EXAMPLE 21

(2R,11aS)-2-Hydroxy-1,2,3,10,11,11a-Hexahydro-5H-Pyrrolo[2,1-c][1,4]Benzodiazepin-5,11-Dione

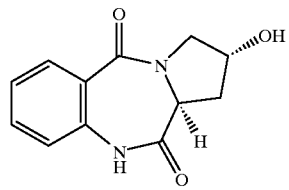

Isatoic anhydride (3.5 g) and trans-4-hydroxy-L-proline (2.8 g) were suspended in 60 ml of dimethyl sulfoxide and the suspension was heated with stirring at 120° C. for 2 hours. After allowing the reaction liquid to cool, the solvent was distilled off under reduced pressure and the resulting residue was washed with ethyl acetate and dried. The crude crystals were recrystallized from ethanol to give 3.9 g (yield 78.5%) of the title compound.

¹H-N.M.R. (DMSO-d6) δ: 1.89–1.98 (1 H, m), 2.58–2.67 (1 H, m), 3.47 (1 H, dd, J=11.9, 4.6 Hz), 3.62 (1H, dd, J=11.9, 2.9 Hz), 4.18 (1 H, dd, J=8.1, 5.9 Hz), 4.31–4.32 (1 H, m), 5.14 (1 H, d, J=3.9 Hz), 7.13 (1H, d, J=7.1 Hz), 7.20–7.28 (1 H, m), 7.48–7.57 (1H, m), 7.76–7.83 (1 H, m), 10.53 (1 H, s); I.R. (KBr) νcm⁻¹: 3520, 3420, 3220, 1680, 1630, 1610, 1480, 1450, 1420, 1110.

REFERENCE EXAMPLE 22

Cis-4-Hydroxy-D-Proline

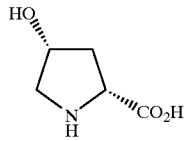

To a solution of 4.5 g of cis-4-hydroxy-D-proline hydrochloride in 300 ml of ethanol, there was added 13.1 g of propylene oxide at room temperature and then the mixture was heated under refluxing for one hour. After allowing the reaction liquid to cool, the crystals precipitated were filtered off, washed with ethanol and then dried to give 3.0 g (yield 85.4%) of the title compound.

¹H-N.M.R. (D₂O) δ: 2.33–2.39 (1 H, m), 2.62 (1 H, dd d, J=12.9, 10.5, 4.3 Hz), 3.44–3.60 (2 H, m), 4.32 (1 H, dd, J=10.5, 4.3 Hz), 4.67–4.70 (1 H, m).

REFERENCE EXAMPLE 23

(2R,11aR)-2-Hydroxy-1,2,3,10,11,11a-Hexahydro-5H-Pyrrolo[2,1-c][1,4]Benzodiazepin-5,11-Dione

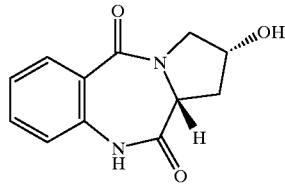

The same procedures used in Reference Example 21 were repeated except for the use of cis-4-hydroxy-D-proline to thus give the title compound. Yield 68.5%.

¹H-N.M.R. (DMSO-d₆) δ: 2.11–2.23 (1 H, m), 2.52–2.63 (1 H, m), 3.23–3.40 (2 H, m), 3.72–3.80 (1 H, m), 4.10–4.18 (1 H, m), 4.26–4.35 (1 H, m), 4.86 (1H, brs), 7.15 (1H, d, J=8.1 Hz), 7.19–7.27 (1 H, m), 7.47–7.56 (1 H, m), 7.77–7.82 (1 H, m), 10.48 (1 H, s); I.R. (KBr) νcm⁻¹: 3520, 3420, 3220, 1680, 1630, 1610, 1480, 1450, 1420, 1110.

REFERENCE EXAMPLE 24

(11aS)-1,2,3,10,11,11a-Hexahydro-5H-Pyrrolo[2,1-c][1,4]Benzodiazepin-5-One

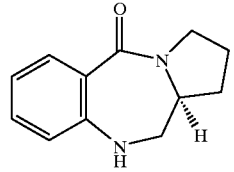

(Method A)

To a solution of 13.9 g of (2S)-1-(2-nitrobenzoyl) proline methyl ester in 100 ml of dichloromethane, there was dropwise added 100 ml of a 1M solution of diisobutyl aluminum hydride in dichloromethane at −70° C. over 30 minutes in a nitrogen gas atmosphere and then the mixture was stirred at −70° C. for one hour. A mixed solvent containing 5 ml of methanol and 5 ml of dichloromethane was added to the reaction solution at −70° C., then 10 ml of saturated ammonium chloride aqueous solution was added thereto and the mixture was stirred at room temperature for one hour. The crystals precipitated were filtered off, the filtrate was washed with water, dried and then concentrated under reduced pressure. The resulting oily substance was dissolved in 200 ml of methanol, 5.0 g of a 10% palladium-carbon catalyst was added to the solution and the resulting mixture was stirred at room temperature over 15 hours in a hydrogen gas atmosphere. The catalyst present in the reaction liquid was filtered off and the filtrate was concentrated under reduced pressure. The resulting residue was recrystallized from ethyl acetate to thus give 7.9 g (yield 78.3%) of the title compound.

¹H-N.M.R. (CDCl₃) δ: 1.64–1.97 (3 H, m), 2.17–2.32 (1 H, m), 3.33 (1 H, dd, J=12.5, 8.2 Hz), 3.50–3.73 (2 H, m), 3.77–3.94 (2 H, m), 6.55 (1 H, dd, J=8.1, 1.1 Hz), 6.74–6.81 (1 H, m), 7.15–7.22 (1 H, m), 8.01 (1 H, dd, J=8.1, 1.5 Hz); I.R. (KBr) νcm⁻¹: 3330, 2950, 1620, 1595, 1495, 1450, 1365, 1260, 1175.

(Method B)

Lithium aluminum hydride (5.69 g) was added to a suspension of 10.8 g of (11aS)-1,2,3,10,11,11a-hexahydro-5H-pyrrolo[2,1-c][1,4]benzodiazepin-5,11-dione prepared in Reference Example 19 in 215 ml of tetrahydrofuran under ice-cooling and then the mixture was stirred for 3 hours under ice-cooling. Chloroform (300 ml) was added to the reaction solution under ice-cooling, followed by careful addition of 5.7 ml of water and 5.7 ml of a 10% aqueous solution of sodium hydroxide in this order and stirring the mixture for 30 minutes. Further 2.9 ml of water and 2.9 ml of a 10% aqueous solution of sodium hydroxide were in order added to the reaction solution, the precipitates-separated were filtered off, a reduced pressure was applied to the filtrate and then it was concentrated under reduced pressure. The resulting residue was recrystallized from ethyl acetate to thus give 5.88 g (yield 58.1%) the title compound.

REFERENCE EXAMPLE 25

(11aR)-1,2,3,10,11,11a-Hexahydro-5H-Pyrrolo[2,1-c][1,4]Benzodiazepin-5-One

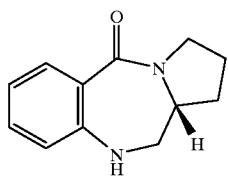

The same procedures used in Method A in Reference Example 24 were repeated using (2R)-1-(2-nitrobenzoyl) proline methyl ester to give the title compound. Yield 67.2%.

$^1$H-N.M.R. (CDCl$_3$) δ: 1.64–1.97 (3 H, m), 2.17–2.32 (1 H, m), 3.33 (1 H, dd, J=12.5, 8.2 Hz), 3.50–3.73 (2 H, m), 3.77–3.94 (2 H, m), 6.55 (1 H, dd, J=8.1, 1.1Hz), 6.74–6.81 (1 H, m), 7.15–7.22 (1 H, m), 8.01 (1H; dd, J=8.1, 1.5 Hz); I.R. (KBr) vcm$^{-1}$: 3330, 2950, 1620, 1595, 1495, 1450, 1365,1260, 1175.

REFERENCE EXAMPLE 26

(2R,11aS)-2-(t-Butyldimethylsilyloxy)-1,2,3,10,11,11a-Hexahydro-5H-Pyrrolo[2,1-c][1,4]Benzodiazepin-5-One

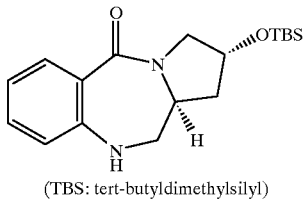

(TBS: tert-butyldimethylsilyl)

(Method A) (a-1)

The same procedures used in Method A (a-1) in Reference Example 19 were repeated using trans-4-hydroxy-L-proline methyl ester to give (2S, 4R)-4-hydroxy-1-(2-nitrobenzoyl) proline methyl ester. Yield 45.4%.

$^1$H-N.M.R. (CDCl$_3$) δ: 2.02–2.50 (3 H, m), 3.18–3.24 (1 H, m), 3.50 (3×1/6 H, s), 3.82 (3×5/6 H, s), 3.54–3.60 (1 H, m), 3.75–4.25 (1 H, m), 4.45–4.70 (1H, m), 4.85–4.90 (1 H, m), 7.35–7.75 (3 H, m), 8.15–8.25 (1 H, m).

(a-2)

To a suspension of 10.7 g of (2S, 4R)-4-hydroxy-1-(2-nitrobenzoyl) proline methyl ester and 5.7 g of imidazole in 100 ml of N,N-dimethylformamide, there was added 6.6 g of tert-butyldimethylsilyl chloride at room temperature in a nitrogen gas atmosphere and the mixture was stirred at room temperature for 2.5 hours. The reaction solution was poured into ice water, followed by extraction with ethyl acetate three times, water washing of the organic phase, drying and concentration thereof under reduced pressure. The resulting residue was subjected to silica gel column chromatography, then eluted with a 1/1 ethyl acetate/hexane mixed solvent, followed by recrystallization from ethyl acetate-hexane to give 10.6 g (yield 71.6%) of (2S, 4R)-4-(tert-butyldimethylsilyloxy)-1-(2-nitrobenzoyl) proline methyl ester as colorless needles.

$^1$H-N.M.R. (CDCl$_3$) δ: -0.01 (3 H, s), 0.04 (3 H, s), 0.85 (9×1/7 H, s), 0.91 (9×6/7 H, s), 2.10–2.40 (2H, m), 3.06–3.10 (1 H, m), 3.48 (3×1/7 H, s), 3.82 (3×6/7 H, s), 3.46–3.51 (1 H, m), 3.80–4.20 (1 H, m), 440–4.60 (1 H, m), 4.79–4.84 (1 H, m), 7.35–7.75 (3 H, m), 8.19 (1 H, d, J=8.3 Hz).

(a-3)

To a solution of 9.0 g of (2S, 4R)-4-(tert-butyldimethylsilyloxy)-1-(2-nitrobenzoyl) proline methyl ester in 90 ml of dichloromethane, there was dropwise added 44 ml of a 1M solution of diisobutyl aluminum hydride in dichloromethane at -70° C. over 30 minutes in a nitrogen gas atmosphere and then the mixture was stirred at -70° C. for one hour. A mixture containing 1 ml of methanol and 1 ml of dichloromethane was added to the reaction solution at -60° C., then 10 ml of a saturated aqueous ammonium chloride solution was added thereto and the mixture was stirred at room temperature for one hour. The precipitates separated out were filtered off, the filtrate was washed with water, dried and concentrated under reduced pressure. The resulting oily substance was dissolved in 50 ml of methanol, followed by addition of 4.5 g of a 10% palladium-carbon catalyst to the solution and stirring at room temperature for 15 hours in a hydrogen gas atmosphere. The catalyst present in the reaction solution was filtered off and the filtrate was concentrated under reduced pressure. The resulting residue was subjected to silica gel column chromatography, followed by elution with methanol/chloroform. (1/100) to thus give 3.7 g (yield 51.2%) of the title compound.

$^1$H-N.M.R. (CDCl$_3$) δ: 0.06 (6 H, s), 0.85 (9 H, s), 1.70–1.80 (1 H, m), 3.25 (1 H, dd, J=13.0, 8.5 Hz), 3.56 (1 H, dd, J=13.0, 4.1 Hz), 3.70–3.83 (2 H, m), 4.12 (1H, q, J=8.5 Hz), 4.36–4.42 (1 H, m), 4.49 (1H, brs), 6.56 (1H, d, J=8.3 Hz), 6.76 (1 H, t, J=8.3 Hz), 7.19 (1 H, t, J=8.3 Hz), 8.13 (1H, d, J=8.3 Hz); I.R. (KBr) vcm$^{-1}$: 3310, 1650, 1590, 1570.

(Method B) (b-1)

To a suspension of (2R,11aS)-2-hydroxy-1,2,3,10,11,11a-hexahydro-5H-pyrrolo(2,1-c][1,4]benzodiazepin-5,11-dione (50 g) prepared in Reference Example 21 and imidazole (33.7 g) in N,N-dimethylformamide (500 ml), there was added 37.9 g of tert-butyldimethylsilyl chloride at room temperature in a nitrogen gas atmosphere and the mixture was stirred at room temperature for 3 hours. The reaction solution was poured into one liter of ice water and the crystals precipitated were recovered by filtration. The crystals were washed with water and then dried to give 72.5 g (yield 99.9%) of (2R,11aS)-2-(tert-butyldimethylsilyloxy)-1,2,3,10,11,11a-hexahydro-5H-pyrrolo[2,1-c][1,4]benzodiazepin-5,11-dione as white crystals.

$^1$H-N.M.R. (DMSO-d$_6$) δ:0.08 (6 H, s), 0.84 (9 H, s), 1.90–1.99 (1 H, m), 2.65 (1H, dt, J=13.0, 5.0 Hz), 3.49 (1 H, dd J=11.7, 4.5 Hz), 3.60 (1 H, dd, J=11.7, 5.10 Hz), 4.20 (1 H, dd, J=8.0, 5.0 Hz), 4.44–4.52 (1 H, m), 7.12 (1H, d, J=8.0 Hz), 7.22 (1 H, t, J=8.0 Hz), 7.52 (1 H, t, J=8.0 Hz), 7.78 (1H, d, J=8.0 Hz), 10.54 (1 H, s).

(b-2)

A solution of (2R,11aS)-2-(tert-butyldimethylsilyloxy)-1,2,3,10,11,11a-hexahydro-5H-pyrrolo[2,1-c][1,4]benzodiazepin-5,11-dione (34.6 g) in tetrahydrofuran (100 ml) was dropwise added to a suspension of lithium aluminum hydride (4.2 g) in tetrahydrofuran (200 ml) at 0° C. over 15 minutes in a nitrogen gas atmosphere, followed by stirring at room temperature for one hour and at 50° C. for one hour. After ice-cooling the reaction solution, 30 ml of ethyl acetate and 8 ml of a saturated aqueous ammonium chloride solution were added to the reaction solution, the mixture was stirred for 30 minutes and the precipitates separated out were filtered off. The filtrate was dried, concentrated under reduced pressure and the resulting residue was recrystallized from ethyl acetate to give 18.4 g (yield 55.3%) of the title compound.

REFERENCE EXAMPLE 27

(2R,11aR)-2-(tert-Butyldimethylsilyloxy-1,2,3,10,11,11a-Hexahydro-5H-Pyrrolo[2,1-c][1,4]Benzodiazepin-5-One

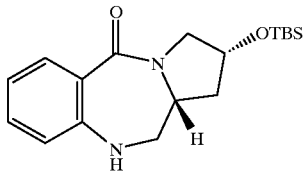

(a-1)

The same procedures used in Method A (a-1) in Reference Example 19 were repeated using cis-4-hydroxy-D-proline methyl ester hydrochloride to give (2R,4R)-4-hydroxy-1-(2-nitrobenzoyl) proline methyl ester. Yield 37.4%.

$^1$H-N.M.R. (CDCl$_3$) δ: 2.17–2.32 (1 H, m), 2.37–2.54 (1 H, m), 3.32–3.92 (6 H, m), 4.32–4.64 (1 H, m), 4.77–4.85 (1 H, m), 7.46–7.80 (3 H, m), 8.17–8.25 (1 H, m); I.R. (KBr) vcm$^{-1}$: 3500, 1750, 1640, 1530, 1430, 1360, 1190, 1090.

(a-2)

The same procedures used in Method A (a-2) in Reference Example 26 were repeated using (2R,4R)-4-hydroxy-1-(2-nitrobenzoyl) proline methyl ester to give (2R,4R)-4-(tert-butyldimethylsilyloxy)-1-(2-nitrobenzoyl) proline methyl ester. Yield 98.6%.

$^1$H-N.M.R. (CDCl$_3$) δ:(−0.02, 0.06, 0.83) (合わせて15 H, 各々s), 2.17–2.51 (2 H, m), 3.13–3.42 (1 H, m), 3.61–3.79 (3 H, m), 3.98–4.11 (1 H, m), 4.34–4.56 (1 H, m), 4.90 (1 H, dd, J=8.8, 4.4 Hz), 7.50–7.79 (3 H, m), 8.11–8.22 (1 H, m); I.R. (neat) vcm$^{-1}$: 2900, 1750, 1640, 1530, 1420, 1350, 1260, 1200, 1100.

(a-3)

The same procedures used in Method A (a-3) in Reference Example 26 were repeated using (2R,4R)-4(tert-butyldimethylsilyloxy)-1-(2-nitrobenzoyl) proline methyl ester to give the title compound. Yield 44.7%.

$^1$H-N.M.R. (CDCl$_3$) δ: 0.08 (6 H, s), 0.88 (9 H, s), 1.75–1.86 (1 H, m), 2.34–2.46 (1 H, m), 3.46–3.54 (1 H, m), 3.67–3.87 (3 H, m), 3.89–4.00 (1 H, m), 4.35–4.43 (1 H, m), 6.55 (1 H, d, J=8.1 Hz), 6.71–6.79 (1 H, m), 7.14–7.22 (1 H, m), 7.97 (1 H, dd, J=8.1, 1.5 Hz); I.R. (neat) vcm$^{-1}$: 3300, 1620, 1600, 1440, 1260, 1120.

REFERENCE EXAMPLE 28

(11aS)-1,2,3,10,11,11a-Hexahydro-5H-Pyrrolo[2,1-c][1,4]Benzodiazepine

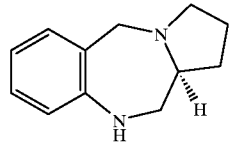

(Method A)

A solution of (11aS)-1,2,3,10,11,11a-hexahydro-5H-pyrrolo[2,1-c][1,4]benzodiazepin-5-one (2.02 g) prepared in Reference Example 24 in tetrahydrofuran (150 ml) was dropwise added to a suspension of lithium aluminum hydride (0.75 g) in tetrahydrofuran (50 ml) over 15 minutes at 0° C. in a nitrogen gas atmosphere and then the mixture was heated under reflux for 15 hours. After ice cooling the reaction solution, 5 ml of chloroform was added thereto, subsequently 20 ml of ethyl acetate and 20 ml of a saturated aqueous ammonium chloride solution were in order added, followed by stirring the resulting mixture for 3 hours. The precipitates thus separated out were filtered off, the filtrate was washed with water, dried and then concentrated under reduced pressure to give 1.88 g (yield 99.9%) of the title compound.

$^1$H-N.M.R. (CDCl$_3$) δ: 1.39–1.54 (1 H, m), 1.69–1.98 (3 H, m), 2.40–2.52 (2 H, m), 2.74 (1 H, dd, J=13.1, 12.7 Hz), 3.12–3.19 (1 H, m), 3.29–3.46 (1 H, m), 3.50 (1H, d, J=13.4 Hz), 3.81 (1 H, d, J=13.4 Hz), 6.71 (1H, d, J=7.6 Hz), 6.81 (1 H, dd, J=7.6, 7.2 Hz), 7.04–7.13 (2 H, m); I.R. (KBr) vcm$^{-1}$: 2960, 2940, 2800, 2780, 1600, 1580, 1480, 1490, 1470, 1290, 1260, 1090, 750.

(Method B)

A solution of (11aS)-1,2,3,10,11,11a-hexahydro-5H-pyrrolo[2,1-c][1]benzodiazepin-5,11-dione (3.0 g) prepared in Reference Example 19 in tetrahydrofuran (100 ml) was dropwise added to a suspension of lithium aluminum hydride (2.1 g) in tetrahydrofuran (50 ml) over 15 minutes at 0° C. in a nitrogen gas atmosphere and then the mixture was heated under reflux for 3 hours. After ice cooling the reaction solution, 150 ml of ether was added thereto, subsequently 2.1 ml of water and 2.1 ml of a 10% sodium hydroxide aqueous solution were in order carefully added and then the mixture was stirred for 30 minutes. Further, 1 ml of water and 1 ml of a 10% sodium hydroxide aqueous solution were added to the mixture, the precipitates formed were removed by filtration, then the filtrate was dried and concentrated under reduced pressure to give 2.3 g (yield 86.7%) of the title compound.

REFERENCE EXAMPLE 29

(11aR)-1,2,3,10,11,11a-Hexahydro-5H-Pyrrolo[2,1-c][1,4]Benzodiazepine

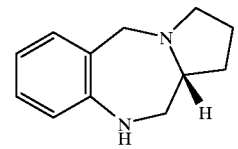

(Method A)

The same procedures used in Method A of Reference Example 28 were repeated using (11aR)-1,2,3,10,11,11a-hexahydro-5H-pyrrolo[2,1-c][1,4]benzodiazepin-5-one obtained in Reference Example 25 to thus give the title compound. Yield 89.5%.

$^1$H-N.M.R. (CDCl$_3$) δ: 1.39–1.54 (1 H, m), 1.69–1.98 (3 H, m), 2.40–2.52 (2 H, m), 2.74 (1 H, dd, J=13.1, 12.7 Hz), 3.12–3.19 (1 H, m), 3.29–3.46 (1 H, m), 3.50 (1H, d, J=13.4 Hz), 3.81 (1H, d, J=13.4 Hz), 6.71 (1H, d, J=7.6 Hz), 6.81 (1 H, dd, J=7.6, 7.2 Hz) 7.04–7.13 (2 H, m); I.R. (KBr) vcm$^{-1}$: 2960, 2940, 2800, 2780, 1600, 1580, 1480, 1490, 1470, 1290, 1260, 1090, 750.

(Method B)

The same procedures used in Method B A-2) of Reference Example 28 were repeated using (11aR)-1,2,3,10,11,11a-hexahydro-5H-pyrrolo[2,1-c][1,4]benzodiazepin-5,11-dione obtained in Reference Example 20 to thus give the title compound. Yield 88–5%.

REFERENCE EXAMPLE 30

(2R,11S-2-Hydroxy-1,2,3,10,11,11a-Hexahydro-5H-Pyrrolo[2,1-c][1,4]Benzodiazepine

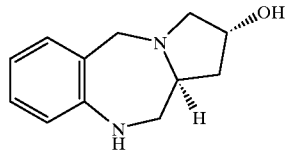

(Method A)

The same procedures used in Method A of Reference Example 28 were repeated using (2R,11aS)-2-(tert-butyldimethylsilyloxy)-1,2,3,10,11,11a-hexahydro-5H-pyrrolo[2,1-][1,4]benzodiazepin-5-one prepared in Reference Example 26 to thus give the title compound. Yield 88.6%.

$^1$H-N.M.R. (CDCl$_3$) δ: 1.78–193 (2 H, m), 2.49 (1H, dd, J=9.8, 4.6 Hz), 2.71 (1 H, dd, J=12.9, 8.9 Hz), 2.90–3.00 (1 H, m), 3.33–3.37 (1 H, m), 3.44 (1 H, dd, J=9.8, 6.1 Hz), 3.77 (2 H, s), 3.78–3.85 (1 H, m), 4.39–4.46 (1 H, m), 6.69 (1H, d, J=8.0 Hz), 6.81 (1 H, d, J=8.0 Hz), 7.04–7.26 (2 H, m); I.R. (KBr) vcm$^{-1}$: 3310, 2830, 1600, 1490, 1380, 1300, 1160, 1080, 1000.

(Method B)

The same procedures used in Method B of Reference Example 28 were repeated using (2R,11aS)-2-hydroxy-1,2,3,10,11,11a-hexahydro-5H-pyrrolo2,1-c][1,4]benzodiazepin-5,11-dione prepared in Reference Example 21 to thus give the title compound. Yield 75.6%.

REFERENCE EXAMPLE 31

(2R,11aR)-2-Hydroxy-1,2,3,10,11,11a-Hexahydro-5H-Pyrrolo[2,1-c][1,4]Benzodiazepine

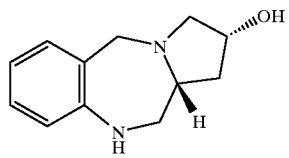

(Method A)

The same procedures used in Method A of Reference Example 28 were repeated using (2R,11aR)-2-(tert-butyldimethylsilyloxy)-1,2,3,10,11,11a-hexahydro-5H-pyrrolo[2,1-c][1,4]benzodiazepin-5-one prepared in Reference Example 27 to thus give the title compound. Yield 89.4%.

$^1$H-N.M.R. (CDCl$_3$) δ: 1.32–1.43 (1 H, m), 2.36–2.49 (3 H, m). 2.63 (1 H, dd, J=10.2, 2.6 Hz), 2.82 (1 H, dd, J=12.6, 8.9 Hz), 3.06 (1 H, d, J=10.2 Hz), 3.30 (1 H, d, J=12.6 Hz), 3.47 (1 H, d, J=13.4 Hz), 3.78 (1 H, d, J=13.4 Hz), 3.89 (1 H, brs), 4.24 (1 H, brs), 6.72 (1 H, d, J=7.8 Hz), 6.81–6.87 (1 H, m), 7.06–7.31 (2 H, m); I.R. (KBr) vcm$^{-1}$: 3360, 2960, 2800, 1610, 1490, 1300, 1090, 1020.

(Method B)

The same procedures used in Method B of Reference Example 28 were repeated using (2R,11aR)-2-hydroxy-1,2,3,10,11,11a-hexahydro-5H-pyrrolo[2,1-c][1,4]benzodiazepin-5,11-dione prepared in Reference Example 23 to thus give the title compound. Yield 68.5%.

REFERENCE EXAMPLE 32

(11aS)-1,2,3,10,11,11a-Hexahydro-5H-Pyrrolo[2,1-c][1,4]Benzodiazepin-5-Thione

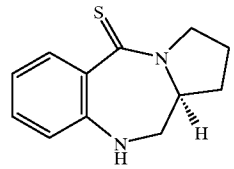

To 50 ml of toluene, there were added 2.02 g of (11aS)-1,2,3,10,11,11a-hexahydro-5H-pyrrolo[2,1-c][1,4]benzodiazepin-5-one prepared in Reference Example 24 and 4.04 g of the Lawesson's reagent and the mixture was heated under reflux for one hour. After cooling the reaction solution, it was concentrated. The resulting residue was subjected to silica gel column chromatography and then eluted with chloroform/acetone (99/1). The elute was concentrated and recrystallized from ethyl acetate to give 1.6 g (yield 73.3%) of the title compound.

$^1$H-N.M.R. (CDCl$_3$) δ: 1.75–1.85 (1 H, m), 2.05–2.35 (4 H, m), 3.65 (1 H, dd, J=15.3, 10.5 Hz), 3.59 (1 H, s), 4.00 (1 H, dt, J=14.0, 8.5 Hz), 4.15–4.25 (2 H, m), 6.60 (1H, d, J=8.0 Hz), 6.92 (1 H, t, J=8.0 Hz), 7.21 (1 H, t, J=8.0 Hz), 8.10 (1 H, d, J=8.0 Hz); I.R. (KBr) vcm$^{-1}$: 3275, 1600, 1480.

REFERENCE EXAMPLE 33

(11aR)-1,2,3,10,11,11a-Hexahydro-5H-Pyrrolo[2,1-c][1,4]Benzodiazepin-5-Thione

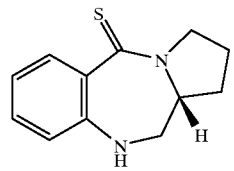

The same procedures used in Reference Example 32 were repeated except for the use of (11aR)-1,2,3,10,11,11a-hexahydro-5H-pyrrolo[2,1-c][1,4]benzodiazepin-5-one obtained in Reference Example 25 to give the title compound. Yield 90%.

$^1$H-N.M.R. (CDCl$_3$) δ: 1.75–1.85 (1 H, m), 2.05–2.35 (4 H, m), 3.65 (1 H, dd, J=15.3, 10.5 Hz), 3.59 (1 H, s), 4.00 (1 H, dt, J=14.0, 8.5 Hz), 4.15–4.25 (2 H, m), 6.60 (1 H, d, J=8.0 Hz), 6.92 (1 H, t, J=8.0 Hz), 7.2 1 (1 H, t, J=8.0 Hz), 8.10 (1 H, d, J=8.0 Hz); I.R. (KBr) vcm$^{-1}$: 3275, 1600, 1480.

REFERENCE EXAMPLE 34

(2S)-1-(2-Nitrophenylsulfonyl) Proline Methyl Ester

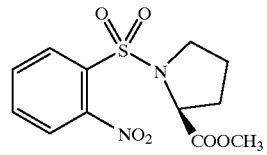

Triethylamine (7.64 g) was added to a suspension of L-proline methyl ester hydrochloride (5 g) and 2-nitrobenzenesulfonyl chloride (7.4 g) in dichloromethane (150 ml), under ice cooling with stirring and the resulting mixture was stirred at room temperature for 17 hours. After water-washing the reaction liquid, it was dried over anhydrous magnesium sulfate and then concentrated. The resulting residue was subjected to silica gel column chromatography and then eluted with ethyl acetate/hexane (1/3) to give 9.12 g (yield 96.1%) of the title compound.

$^1$H-N.M.R. (CDC$_3$) δ: 1.92–2.15 (3 H, m), 2.19–2.36 (1 H, m), 3.51–3.69 (5 H, m), 4.59 (1 H, dd, J=8.1, 2.9 Hz), 7.61–7.74 (3 H, m), 8.07–8.15 (1 H, m); I.R. (KBr) vcm$^{-1}$: 1760, 1550, 1380, 1350, 1210, 1160.

REFERENCE EXAMPLE 35

(11aS)-1,2,3,10,11,11a-Hexahydro-Pyrrolo[1,2-b][1,2,]Benzothiadiazepin-5.5-Dioxide

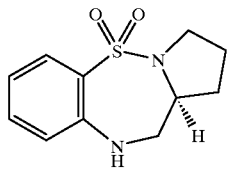

The same procedures used in Reference Example 24 (Method A) were repeated using (2S)-1-(2-nitrophenylsulfonyl) proline methyl ester obtained in Reference Example 34 to give the title compound. Yield 35.0%.

$^1$H-N.M.R. (CDCl$_3$) δ: 1.88–2.24 (3 H, m), 2.99–3.11 (2 H, m), 3.50–3.58 (1 H, m), 3.95–4.04 (1 H, m), 4.32–4.43 (2 H, m), 6.68 (1 H, dd, J=8.3, 1.2 Hz), 6.83–6.90 (1 H, m), 7.19–7.25 (1 H, m), 7.77 (1 H, dd, J=8.1, 1.5 Hz); I.R. (KBr) vcm$^{-1}$: 3350, 1600, 1510, 1490, 1320, 1150, 1080.

REFERENCE EXAMPLE 36

(11aS)-10-(4-Nitrobenzoyl)-1,2,3,10,11,11a-Hexahydro-Pyrrolo[1,2-b][1,2,5]Benzothiadiazepin-5,5-Dioxide

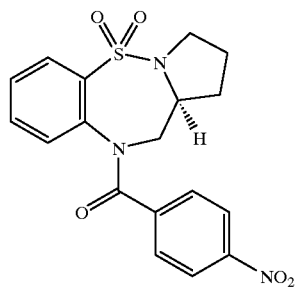

To a suspension of a 60% sodium hydride (0.18 g) in anhydrous N,N-dimethylformamide (5 ml), there was gradually added, under ice cooling, a solution of 0.6 g of (11aS)-1,2,3,10,11,11a-hexahydro-pyrrolo[1,2-b][1,2,5] benzothiadiazepin-5,5-dioxide prepared in Reference Example 35 in 10 ml of anhydrous N,N-dimethylformamide. After stirring the mixture at 60° C. for 2 hours, the reaction liquid was cooled, poured into ice water and then extracted with ethyl acetate. The resulting organic phase was washed with water, dried over anhydrous magnesium sulfate and concentrated. The resulting residue was subjected to silica gel column chromatography and eluted with chloroform/methanol (19/1). The elute was recrystallized from ethyl acetate-hexane to thus give 0.37 g (yield 37.5%) of the title compound.

$^1$H-N.M.R. (CDCl$_3$) δ: 1.72–2.20 (3 H, m), 2.30–2.46 (1 H, m), 2.74 (1 H, dd, J=13.9, 11.5 Hz), 3.04–3.16 (1 H, m), 3.63–3.73 (1 H, m), 4.45–4.57 (1 H, m), 4.85–4.94 (1 H, m), 6.81 (1 H, d, J=8.1 Hz), 7.25–7.44 (2 H, m), 7.66 (2 H, d, J=8.8 Hz), 7.98–8.06 (3 H, m); I.R. (KBr) vcm$^{-1}$: 3400, 1700, 1640, 1530, 1360, 1340, 1320, 1160.

REFERENCE EXAMPLE 37

(11aS)-10-(4-Aminobenzoyl)-1,2,3,10,11,11a-Hexahydro-Pyrrolo[1,2-b][2,5]Benzothiadiazepin-5,5-Dioxide

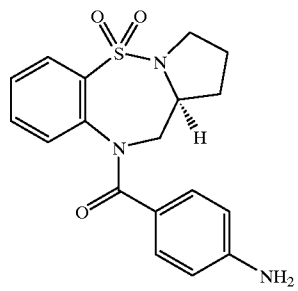

The compound (11aS)-10-(4-nitrobenzoyl)-1,2,3,10,11,11a-hexahydro-pyrrolo[1,2-b][1,2,5]benzothiadiazepin-5,5-dioxide (0.35 g) obtained in Reference Example 36 was dissolved in a mixed solvent containing 70 ml of methanol and 20 ml of ethyl acetate and the compound was catalytically reduced at ordinary temperature in the presence of 0.3 g of a 10% palladium-carbon catalyst. After the completion of the reaction, the catalyst was removed and then the reaction solution was concentrated to dryness to thus give 0.29 g (yield 89.8%) of the title compound.

$^1$H-N.M.R. (CDCl$_3$) δ: 1.66–2.02 (3 H, m), 2.12–2.28 (1 H, m) 2.56–2.78 (1 H, m), 2.91–3.03 (1 H, m), 3.37–3.49 (1 H, m), 4.02–4.15 (1 H, m), 4.71–4.83 (1 H, m), 5.74 (2 H, brs), 6.28 (2 H, d, J=8. 6 Hz), 6.92–7.04 (3 H, m), 7.40–7.47 (2 H, m), 7.86–7.93 (1 H, m); I.R. (KBr) vcm$^{-1}$: 3400, 1700, 1600, 1520, 1260, 1160.

REFERENCE EXAMPLE 38

1-Tosyl-L-Proline

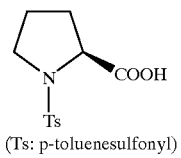

(Ts: p-toluenesulfonyl)

To a solution of 7 g of L-proline in 120 ml of a 2N aqueous sodium hydroxide solution, there was added 11.8 g of p-toluenesulfonyl chloride and the mixture was heated to 70° C. for one hour with stirring. After the reaction solution was ice-cooled, it was acidified with hydrochloric acid and then extracted with ethyl acetate. The resulting organic phase was washed with water, dried over anhydrous magnesium sulfate and then concentrated to give 16.1 g (yield 98.3%) of the title compound.

¹H-N.M.R. (CDCl₃) δ: 1.70–2.02 (3 H, m), 2.2 1–2.22 (1 H, m), 2.05 (3 H, s), 3.20–3.31 (1 H, m), 3.48–3.58 (1 H, m), 4.26 (1 H, dd, J=8.1, 3.7 Hz), 7.35 (2 H, d, J=8.4 Hz), 7.77 (2 H, d, J=8.4 Hz); I.R. (neat) vcm⁻¹: 2960, 1720, 1320, 1155, 1090.

REFERENCE EXAMPLE 39

1-Tosyl-D-Proline

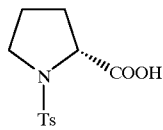

The same procedures used in Reference Example 38 were repeated using D-proline as a starting material to give the title compound. Yield 98.5%.

¹H-N.M.R. (CDCl₃) δ: 1.70–2.02 (3 H, m), 2.21–2.22 (1 H, m), 2.05 (3 H, s), 3.20–3.31 (1 H, m), 3.48–3.58 (1 H, m), 4.26 (1 H, dd, J=8.1, 3.7 Hz), 7.35 (2 H, d, J=8.4 Hz), 7.77 (2 H, d, J=8.4 Hz); I.R. (neat) vcm⁻¹: 2960, 1720, 1320, 1155, 1090.

REFERENCE EXAMPLE 40

(2S, 4R)-4-(tert-Butyldimethylsilyloxy)-1-(2-Nitrophenyl) Proline Methyl Ester

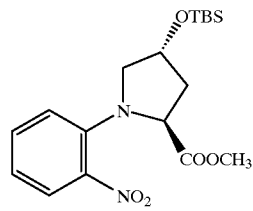

To a solution of (2S, 4R)-4-hydroxy-1-(2-nitrophenyl) proline methyl ester (7.69 g) obtained in Reference Example 7 and imidazole (4.55 g) in anhydrous N,N-dimethylformamide (80 ml), there was added, at room temperature, 5.19 g of tert-butyldimethylsilyl chloride. After stirring the reaction solution at room temperature for 15 hours, it was concentrated. Water and ethyl acetate were added to the residue obtained through the concentration and the organic phase was separated. The organic phase was washed with water, dried over anhydrous magnesium sulfate and then concentrated. The resulting residue was subjected to silica gel column chromatography and then eluted with ethyl acetate/hexane (1/4) to give 9.62 g (yield 87.5%) of the title compound.

¹H-N.M.R. (CDCl₃) δ: −0.03 (3 H, s), 0.04 (3 H, s), 0.78 (9 H, s), 2.11–2.21 (1 H, m), 2.31–2.41 (1 H, m), 2.65 (1 H, d, J=11.0 Hz), 3.72 (3 H, s), 3.80 (1 H, dd, J=9.6, 3.7 Hz), 4.48 (1 H, brs), 4.60–4.68 (1 H, m), 6.77–6.99 (2 H, m), 7.32–7.42 (1 H, m), 7.77 (1 H, dd, J=8.1, 1.5 Hz); I.R. (neat) vcm⁻¹: 2950, 1755, 1740, 1605, 1520, 1360, 1285, 1180.

REFERENCE EXAMPLE 41

(2R,4R)-4-(tert-Butyldimethylsilyloxy)-1-(2-Nitrophenyl) Proline Methyl Ester

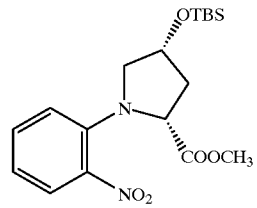

The same procedures used in Reference Example 40 were repeated using (2R,4R)-4-hydroxy-1-(2-nitrophenyl) proline methyl ester obtained in Reference Example 6 to thus give the title compound. Yield 98.3%.

¹H-N.M.R. (CDCl₃) δ: 0.06 (6 H, s), 0.87 (9 H, s), 2.10–2.22 (1 H, m), 2.50–2.63 (1 H, m), 3.25 (1 H, dd, J=9.9, 6.6 Hz), 3.45 (1 H, dd, J=9.9, 6.6 Hz), 3.66 (3 H, s), 4.37–4.50 (2 H, m), 6.77–6.88 (2 H, m), 7.33–7.42 (1 H, m), 7.70 (1 H, dd, J=8.1, 1.5 Hz); I.R. (neat) vcm⁻¹: 2950, 1755, 1605, 1515, 1380, 1285, 1210, 1120.

REFERENCE EXAMPLE 42

(2S)-1-Tosyl-2-Pyrrolidinyl Methyl Alcohol

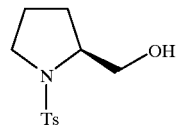

A solution of 1-tosyl-L-proline (17.8 g) prepared in Reference Example 38 in anhydrous ether (80 ml) was dropwise added to a suspension of lithium aluminum hydride (3.76 g) in anhydrous ether (80 ml) over 30 minutes with ice-cooling. After stirring the reaction liquid at room temperature for one hour, 100 ml of ethyl acetate was added thereto and the resulting mixture was stirred for additional 16 hours. The insolubles formed was filtered off through a Celite layer, the organic phase obtained was washed with water and dried over anhydrous magnesium sulfate. The organic phase was concentrated, then the resulting residue was subjected to silica gel column chromatography and eluted with chloroform/ethyl acetate (98/2) to give 8.96 g (yield 53.1%) of the title compound.

¹H-N.M.R. (CDCl₃) δ: 1.39–1.52 (1 H, m), 1.64–1.85 (3 H, m), 2.44 (3 H, s), 2.73–2.80 (1 H, m), 3.22–3.32 (1 H, m), 3.41–3.51 (1 H, m), 3.60–3.73 (3 H, m), 7.70 (2 H, d, J=8.4 Hz), 7.74 (2 H, d, J=8.4 Hz); I.R. (KBr) vcm⁻¹: 3530, 1590, 1335, 1150, 1090, 1030.

REFERENCE EXAMPLE 43

(2R)-1-Tosyl-2-Pyrrolidinyl Methyl Alcohol

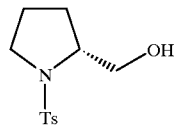

The same procedures used in Reference Example 42 were repeated using 1-tosyl-D-proline obtained in Reference Example 39 to give the title compound. Yield 72.4%.

$^1$H-N.M.R. (CDCl$_3$) δ: 1.39–1.52 (1 H, m), 1.64–1.85 (3 H, m), 2.44 (3 H, s), 2.73–2.80 (1 H, m), 3.22– 3.32 (1 H, m), 3.41–3.51 (1 H, m), 3.60–3.73 (3 H, m), 7.70 (2 H, d, J=8.4 Hz), 7.74 (2 H, d, J=8.4 Hz); I.R. (KBr) νcm$^{-1}$: 3530, 1590, 1335, 1150, 1090, 1030.

REFERENCE EXAMPLE 44

(2S, 4R)-[4-(tert-Butyldimethylsilyloxy)-1-(2-Nitrophenyl)-2-Pyrrolidinyl]Methyl Alcohol

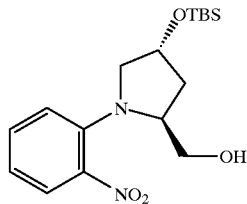

To a solution of (2S, 4R)-4-(tert-butyldimethylsilyloxy)-1-(2-nitrophenyl) proline methyl ester (9.62 g) obtained in Reference Example 40 ml anhydrous tetrahydrofuran (300 ml), there was added, in small portions, 0.96 g of lithium borohydride under ice-cooling. After stirring the reaction liquid at room temperature over 15 hours, it was poured into ice water and then extracted with ethyl acetate. The organic phase thus obtained was washed with water, dried over anhydrous magnesium sulfate and then concentrated. The residue thus obtained was subjected to silica gel column chromatography and then eluted with ethyl acetate/hexane (1/9) to give 8.55 g (yield 96.1%) of the title compound.

$^1$H-N.M.R. (CDCl$_3$) δ: −0.09 (3 H, s), 0.03 (3 H, s), 0.76 (9 H, s), 1.85 (1 H, dd, J=10.6, 2.6 Hz), 1.97–2.08 (1 H, m), 2.16–2.27 (1 H, m), 2.49 (1 H, dd, J=10.6, 2.6 Hz), 3.49–3.60 (1 H, m), 3.65 (1 H, dd, J=10.6, 2.9 Hz), 3.95 (1 H, dt, J=11.7, 2.9 Hz), 4.33–4.46 (1 H, m), 682–6.89 (1 H, m), 7.16 (1 H, d, J=8.1 H z), 7.38–7.45 (1 H, m), 7.81 (1 H, d, J=8.1, 1.8 Hz); I.R. (neat) νcm$^{-1}$: 2920, 1605, 1510, 1360, 1280, 1075, 1035.

REFERENCE EXAMPLE 45

(2R,4R)-[4-(tert-Butyldimethylsilyloxy)-1-(2-Nitrophenyl)-2-Pyrrolidinyl]Methyl Alcohol

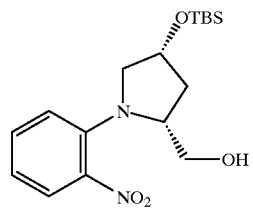

The same procedures used in Reference Example 44 were repeated using (2R,4R)-4-(tert-butyldimethylsilyloxy)-1-(2-nitrophenyl) proline methyl ester obtained in Reference Example 41 to give the title compound. Yield 94.7%.

$^1$H-N.M.R. (CDCl$_3$) δ: 0.05 (3 H, s), 0.06 (3 H, s), 0.88 (9 H, s), 2.01–2.13 (1 H, m), 2.20 (1 H, brs), 2.27–2.38 (1 H, m), 2.90 (1 H, dd, J=9.9, 6.6 Hz), 3.39 (1 H, dd, J=9.9, 7.0 Hz), 3.52–3.61 (1 H, m), 3.81 (1 H, dd, J=11.7, 3.7 Hz), 4.11–4.21 (1 H, m), 4.29–4.40 (1 H, m), 6.79–6.86 (1 H, m), 7.08 (1 H, d, J=7.7 H z), 7.37–7.42 (1 H, m), 7.75 (1 H, dd, J=8.1, 1.5 Hz); I.R. (neat) νcm$^{-1}$: 9920, 1605, 1510, 1370, 1280, 1250, 1120, 835.

REFERENCE EXAMPLE 46

(2S)-1-Tosyl-2-Pyrrolidinyl Methyl p-Toluene-sulfonate

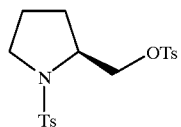

To 100 ml of anhydrous pyridine, there were added 8.96 g of (2S)-1-tosyl-2-pyrrolidinyl methyl alcohol obtained in Reference Example 42 and 12.9 g of p-toluenesulfonyl chloride and the resulting mixture was stirred at room temperature for 15 hours. The reaction solution was poured into ice water and extracted with ethyl acetate. The resulting organic phase was washed with 4N hydrochloric acid, water, 5% aqueous sodium carbonate solution and water in this order and then dried over anhydrous magnesium sulfate. After concentration, the resulting residue was subjected to silica gel column chromatography and then eluted with benzene/ethyl acetate (9/1) to give 6.93 g (yield 48.2%) of the title compound.

$^1$H-N.M.R. (CDCl$_3$) δ: 1.56–1.69 (2 H, m), 1.73–1.93 (2 H, m), 2.43 (3 H, s), 2.47 (3 H, s), 2.99–3.09 (1 H, m), 3.34–3.44 (1 H, m), 3.70–3.80 (1 H, m), 3.95 (1 H, dd, J=9.9, 8.4 Hz), 4.25 (1 H, dd, J=9.9, 3.7 Hz), 7.31 (2 H, d, J=8.1 Hz), 7.37 (2 H, d, J=8.1 Hz), 7.65 (2 H, d, J=8.4 Hz), 7.02 (2 H, d, J=8.4 Hz); I.R. (neat) νcm$^{-1}$: 2980, 1600, 1350, 1180, 1160, 1100, 1070.

REFERENCE EXAMPLE 47

(2R)-1-Tosyl-2-Pyrrolidinyl Methyl p-Toluene-sulfonate

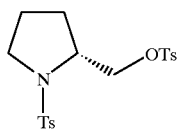

The same procedures used in Reference Example 46 were repeated using (2R)-1-tosyl-2-pyrrolidinyl methyl alcohol obtained in Reference Example 43 to thus give the title compound. Yield 99.1%.

$^1$H-N.M.R. (CDCl$_3$) δ: 1.56–1.69 (2 H, m), 1.73–1.93 (2 H, m), 2.43 (3 H, s), 2.47 (3 H, s), 2.99–3.09 (1 H, m), 3.34–3.44 (1 H, m), 3.70–3.80 (1 H, m), 3.95 (1 H, dd, J=9.9, 8.4 Hz), 4.25 (1 H, dd, J=9.9, 3.7 Hz), 7.31 (2 H, d, J=8.1 Hz), 7.37 (2 H, d, J=8.1 Hz), 7.65 (2 H, d, J=8.4 Hz), 7.02 (2 H, d, J=8.4 Hz); I.R. (neat) vcm$^{-1}$: 2980, 1600, 1350, 1180, 1160, 1100, 1070.

REFERENCE EXAMPLE 48

(2S, 4R)-[4-(tert-Butyldimethylsilyloxy)-1-1-Nitrophenyl)-2-Pyrrolidinyl] Methyl p-Toluenesulfonate

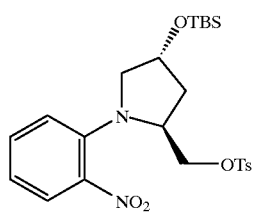

To 100 ml of anhydrous pyridine, there were added 8.34 g of (2S, 4R)-[4-(tert-butyldimethylsilyloxy)-1-(2-nitrophenyl)-2-pyrrolidinyl] methyl alcohol obtained in Reference Example 44 and 8.7 g of p-toluenesulfonyl chloride and the resulting reaction solution was stirred at room temperature for 15 hours. The reaction solution was poured into ice water and then extracted with ethyl acetate. The resulting organic phase was washed with 4N hydrochloric acid, water, a 5% aqueous sodium carbonate solution and water in this order and then dried over anhydrous magnesium sulfate. After concentration, the resulting residue was subjected to silica gel column chromatography and then eluted with ethyl acetate/hexane (1/1) to give 7.73 g (yield 64.5%) of the title compound.

$^1$H-N.M.R. (CDCl$_3$) δ: –0.07 (3 H, s), 0.01 (3 H, s), 0.73 (9 H, s), 1.82–1.93 (1 H, m), 2.16–2.61 (1 H, m), 2.37–2.48 (4 H, m), 3.62 (1 H, dd, J=11.0, 2.9 Hz), 3.90 (1 H, dd, J=10.3, 7.0 Hz), 4.22 (1 H, dd, J=11.0, 2.9 Hz), 4.33–4.47 (2 H, m), 6.77–6.85 (1 H, m), 6.97 (1 H, d, J=8.4 Hz), 7.24 (2 H, d, J=7.7 Hz), 7.30–7.38 (1 H, m), 7.70 (2 H, d, J=7.7 Hz), 7.74 (1H, dd, J=8.1, 1.8 Hz); I.R. (neat) vcm$^{-1}$: 2950, 1605, 1520, 1515, 1305, 1190, 1175, 1025, 830.

REFERENCE EXAMPLE 49

(2R,4R)-[4-(tert-Butyldimethylsilyloxy)-1-(2-Nitrophenyl)-2-Pyrrolidinyl] Methyl p-Toluenesulfonate

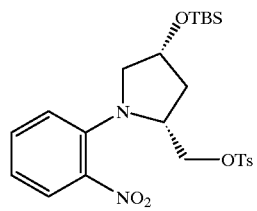

To 200 ml of dichloromethane, there were added 11.23 g of (2R,4R)-4-(tert-butyldimethylsilyloxy)-1-(2-nitrophenyl)-2-pyrrolidinyl methyl alcohol obtained in Reference Example 45 and 8.67 g of p-toluenesulfonyl chloride and then 8.4 g of triethylamine and 1.93 g of 4-(N,N-dimethylamino) pyridine were added to the resulting solution under ice-cooling. After stirring the reaction solution at room temperature for 4 hours, it was washed with a 5% aqueous citric acid solution and then with water. The resulting organic phase was dried over anhydrous magnesium sulfate and then concentrated to give 15.96 g (yield 98.8%) of the title compound.

$^1$H-N.M.R. (CDCl$_3$) δ: 0.02 (3 H, s), 0.03 (3 H, s), 0.85 (9 H, s), 1.78–1.90 (1 H, m), 2.31–2.45 (4 H, m), 2.87 (1 H, dd, J=10.3, 6.6 Hz), 3.32 (1 H, dd, J=9.9, 6.6 Hz), 3.93 (1 H, dd, J=9.9, 7.0 Hz), 4.10–4.36 (3 H, m), 6.77–6.85 (1 H, m), 7.00 (1 H, d, J=8.1 Hz), 7.24–7.31 (2 H, m), 7.32–7.39 (1 H, m), 7.65–7.74 (3 H, m); I.R. (neat) vcm$^{-1}$: 3400, 1605, 1515, 1360, 1175, 1130, 855.

REFERENCE EXAMPLE 50

(2S)-2-(1-Tosylpyrrolidin-2-yl) Acetonitrile

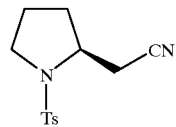

To 50 ml of anhydrous dimethyl sulfoxide, there were added 6.92 g of (2S)-1-tosyl-2-pyrrolidinyl methyl p-toluenesulfonate prepared in Reference Example 46 and 1.61 g of potassium cyanide and the resulting mixture was heated with stirring at 60° C. for 4 hours. After cooling the reaction solution, it was poured into a saturated aqueous solution of ammonium chloride, followed by extraction with chloroform. The resulting organic phase was washed with water, dried over anhydrous magnesium sulfate and then concentrated to give 4.35 g (yield 97.3%) of the title compound.

$^1$H-N.M.R. (CDCl$_3$) δ: 1.55–1.66 (1 H, m), 1.82–2.00 (3 H, m), 2.45 (3 H, s), 2.70–2.93 (2 H, m), 3.12–3.23 (1 H, m), 3.45–3.5 4 (1 H, m), 3.76–3.85 (1 H, m), 7.35 (2 H, d, J=8.4 Hz), 7.73 (2 H, d, J=8.4 Hz); I.R. (neat) vcm$^{-1}$: 2960, 2250, 1600, 1340, 1160, 1090, 1035.

REFERENCE EXAMPLE 51

(2E)-2-(1-Tosylpyrrolidin-2-yl) Acetonitrile

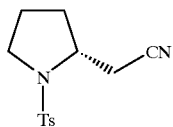

The same procedures used in Reference Example 50 were repeated except for using (2R)-1-tosyl-2-pyrrolidinyl methyl p-toluenesulfonate prepared in Reference Example 47 to give the title compound. Yield 91.60%.

$^1$H-N.M.R. (CDCl$_3$) δ: 1.55–1.66 (1 H, m), 1.82–2.00 (3 H, m), 2.45 (3 H, s), 2.70–2.93 (2 H, m), 3.12–3.23 (1 H, m), 3.45–3.54 (1 H, m), 3.76–3.85 (1 H, m), 7.35 (2 H, d, J=8.4 Hz), 7.73 (2 H, d, J=8.4 Hz); I.R. (neat) cm$^{-1}$: 2960, 2250, 1600, 1340, 1160, 1090, 1035.

REFERENCE EXAMPLE 52

(2R,4R)-2-[4-(tert-Butyldimethylsilyloxy)-1-(2-Nitrophenyl) Pyrrolidin-2-yl]Acetonitrile

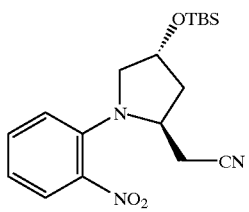

The same procedures used in Reference Example 50 were repeated except for using (2S, 4R)-[4-(tert-butyldimethylsilyloxy)-1-(2-nitrophenyl)-2-pyrrolidinyl] methyl p-toluenesulfonate prepared in Reference Example 48 to give the title compound. Yield 80.4%.

$^1$H-N.M.R. (CDCl$_3$) δ: −0.06 (3 H, s), 0.04 (3 H, s), 0.76 (9 H, s), 2.01 (1 H, ddd, J=12.8, 9.9, 3.3 Hz), 2.31–2.41 (1 H, m), 2.51–2.62 (2 H, m), 2.81 (1 H, dd, J=6.9, 3.3 Hz), 3.79 (1 H, dd, J=11.0, 3.3 Hz), 4.36–4.47 (2 H, m), 6.87–6.95 (1 H, m), 7.01 (1 H, d, J=8.1 Hz), 7.46 (1 H, ddd, J=8.4, 7.0, 1.5 Hz), 7.82 (1 H, dd, J=8.4, 1.5 Hz); I.R. (neat) vcm$^{-1}$: 2920, 2250, 1605, 1520, 1515, 1485, 1360, 1285, 1170, 1095, 1020.

REFERENCE EXAMPLE 53

(2S, 4R)-2-[4-(tert-Butyldimethylsilyloxy)-1-(2-Nitrophenyl) Pyrrolidin-2-yl]Acetonitrile

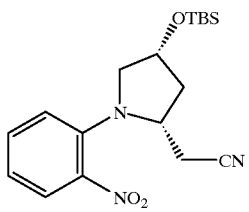

The same procedures used in Reference Example 50 were repeated except for using (2R,4R)-[4-(tert-butyldimethylsilyloxy)-1-(2-nitrophenyl)-2-pyrrolidinyl] methyl p-toluenesulfonate prepared in Reference Example 49 to give the title compound. Yield 62.5%.

$^1$H-N.M.R. (CDCl$_3$) δ: 0.06 (3 H, s), 0.08 (3 H, s), 0.89 (9 H, s), 2.04 (1 H, ddd, J=12.7, 6.8, 6. 3 Hz), 2.45–2.5 6 (1 H, m), 2.64 (1 H, dd, J=16.8, 8.0 Hz), 2.73 (1 H, dd, J=16.8, 4.0 Hz), 3.07 (1 H, dd, J=10.0, 6.3 Hz), 3.45 (1 H, dd, J=10.0, 6.3 Hz), 4.20–4.30 (1 H, m), 4.40 (1 H, quint, J=6.3 Hz), 6.89 (1 H, t, J=7.8 Hz), 6.97 (1 H, d, J=7.8 Hz), 7.45 (1 H, t, J=7.8 Hz), 7.73 (1 H, d, J=7.8 Hz); I.R. (KBr) vcm$^{-1}$: 2250, 610, 1520, 3000, 1130.

REFERENCE EXAMPLE 54

(2S)-2-(1-Tosylpyrrolidin-2-yl) Acetic Acid

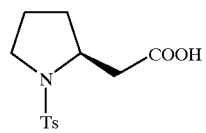

Concentrated hydrochloric acid (20 ml) was added to a solution of (2S)-2-(1-tosylpyrrolidin-2-yl) acetonitrile (4.35 g) prepared in Reference Example 50 in acetic acid (4 ml) and then the reaction solution was heated under reflux for 3 hours. After cooling the reaction solution, it was poured into ice water and then extracted with ether. The resulting organic phase was washed with water, dried over anhydrous magnesium sulfate and then concentrated. The resulting residue was subjected to silica gel column chromatography and then eluted with chloroform/methanol (99/1) to give 6.93 g (yield 48.2%) of the title compound.

$^1$H-N.M.R. (CDCl$_3$) δ: 1.47–1.88 (4 H, m), 2.44 (3 H, s), 2.56 (1 H, dd, J=16.1, 9.8 Hz), 3.06–3.20 (2 H, m), 3.42–3.51 (1 H, m), 3.88–3.98 (1 H, m), 7.33 (2 H, d, J=8.3 Hz), 7.74 (2 H, d, J=8.3 Hz); I.R. (neat) vcm$^{-1}$: 3330, 1720, 1340, 1160, 1095.

REFERENCE EXAMPLE 55

(2R)-2-(1-Tosylpyrrolidin-2-yl) Acetic Acid

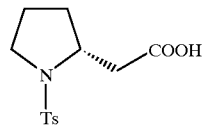

The same procedures used in Reference Example 54 were repeated using (2R)-2-(1-tosylpyrrolidin-2-yl) acetonitrile obtained in Reference Example 51 to give the title compound. Yield 65.9%.

$^1$H-N.M.R. (CDCl$_3$) δ: 1.47–1.88 (4 H, m), 2.44 (3 H, s), 2.56 (1 H, dd, J=16.1, 9.8 Hz), 3.06–3.20 (2 H, m), 3.42–3.51 (1 H, m), 3.88–3.98 (1 H, m), 7.33 (2 H, d, J=8.3 Hz), 7.74 (2 H, d, J=8.3 Hz); I.R. (KBr) vcm$^{-1}$: 3330, 1720, 1320, 1160, 1095.

REFERENCE EXAMPLE 56

(2S)-2-Pyrrolidinyl Acetic Acid Hydrobromic Acid

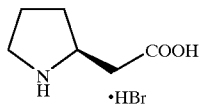

(2S)-2-(1-Tosylpyrrolidin-2-yl) acetic acid (1.2 g) obtained in Reference Example 54 was added to 10 ml of a 25% solution of hydrobromic acid in acetic acid and the reaction solution was stirred in a closed container at room temperature for 18 hours. Then the reaction solution was poured into 30 ml of cold anhydrous ether. The crystals precipitated were filtered off, washed with ether and dried to give 0.43 g (yield 47.7%) of the title compound.

$^1$H-N.M.R. (DMSO-$d_6$) δ: 1.47–1.64 (1 H, m), 1.74–1.98 (2 H, m), 2.03–2.18 (1 H, m), 2.74 (2 H, d, J=6.4 H z), 3.15 (2 H, brs), 3.71 (1 H, brs), 8.5 4 (1 H, brs), 8.95 (1 H, brs); I.R. (KBr) vcm$^{-1}$: 3400, 2980, 1720, 1410, 1220.

REFERENCE EXAMPLE 57

(2R)-2-Pyrrolidinyl Acetic Acid Hydrobromic Acid Salt

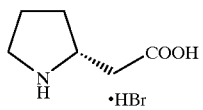

The same procedures used in Reference Example 56 were repeated using (2R)-2-(1-tosylpyrrolidin-2-yl) acetic acid prepared in Reference Example 55 to thus give the title compound. Yield 52.6%.

$^1$H-N.M.R. (DMSO-$d_6$) δ: 1.47–1.64 (1 H, m), 1.74–1.98 (2 H, m), 2.03–2.18 (1 H, m), 2.74 (2 H, d, J=6.4 H z), 3.15 (2 H, brs), 3.71 (1 H, brs), 8.54 (1 H, brs), 8.95 (1 H, brs); I.R. (KBr) vcm$^{-1}$: 3400, 2980, 1720, 1410, 1220.

REFERENCE EXAMPLE 58

(2S)-2-[1-(2-Nitrophenyl) Pyrrolidin-2-yl]Acetic Acid

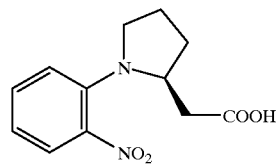

The same procedures used in Reference Example 1 were repeated using (2S)-2-pyrrolidinyl acetic acid hydrobromic acid salt prepared in Reference Example 56 and 1-fluoro-2-nitrobenzene to thus give the title compound. Yield 83.4%.

$^1$H-N.M.R. (CDCl$_3$) δ: 1.73–1.91 (2 H, m), 1.95–2.06 (1 H, m), 2.38–2.49 (2 H, m), 2.70–2.80 (1 H, m), 2.92 (1 H, dd, J=15.8, 2.9 Hz), 3.51–3.62 (1 H, m), 4.18–4.30 (1 H, m), 6.81–6.88 (1 H, m), 7.02 (1 H, d, J=8.1 Hz), 7.39–7.47 (1 H, m), 7.79 (1 H, dd, J=8.4, 1.5 Hz); I.R. (KBr) vcm$^{-1}$: 2960, 1710, 1605, 1515, 1365, 1280, 1170.

REFERENCE EXAMPLE 59

(2R)-2-[1-(2-Nitrophenyl) Pyrrolidin-2-yl]Acetic Acid

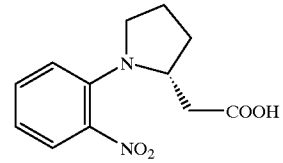

The same procedures used in Reference Example 1 were repeated using (2R)-2-pyrrolidinyl acetic acid hydrobromic acid salt prepared in Reference Example 57 and 1-fluoro-2-nitrobenzene to thus give the title compound. Yield 80.1%.

$^1$H-N.M.R. (CDCl$_3$) δ: 1.73–1.91 (2 H, m), 1.95–2.06 (1 H, m), 2.38–2.49 (2 H, m), 2.70–2.80 (1 H, m), 2.92 (1 H, dd, J=15.8, 2.9 Hz), 3.51–3.62 (1 H, m), 4.18–4.30 (1 H, m), 6.81–6.88 (1 H, m), 7.02 (1 H, d, J=8.1 Hz), 7.39–7.47 (1 H, m), 7.79 (1 H, dd, J=8.4, 1.5 Hz); I.R. (KBr) vcm$^{-1}$: 2960, 1710, 1605, 1515, 1365, 1280, 1170.

REFERENCE EXAMPLE 60

(3aS)-2,3,3a,4,5,6-Hexahydro-1H-Pyrrolo[1,2-a][1.5]Benzodiazepin-5-One

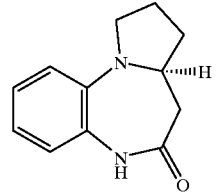

The compound (2S)-2-[1-(2-nitrophenyl) pyrrolidin-2-yl] acetic acid (0.42 g) prepared in Reference Example 58 was catalytically reduced at ordinary temperature in the presence of 0.3 g of a 10% palladium-carbon catalyst in 80 ml of methanol. After the completion of the reaction, the catalyst was removed and then the reaction solution was concentrated to dryness to obtain 0.32 g (yield 85.1%) of the title compound.

$^1$H-N.M.R. (CDCl$_3$) δ: 1.64–1.76 (1 H, m), 1.90–2.10 (2 H, m), 2.13–2.24 (1 H, m), 2.65–2.80 (2 H, m), 3.28–3.49 (2 H, m), 3.82–3.94 (1 H, m), 6.67–6.83 (3 H, m), 6.99–7.07 (1 H, m), 7.54 (1 H, brs); I.R. (KBr) vcm$^{-1}$: 3050, 1660, 1520, 1505, 1440, 1420, 1390.

REFERENCE EXAMPLE 61

(3aR)-2,3,3a,4,5,6-Hexahydro-1H-Pyrrolo[1,2-a][1,5]Benzodiazepin-5-One

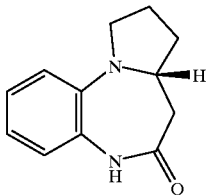

The same procedures used in Reference Example 60 were repeated using (2R)-2-[1-(2-nitrophenyl) Pyrrolidin-2-yl] acetic acid prepared in Reference Example 59 to thus give the title compound. Yield 42.7%.

$^1$H-N.M.R. (CDCl$_3$) δ: 1.64–1.76 (1 H, m), 1.90–2.10 (2 H, m), 2.13–2.24 (1 H, m), 2.65–2.80 (2 H, m), 3.28–3.49 (2 H, m), 3.82–3.94 (1 H, m), 6.67–6.83 (3 H, m), 6.99–7.07 (1 H, m), 7.54 (1 H, brs); I.R. (KBr) vcm$^{-1}$: 3050, 1660, 1520, 1505, 1440, 1420, 1390.

REFERENCE EXAMPLE 62

(3aS)-2,3,3a,4,5,6-Hexahydro-1H-Pyrrolo[1,2-a][1,5]Benzodiazpine

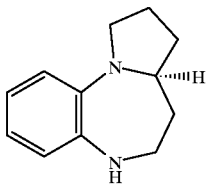

To a suspension of lithium aluminum hydride (0.14 g) in tetrahydrofuran (10 ml), there was dropwise added, with ice-cooling, a solution of (3aS)-2,3,3a,4,5,6-hexahydro-1H-pyrrolo[1,2-a][1,5]benzodiazepin-5-one (0.36 g) prepared in Reference Example 60 in anhydrous tetrahydrofuran (8 ml) over 30 minutes. After refluxing with heating for one hour, 100 ml of ethyl acetate was added to the reaction solution with ice-cooling and the mixture was further stirred at room temperature for 15 hours. Water was added to the reaction solution and the insolubles separated out were filtered off through a Celite layer. The resulting organic phase was washed with water, dried over anhydrous magnesium sulfate and then concentrated. The resulting residue was subjected to silica gel column chromatography and eluted with chloroform/ethyl acetate (991) to give 0.33 g (yield 98.5%) of the title compound.

$^1$H-N.M.R. (CDCl$_3$) δ: 1.62–1.76 (2 H, m), 1.85–2.04 (4 H, m), 2.76–2.87 (1 H, m), 3.17–3.33 (3 H, m), 3.41–3.52 (1 H, m), 6.60–6.88 (4 H, m); I.R. (neat) vcm$^{-1}$: 2940, 1590, 1490, 1315, 1150

REFERENCE EXAMPLE 63

(3aR)-2,3,3a,4,5,6-Hexahydro-1H-Pyrrolo[1,2-a][1.5]Benzodiazepine

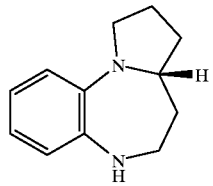

The same procedures used in Reference Example 62 were repeated using (3aR)-2,3,3a,4,5,6-hexahydro-1H-pyrrolo[1,2-a][1,5]benzodiazepin-5-one prepared in Reference Example 61 to give the title compound. Yield 88.5%.

$^1$H-N.M.R. (CDCl$_3$) δ: 1.62–1.76 (2 H, m), 1.85–2.04 (4 H, m), 2.76–2.87 (1 H, m), 3.17–3.33 (3 H, m), 3.41–3.52 (1 H, m), 6.60–6.88 (4 H, m); I.R. (neat) vcm$^{-1}$: 2940, 1590, 1490, 1315, 1150.

REFERENCE EXAMPLE 64

(2R,3aS)-2-(tert-Butyldimethyisilyloxy)-2,3,3a,4,5,6-Hexahydro-1H-Pyrrolo[1,2-a][1.5]Benzodiazepine

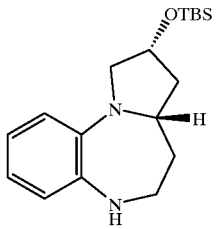

To a solution of (2S, 4R)-2-[4-(tert-butyldimethylsilyloxy)-1-(2-nitrophenyl) pyrrolidin-2-yl] acetonitrile (3.6 g) prepared in Reference Example 53 in dichloromethane (40 ml), there was dropwise added 10 ml of a 1M solution of diisobutyl aluminum hydride in dichloromethane over 30 minutes at −70° C. in a nitrogen gas atmosphere and the reaction solution was stirred at −70° C. for one hour. Methanol (10 ml) was added to the reaction solution at −70° C., then 40 ml of a 10% aqueous solution of citric acid was added thereto and the mixture was stirred at room temperature for one hour. The organic phase was separated, followed by washing with water, dehydration over anhydrous magnesium sulfate and concentration under reduced pressure. The resulting oily substance was dissolved in 200 ml of methanol, then 1.8 g of a 10% palladium-carbon catalyst was added to the solution and the mixture was stirred at room temperature for 15 hours in a hydrogen gas atmosphere. The catalyst present in the reaction solution was removed through filtration and the resulting filtrate was concentrated under reduced pressure. The resulting residue was subjected to silica gel column chromatography and eluted with ethyl acetate/hexane (1/3). The eluate was concentrated to give 1.35 g (yield 42.0%) of the title compound.

$^1$H-N.M.R. (CDCl$_3$) δ: 0.07 (3 H, s), 0.08 (3 H, s), 0.89 (91 H, s), 1.67–1.76 (1 H, m), 1.85–2.10 (2 H, m), 2.25–2.37 (1 H, m), 2.88–2.97 (1 H, m), 3.20 (1 H, d, J=10.0 Hz), 3.32 (1 H, dd, J=10.0, 4.0 Hz), 3.55–3.75 (2 H, m), 4.45(1 H, brs), 6.52–6.80 (4 H, m); I.R. (neat) vcm$^{-1}$: 3370, 1740, 1600, 1510, 1320, 1260.

EXAMPLE 1

(3aS)-5-[4-[(2-Phenylbenzoyl)Amino]Benzoyl]-1,2,3,3a,4,5-Hexahydro-Pyrrolo[1,2-a]Quinoxaline

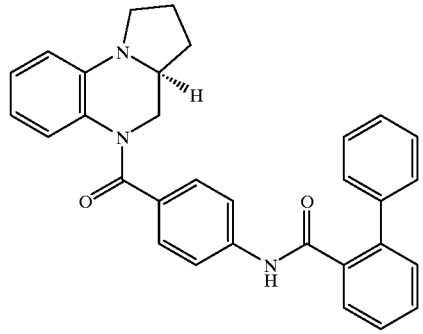

4-[(2-Phenylbenzoyl)amino]benzoic acid (0.47 g) was added to 1 ml of thionyl chloride and the mixture was heated under reflux for one hour. After cooling the reaction solution, the excess of the thionyl chloride was removed through concentration. The resulting acid chloride was dissolved in 10 ml of dichloromethane and the resulting solution was gradually dropwise added to a solution of (3aS)-1,2,3,3a,4,5-hexahydro-pyrrolo[1,2-a]quinoxaline (0.22 g) prepared in Reference Example 14 and triethylamine (0.19 g) in dichloromethane (15 ml) under ice-cooling. After stirring the reaction solution at room temperature for 3 hours, it was washed with, in order, water, a 1N aqueous solution of sodium carbonate, 1N hydrochloric acid and water and then dried over anhydrous magnesium sulfate. After concentration of the reaction solution, the resulting residue was subjected to silica gel column chromatography and then eluted with chloroform/ethyl acetate (99/1). The eluate was concentrated and the resulting residue was recrystallized from ethyl acetate-hexane to give 0.5 g (yield 85.8%) of the title compound.

m.p.: 199.5–200.5° C.; $^1$H-N.M.R. (CDCl$_3$) δ: 1.39–1.60 (1 H, m), 1.96–2.26 (3 H, m), 2.42–2.55 (1 H, m), 3.11–3.23 (1 H, m), 3.55–3.78 (2 H, m), 4.95–5.08 (1 H, m), 6.28–6.37 (1 H, m), 6.49 (1 H, brs), 6.54 (1 H, d, J=7.0 Hz), 6.90–7.02 (2 H, m), 7.04 (2 H, d, J=8.4 Hz), 7.31 (2 H, d, J=8.4 Hz), 7.35–7.59 (8 H, m), 7.89 (1 H, d, J=7.3 Hz); I.R. (KBr) vcm$^{-1}$: 3340, 1670, 1635, 1600, 1520, 1505, 1405, 1320.

EXAMPLE 2

(3aS)-5-[4-[[2-(4-Tolyl)Benzoyl Amino]Benzoyl]-1,2,3,3a,4,5-Hexahydro-Pyrrolo[1,2-a]Quinoxaline

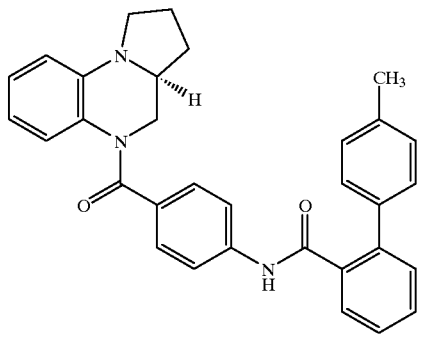

The same procedures used in Example 1 were repeated using (3aS)-1,2,3,3a,4,5-hexahydro-pyrrolo[1,2-a]quinoxaline prepared in Reference Example 14 and 4-[[2-(4-tolyl)benzoyl]amino]benzoic acid to give the title compound after recrystallization from ethyl acetate-hexane. Yield 46.7%.

m.p.: 228–229.5° C.; $^1$H-N.M.R. (CDCl$_3$) δ: 1.40–1.58 (1 H, m), 1.95–2.24 (3 H, m), 2.36 (3 H, s), 2.42–2.54 (1 H, m), 3.11–3.23 (1 H, m), 3.59 (1 H, t, J=8.1 Hz), 3.65–3.78 (1 H, m), 4.95–5.07 (1 H, m), 6.33 (1 H, t, J=7.7 Hz), 6.46–6.60 (2 H, m), 6.93–7.01 (2 H, m), 7.04 (2 H, d, J=7.7 Hz), 7.21 (2 H, d, J=7.7 Hz), 7.29–7.36 (2 H, m), 7.37–7.42 (2 H, m), 7.46 (1 H, td, J=7.3, 1.5 Hz), 7.53 (1 H, td, J=7.3, 1.5 Hz), 7.88 (11 H, d, J=7.3 Hz); I.R. (KBr) vcm$^{-1}$: 3330, 1675, 1620, 1515, 1500, 1405, 1315, 1250.

EXAMPLE 3

(2R,3aS)-2-Hydroxy-5-[4–1(2-Phenylbenzoyl)Amino]Benzoyl]-1,2,3,3a,4,5-Hexahydro-Pyrrolo[1,2-a]Quinoxaline

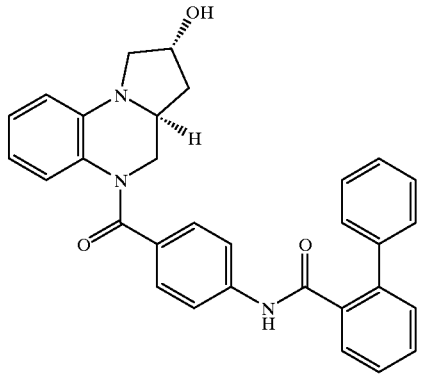

The same procedures used in Example 1 were repeated using (2R, 3aS)-2-hydroxy-1,2,3,3a,4,5-hexahydro-pyrrolo[1,2-a]quinoxaline prepared in Reference Example 16 and 4-[(2-phenylbenzoyl)amino]benzoic acid to give the title compound after recrystallization from ethyl acetate-hexane. m.p.: 243–244° C.; Yield 42.4%.

$^1$H-N.M.R. (CDCl$_3$) δ: 1.58–1.70 (1 H, m), 1.85–1.95 (1 H, m), 2.15–2.25 (1 H, m), 2.42–2.54 (1 H, m), 3.40–3.58 (2 H, m), 3.97–4.10(1 H, m), 4.65–4.71 (1 H, m), 4.96–5.06 (1 H, m), 6.31–6.39 (1 H, m), 6.51 (1 H, d, J=7.0 Hz), 6.92–7.07 (4 H, m), 7.32 (2 H, d, J=8.4 Hz), 7.35–7.59 (9 H, m), 7.84–7.92 (1 H, m); I.R. (KBr) vcm$^{-1}$: 3400, 2920, 1630, 1600, 1510, 1410, 1320, 1280, 1260, 1160, 1120.

EXAMPLE 4

(2R,3aS)-2-Hydroxy-5-[4-[[2-(4-Tolyl)Benzoyl]Amino]Benzoyl]-1,2,3,3a,4,5-Hexahydro-Pyrrolo[1,2-a]Quinoxaline

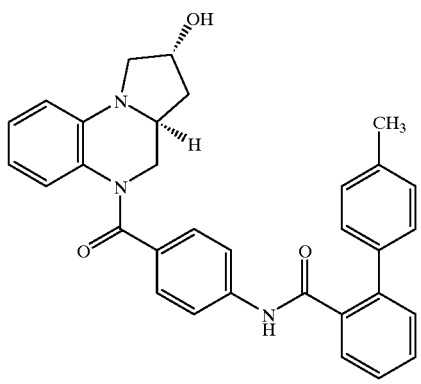

The same procedures used in Example 1 were repeated using (2R, 3aS)-2-hydroxy-1,2,3,3a,4,5-hexahydro-pyrrolo[1,2-a]quinoxaline prepared in Reference Example 16 and 4-[[2-(4-tolyl)benzoyl]amino]benzoic acid to give the title compound after recrystallization from ethyl acetate-hexane. m.p.: 163–164.5° C.; Yield 55.0%.

$^1$H-N.M.R. (CDCl$_3$) δ: 1.60–1.72 (1 H, m), 1.85–1.91 (1 H, m), 2.21 (1 H, dd, J=12.8, 5.1 Hz), 2.36 (3 H, s), 2.43–2.53 (1 H, m), 3.45 (1 H, dd, J=11.0, 4.0 Hz), 3.56 (1 H, d, J=11.0 Hz), 3.98–4.16 (1 H, m), 4.65–4.72 (1 H, m), 4.98–5.10 (1 H, m), 6.35 (1 H, t, J=7.3 Hz), 6.46–6.54 (2 H, m), 6.91–7.00 (2 H, m), 7.05 (2 H, d, J=8.8 Hz), 7.22 (2 H, d, J=8.1 Hz), 7.29–7.37 (4 H, m), 7.38–7.57 (3 H, m), 7.85–7.90 (1 H, m); I.R. (KBr) vcm$^{-1}$: 3390, 2910, 1620, 1600, 1520, 1405, 1320, 1270, 1250, 1180.

EXAMPLE 5

(2S, 3aS)-2-Acetoxy-5-[4-[(2-Phenylbenzoyl)Amino]Benzoyl]-1,2,3,3a,4,5-Hexahydro-Pyrrolo[1,2-a]Quinoxaline

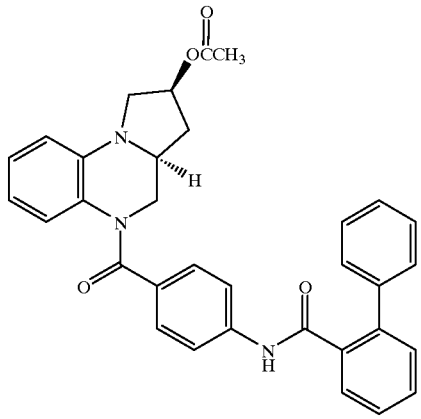

To a solution of (2R,3aS)-2-hydroxy-5-[4-[(2-phenylbenzoyl)amino]benzoyl]-1,2,3,3a,4,5-hexahydro-pyrrolo[1,2-a]quinoxaline (0.8 g) prepared in Example 3, acetic acid (0.15 g) and triphenyl phosphine (0.64 g) in anhydrous tetrahydrofuran (5 ml), there was gradually dropwise added a solution of diisopropyl azodicarboxylate (0.49 g) in anhydrous tetrahydrofuran (2 ml) under ice-cooling. After stirring the reaction solution at room temperature for 2 hours, it was concentrated. The resulting residue was subjected to silica gel column chromatography and then eluted with hexane/ethyl acetate (1/1) to give 0.66 g (yield 76.0%) of the title compound as amorphous powder.

$^1$H-N.N.R. (CDCl$_3$) δ: 1.70–1.85 (1 H, m), 2.06 (3 H, s), 2.50–2.80 (2 H, m), 3.27–3.35 (1 H, m), 3.65–3.93 (2 H, m), 4.85–4.95 (1 H, m), 5.35–5.50 (1 H, m), 6.38 (1 H, t, J=7.6 Hz), 6.52 (1 H, d, J=7.6 Hz), 6.90–7.10 (4 H, m), 7.28–7.58 (11 H, m), 7.90 (1 H, d, J=7.6 Hz); I.R. (KBr) vcm$^{-1}$: 1740, 1640, 1600, 1510, 1240.

EXAMPLE 6

(2S, 3aS)-2-Acetoxy-5-[4-[[2-(4-Tolyl)Benzoyl]Amino]Benzoyl]-1,2,3,3a,4,5-Hexahydro-Pyrrolo[1,2-a]Quinoxaline

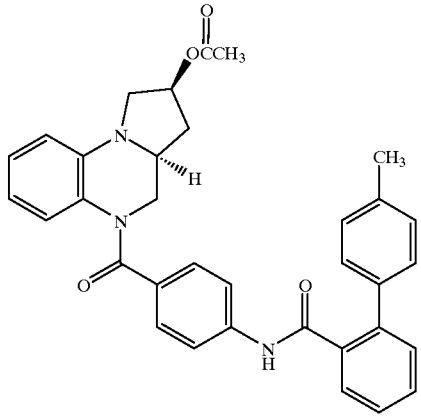

The same procedures used in Example 5 were repeated using (2R, 3aS)-2-hydroxy-5-[4-[[2-(4-tolyl)benzoyl]

amino]benzoyl]-1,2,3,3a,4,5-hexahydro-pyrrolo[1,2-a] quinoxaline prepared in Example 4 to thus give the title compound as amorphous powder. Yield 63.2%.

$^1$H-HN.M.R. (CDCl$_3$) δ: 158–1.71 (1 H 1.95 (1 H, d, J=5.13 Hz), 2.36 (3 H, s), 2.44 (3 H, s), 2.67 (1 H, t, J=10.7 Hz), 3.12–3.19 (1 H, m), 3.17–3.82 (2 H, m), 4.64–4.78 (1 H, m), 4.83–4.97 (1 H, m), 6.36 (1 H, t, J=8.1 Hz), 6.47–6.58 (2 H, m), 6.91–7.08 (4 H, m), 7.21 (2 H) d, J=8.1 Hz), 7.27–7.34 (4 H, m), 7.36–7.56 (3 H, m), 7.81–7.88 (1 H, m); I.R. (K B r) vcm$^{-1}$: 3400, 1740, 1630, 1605, 1515, 1505, 1410, 1320.

EXAMPLE 7

(2S, 3aS)-2-Hydroxy-5-[4-[(2-Phenylbenzoyl) Amino]Benzoyl]-1,2,3,3a,4,5-Hexahydro-Pyrrolo[1, 2-a]Quinoxaline

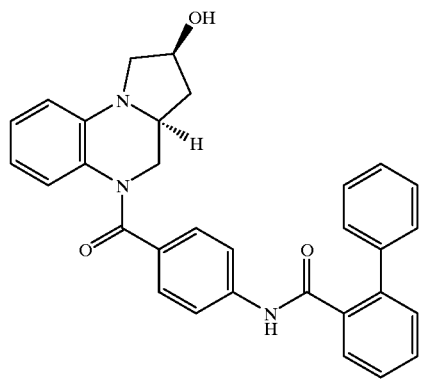

To 20 ml of methanol, there were added 0.57 g of (2S, 3aS)-2-acetoxy-5-[4-[(2-phenylbenzoyl)amino]benzoyl]-1,2,3,3a,4,5-hexahydro-pyrrolo [1,2-a]quinoxaline prepared in Example 5 and 0.2 g of anhydrous potassium carbonate and the reaction solution was stirred at room temperature for 15 hours. After concentration of the reaction solution, the resulting residue was diluted with water and then extracted with ethyl acetate. The resulting organic phase was washed with water, dried over anhydrous magnesium sulfate and then concentrated. The resulting residue was recrystallized from ethyl acetate-hexane to give 0.52 g (yield 88.0%) of the title compound.

m.p.: 164–165° C.; $^1$H-N.M.R. (CDCl$_3$) δ: 1.60–1.70 (1 H, m), 1.79 (1 H, d, J=7.3 Hz), 2.40–2.50 (1 H, m), 2.63–2.75 (1 H, m), 3.15–3.23 (1 H, m), 3.65–3.85 (2 H, m), 4.65–4.95 (2 H, m), 6.36 (1 H, t, J=7.1 Hz), 6.52 (1 H, d, J=7.1 Hz), 6.90–7.10 (4 H, m), 7.30–7.60 (10 H, m), 7.90 (1 H, t, J=7.1 Hz); I.R. (KBr) vcm$^{-1}$: 1630, 1600, 1500, 1400, 1320.

EXAMPLE 8

(2S, 3aS)-2-Hydroxy-5-[4-[[2-(4-Tolyl) Benzoyl] Amino]Benzoyl]-1,2,3,3a,4,5-Hexahydro-Pyrrolo[1, 2-a]Quinoxahine

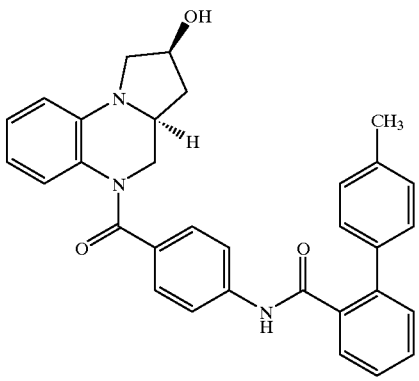

The same procedures used in Example 7 were repeated using (2S, 3aS)-2-acetoxy-5-[4-[[2-(4-tolyl)benzoyl]amino] benzoyl]-1,2,3,3a,4,5-hexahydro-pyrrolo[1,2-a]quinoxaline prepared in Example 6 to give the title compound after recrystallization from ethyl acetate-hexane. Yield, 63.2%.

m.p. 163–164° C.; $^1$H-N.M.R. (CDCl$_3$) δ: 1.58–1.73 (1 H, m) 1.95 (1 H, d , J=5.1 Hz), 2.36 (3 H, s ), 2.44 (1 H, quint., J=6.2 Hz), 2.67 (1 H, t, J=10.7 Hz), 3.12–3.19 (1 H, m), 3.17–3.82 (2 H, m), 4.64–4.78 (1 H, m), 4.83–4.97 (1 H, m), 6.36 (1 H, t, J=8.1 Hz) 6.47–6.58 (2 H, m), 6.91–7.08 (4 H, m), 7.21 (2 H, d, J=8.1 Hz), 7.27–7.34 (4 H, m), 7.36–7.56 (3 H, m), 7.81–7.88 (1 H, m); I.R. (KBr) vcm$^{-1}$: 3400, 1630, 1605, 1515, 1505, 1410, 1320.

REFERENCE EXAMPLE 65

(2S, 3aS)-5-[4-[(2-Phenylbenzoyl) Amino]Benzoyl]-2-Phthalimido-1,2,3,3a,4,5-Hexahydro-Pyrrolo[1,2-a]Quinoxaline

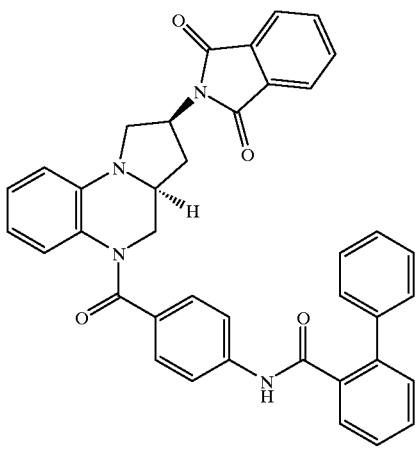

To a solution of (2R,3aS)-2-hydroxy-5-[4-[(2-phenylbenzoyl)amino]benzoyl]-1,2,3,3a,4,5-hexahydro-pyrrolo[1,2-a]quinoxaline (1.2 g) prepared in Example 3, phthalimide (0.54 g) and triphenyl phosphine (0.96 g) in anhydrous N,N-dimethylformamide (10 ml), there was gradually dropwise added, under ice-cooling, a solution of diisopropyl azodicarboxylate (0.74 g) in anhydrous N,N-dimethylformamide (4 ml). After stirring the reaction solution at room temperature for 2 hours, it was poured into ice water and then extracted with ethyl acetate. The resulting organic phase was washed with water, dried over anhydrous magnesium sulfate and then concentrated. The resulting residue was subjected to silica gel column chromatography and then eluted with hexane/ethyl acetate (1/1) to give 1.1 g (yield 73.0%) of the title compound as amorphous powder.

$^1$H-N.M.R. (CDCl$_3$) δ: 2.25–2.35 (1 H, m), 2.55–2.80 (2 H, m), 3.70–4.00 (3 H, m), 4.95–5.30 (2 H, m), 6.48 (1 H, t, J=7.6 Hz), 6.51 (1 H, d, J=7.6 Hz), 6.55 (1 H, brs), 6.90–7.10 (4 H, m), 7.30–7.90 (15 H, m); I.R. (KBr) vcm$^{-1}$: 1780, 1705, 1640, 1600, 1380.

EXAMPLE 9

(2S, 3aS)-2-Amino-5-[4-[(2-Phenylbenzoyl) Amino] Benzoyl]-1,2,3,3a,4,5-Hexahydro-Pyrrolo[1,2-a] Quinoxaline

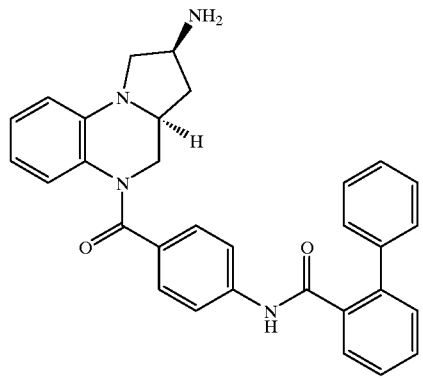

Hydrazine monohydrate (0.41 g) was added to a solution of (2S, 3aS)-5-[4-[(2-phenylbenzoyl)amino]benzoyl]-2-phthalimido-1,2,3,3a,4,5-hexahydro-pyrrolo[1,2-a]quinoxaline (1.0 g) prepared in Reference Example 65 in ethanol (10 ml) and the mixture was heated under reflux conditions for one and half hours. After cooling the reaction solution, the ethanol was removed through concentration. The resulting residue was dissolved in chloroform, the resulting solution was washed with a 5% aqueous solution of sodium hydroxide and water, died over anhydrous magnesium sulfate and then concentrated. The resulting residue was subjected to silica gel column chromatography and then eluted with chloroform/methanol (95/5) to give 0.68 g (yield 86.0%) of the title compound as amorphous powder.

$^1$H-N.M.R. (CDCl$_3$) δ: 1.30–1.45 (1 H, m), 2.30–2.40 (1 H, m), 2.45–2.60 (1 H, m), 2.80–2.90 (1 H, m), 3.70–3.90 (3 H, m), 4.90–5.00 (1 H, m), 6.33 (1 H, t, J=7.8 Hz), 6.49 (1 H, d, J=7.1 Hz), 6.49 (1 H, brs), 6.90–7.10 (4 H, m), 7.30–7.60 (10 H, m), 7.88 (1 H, d, J=7.1 Hz); I.R. (KBr) vcm$^{-1}$: 3400, 1600, 1500, 1400.

EXAMPLE 10

(2S, 3aS)-2-(N,N-Dimethylamino)-5-[4-[(2-Phenylbenzoyl) Amino]Benzoyl]-1,2,3,3a,4,5-Hexahydro-Pyrrolo[1,2-a]Quinoxaline Hydrochloride

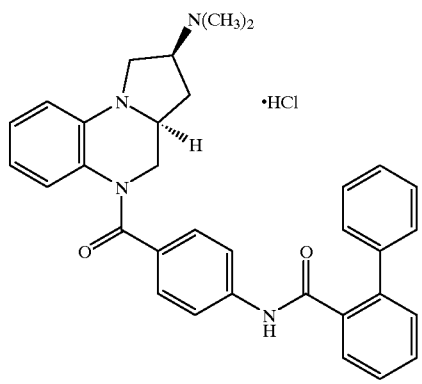

A 37% aqueous formaldehyde solution (0.75 ml) was added to a solution of (2S, 3aS)-2-amino-5-[4-[(2-phenylbenzoyl)amino]benzoyl]-1,2,3,3a,4,5-hexahydro-pyrrolo[1,2-a]quinoxaline (0.9 g) prepared in Example 9 in methanol (10 ml) and the resulting mixture was stirred at room temperature for 15 minutes. Then 0.2 g of sodium cyanoborohydride was added thereto over one hour and the mixture was stirred at room temperature for 15 hours. After concentration of the reaction solution, the resulting residue was dissolved in chloroform, the resulting solution was washed with water and dried over anhydrous magnesium sulfate. After concentration of the solution, the resulting residue was subjected to silica gel column chromatography and then eluted with chloroform/methanol (19/1). The resulting eluate was dissolved in 30 ml of ethyl acetate, followed by addition of 0.4 ml of a 4N hydrochloric acid-ethyl acetate solution thereto, recovery of the resulting precipitates through filtration and washing thereof with a small amount of ethyl acetate to thus give 0.73 g (yield 72.7%) of the title compound.

m.p.: 211–213° C.; $^1$H-N.M.R. (DMSO-d$_6$) δ: 1.82–1.98 (1 H, m), 2.58–2.70 (1 H, m), 2.78–2.93 (6 H, m), 3.22–3.48 (2 H, m), 3.63–3.92 (2 H, m), 4.02–4.18 (1 H, m), 4.65–4.78 (1 H, m), 6.42 (1 H, t, J=7.3 Hz), 6.66 (2 H, d, J=7.0 Hz), 6.93–7.02 (1 H, m), 7.25–7.62 (13 H, m), 10.42 (1 H, s), 11.26 (1 H, brs); I.R. (KBr) vcm$^{-1}$: 3400, 1625, 1600, 1515, 1505, 1410, 1320.

EXAMPLE 11

(3aR)-5-[4-[(2-Phenylbenzoyl) Amino]Benzoyl]-1,2,3,3a,4,5-Hexahydro-Pyrrolo[1,2-a]Quinoxaline

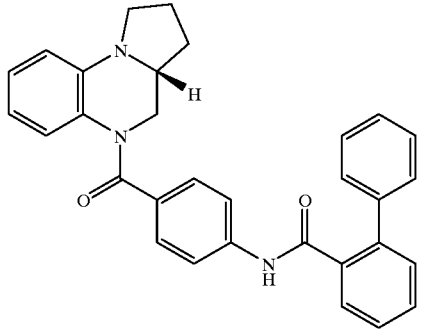

The same procedures used in Example 1 were repeated using (3aR)-1,2,3,3a,4,5-hexahydro-pyrrolo[1,2-a]quinoxaline prepared in Reference Example 15 and 4-[(2-phenylbenzoyl)amino]benzoic acid to give the title compound after recrystallization from dioxane-hexane. Yield 57.8%.

m.p.: 199.5–200.5° C.; $^1$H-N.M.R. (CDCl$_3$) δ: 1.39–1.60 (1 H, m), 1.96–2.26 (3 H, m), 2.42–2.55 (1 H, m), 3.11–3.23 (1 H, m), 3.55–3.78 (2 H, m), 4.95–5.08 (1 H, m), 6.28–6.37 (1 H, m), 6.49 (1 H, brs), 6.54 (1 H, d, J=7.0 Hz), 6.90–7.02 (2 H, m), 7.04 (2 H, d, J=8.4 Hz), 7.31 (2 H, d, J=8.4 Hz), 7.35–7.59 (8 H, m), 7.89 (1 H, d, J=7.3 Hz); I.R. (KBr) vcm$^{-1}$: 3340, 1670, 1635, 1600, 1520, 1505, 1405, 1320.

EXAMPLE 12

(3aR)-5-[4-[[2-(4-Tolyl) Benzoyl]Amino]Benzoyl]-1,2,3,3a,4,5-Hexahydro-Pyrrolo[1,2-a]Quinoxaline

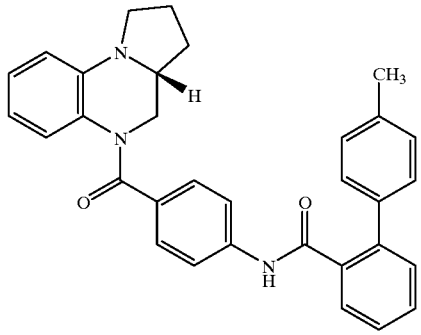

The same procedures used in Example 1 were repeated using (3aR)-1,2,3,3a,4,5-hexahydro-pyrrolo[1,2-a]quinoxaline prepared in Reference Example 15 and 4-[[2-(4-tolyl)benzoyl]amino]benzoic acid to give the title compound after recrystallization from ethyl acetate-hexane. Yield 31.7%.

m.p.: 228–229.50° C.; $^1$H-N.M.R. (CDCl$_3$) δ: 1.40–1.58 (1 H, m), 1.95–2.24 (3 H, m), 2.36 (3 H, s), 2.42–2.54 (1 H, m), 3.11–3.23 (1 H, m), 3.59 (1 H, t, J=8.1 Hz), 3.65–3.78 (1 H, m), 4.95–5.07 (1 H, m), 6.33 (1 H, t, J=7.7 Hz), 6.46–6.60 (2 H, m), 6.93–7.01 (2 H, m), 7.04 (2 H, d, J=7.7 Hz), 7.21 (2 H, d, J=7.7 Hz), 7.29–7.36 (2 H, m), 7.37–7.42 (2 H, m), 7.46 (1 H, td, J=7.3, 1.5 Hz), 7.53 (1 H, td, J=7.3, 1.5 Hz), 7.88 (1 H, d, J=7.3 Hz); I.R. (KBr) vcm$^{-1}$: 3330, 1675, 1620, 1515, 1500, 1405, 1315, 1250.

EXAMPLE 13

(2R,3aR)-2-Hydroxy-5-[4-[(2-Phenylbenzoyl) Amino]Benzoyl]-1,2,3,3a,4,5-Hexahydro-Pyrrolo[1,2-a]Quinoxaline

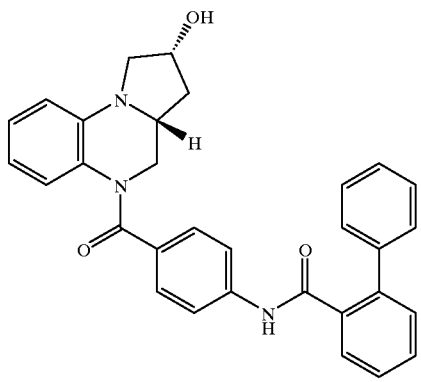

The same procedures used in Example 1 were repeated using (2R, 3aR)-2-hydroxy-1,2,3,3a,4,5-hexahydro-pyrrolo[1,2-a]quinoxaline prepared in Reference Example 17 and 4-[(2-phenylbenzoyl)amino]benzoic acid to give the title compound after recrystallization from ethyl acetate-hexane. Yield 53.1%.

m.p.: 164–165° C.; $^1$H-N.M.R. (CDCl$_3$) δ: 1.60–1.70 (1 H, m), 1.79 (1 H, d, J=7.3 Hz), 2.40–2.50 (1 H, m), 2.63–2.75 (1 H, m), 3.15–3.23 (1 H, m), 3.65– 3.85 (2 H, m), 4.65–4.95 (2 H, m), 6.36 (1 H, t, J=7.1 Hz), 6.52 (1 H, d, J=7.1 Hz), 6.90–7.10 (4 H, m), 7.30–7.60 (10 H, m), 7.90 (1 H, t, J=7.1 Hz); I.R. (KBr) vcm$^{-1}$: 1630, 1600, 1500, 1400, 1320.

EXAMPLE 14

(2R,3aR)-2-Hydroxy-5-[4-[[2-(4-Tolyl) Benzoyl] Amino]Benzoyl]-1,2,3,3a-4,5-Hexahydro-Pyrrolo[1,2-a]Quinoxaline

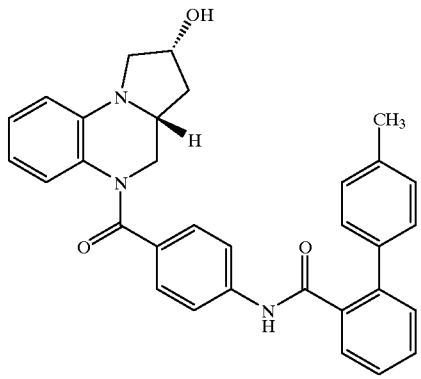

The same procedures used in Example 1 were repeated using (2R, 3aR)-2-hydroxy-1,2,3,3a,4,5-hexahydro-pyrrolo[1,2-a]quinoxaline prepared in Reference Example 17 and 4-[[2-(4-tolyl)benzoyl)amino]benzoic acid to give the title compound after recrystallization from ethyl acetate-hexane. Yield 53.5%.

m.p.: 163–164° C.; ¹H-N.M.R. (CDCl₃) δ: 1.58–1.73 (1 H, m), 1.95 (1 H, d, J=5.1 Hz), 2.36 (3 H, s), 2.44 (1 H, quint., J=6.2 Hz), 2.67 (1 H, t, J=10.7 Hz), 3.12–3.19 (1 H, m), 3.17–3.82 (2 H, m), 4.64–4.78 (1 H, m), 4.83–4.97 (1 H, m), 6.36 (1 H, t, J=8.1 Hz), 6.47–6.58 (2 H, m), 6.91–7.08 (4 H, m), 7.21 (2 H, d, J=8.1 Hz), 7.27–7.34 ( 4 H, m), 7.36–7.56 (3 H, m), 7.81–7.88 (1 H, m); I.R. (KBr) vcm⁻¹: 3400, 1630, 1605, 1515, 1505, 1410, 1320.

EXAMPLE 15

(2S, 3aR)-2-Acetoxy-5-[4-[(2-Phenylbenzoyl)Amino]Benzoyl]-1,2,3,3a,4,5-Hexahydro-Pyrrolo]1,2-a]Quinoxaline

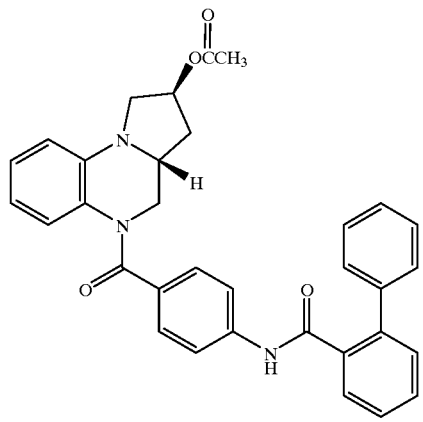

The same procedures used in Example 5 were repeated using (2R, 3aR)-2-hydroxy-5-[4-[(2-phenylbenzoyl)amino]benzoyl]-1,2,3,3a,4,5-hexahydro-pyrrolo[1,2-a]quinoxaline prepared in Example 13 to give the title compound as amorphous powder. Yield 66.3%.

¹H-N.M.R. (CDCl₃) δ: 1.67–1.79 (1 H, m), 2,11 (3 H, s), 2.27–2.35 (1 H, m), 2.45–2.57 (1 H, m), 3.51–3.65 (2 H, m), 3.91–4.07 (1 H, m), 4.49–5.12 (1 H, m), 5.48–5.54 (1 H, m), 6.33–6.40 (1 H, m), 6.45–6.56 (2 H, m), 6.88–7.07 (4 H, m), 7.32 (2 H, d, J=8.8 Hz), 7.36–7.59 (7 H, m), 7.88–7.93 (1 H, m); I.R. (KBr) vcm⁻¹: 3290, 1740, 1650, 1600, 1505, 1410, 1320, 1250.

EXAMPLE 16

(2S, 3aR)-2-Acetoxy-5-[4-[[2-(4-Tolyl) Benzoyl]Amino]Benzoyl]-1,2,3,3a,4,5-Hexahydro-Pyrrolo[1,2-a]Quinoxaline

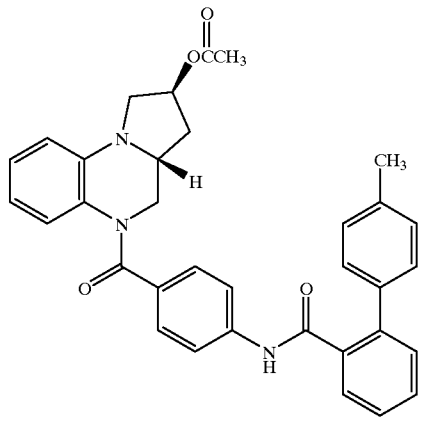

The same procedures used in Example 5 were repeated using (2R 3aR)-2-hydroxy-5-[4-[[2-(4-tolyl)benzoyl]amino]benzoyl]-1,2,3,3a,4,5-hexahydro-pyrrolo[1,2-a]quinoxaline prepared in Example 14 to give the title compound as amorphous powder. Yield 96.3%.

¹H-N.M.R. (CDCl₃) δ: 1.67–1.80 (1 H, m), 2.11 (3 H, s), 2.31 (1 H, dd, J=5.1, 2.5 Hz), 2.36 (3 H, s), 2.43–2.55 (1 H, m), 3.50–3.65 (2 H, m), 3.91–4.06 (1 H, m), 4.99–5.12 (1 H, m), 5.48–6.04 (1 H, m), 6.37 (1 H, t, J=7.3 Hz), 6.48–6.55 (2 H, m), 6.94–7.09 (4 H, m), 7.21 (2 H, d, J=7.7 Hz), 7.28–7.58 (5 H, m), 7.61–7.71 (2 H, m), 7.87 (1 H, d, J=7.7 Hz); I.R. (KBr) vcm⁻¹: 3270, 1740, 1640, 1600, 1510, 1400, 1320, 1245.

EXAMPLE 17

(2S, 3aR)-2-Hydroxy-5-[4-[(2-Phenylbenzoyl)Amino]Benzoyl]-1,2,3,3a,4,5-Hexahydro-Pyrrolo[1,2-a]Quinoxaline

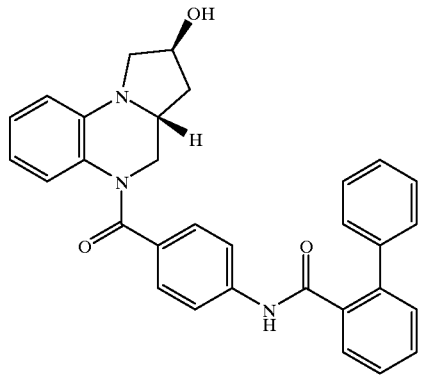

The same procedures used in Example 7 were repeated using (2S, 3aR)-2-acetoxy-5-[4-[(2-phenylbenzoyl)amino]benzoyl]-1,2,3,3a,4,5-hexahydro-pyrrolo[1,2-a]quinoxaline prepared in Example 15 to give the title compound after recrystallization from ethyl acetate-hexane. Yield 85.6%.

m.p: 243–244° C. ¹H-N.M.R. (CDCl₃) δ: 1.58–1.70 (1 H, m), 1.85–1.95 (1 H, m), 2.15–2.25 (1 H, m), 2.42–2.54 (1 H, m), 3.40–3.58 (2 H, m), 3.97–4.10 (1 H, m), 4.65–4.71 (1 H, m), 4.96–5.06 (1 H, m), 6.31–6.39 (1 H, m), 6.51 (1 H, d, J=7.0 Hz), 6.92–7.07 (4 H, m), 7.32 (2 H, d, J=8.4 Hz), 7.35–7.59 (9 H, m), 7.84–7.92 (1 H, m); I.R. (KBr) vcm⁻¹: 3400, 2920, 1630, 1600, 1510, 1410, 1320, 1280, 1260, 1160, 1120.

EXAMPLE 18

(2S, 3aR)-2-Hydroxy-5-[4-[[2-(4-Tolyl) Benzoyl] Amino]Benzoyl]-1,2,3,3a,4,5-Hexahydro-Pyrrolo[1,2-a]Quinoxaline

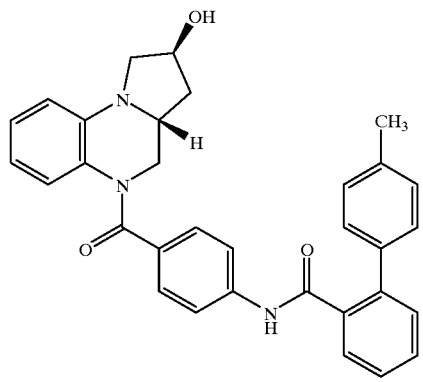

The same procedures used in Example 7 were repeated using (2S, 3aR)-2-acetoxy-5-[4-[[2-(4-tolyl)benzoyl]amino]benzoyl]-1,2,3,3a,4,5-hexahydro-pyrrolo[1,2-a]quinoxaline prepared in Example 16 to give the title compound after recrystallization from ethyl acetate-hexane. Yield 88.6%.

m.p.: 163–164.5° C.; ¹H-N.M.R. (CDCl₃) δ: 1.60–1.72 (1 H, m), 1.85–1.91 (1 H, m), 2.21 (1 H, dd, J=12.8, 5.1 Hz), 2.36 (3 H, s), 2.43–2.53 (1 H, m), 3.45 (1 H, dd, J=11.0, 4.0 Hz), 3.56 (1 H, d, J=11.0 Hz), 3.98–4.16 (1 H, m), 4.65–4.72 (1 H, m), 4.98–5.10 (1 H, m), 6.35 (1 H, t, J=7.3 Hz), 6.46–6.54 (2 H, m), 6.91–7.00 (2 H, m), 7.05 (2 H, d, J=8.8 Hz), 7.22 (2 H, d, J=8.1 Hz), 7.29–7.37 (4 H, m), 7.38–7.57 (3 H, m), 7.85–7.90 (1 H, m); I.R. (KBr) vcm⁻¹: 3390, 2910, 1620, 1600, 1520, 1405, 1320, 1270, 1250, 1180.

REFERENCE EXAMPLE 66

(2S, 3aR)-5-[4-[(2-Phenylbenzoyl) Amino] Benzoyl]-2-Phthahimido-1,2,3,3a,4,5-Hexahydro-Pyrrolo[1,2-a]Quinoxaline

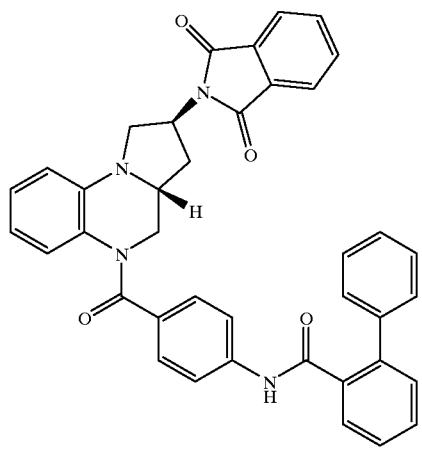

The same procedures used in Reference Example 65 were repeated using (2R,3aR)-2-hydroxy-5-[4-[(2-phenylbenzoyl)amino]benzoyl]-1,2,3,3a,4,5-hexahydro-pyrrolo[1,2-a]quinoxaline obtained in Example 13 to give the title compound as amorphous powder. Yield 75.9%.

¹H-N.M.R. (CDCl₃) δ: 2.00–2.13 (1 H, m), 2.14–2.54 (1 H, m), 2.63–2.78 (1 H, m), 3.68–3.74 (1 H, m), 3.84–3.95 (1 H m), 4.18–4.30 (1 H, m), 4.86–5.00 (1 H, m), 5.03–5.16 (1 H, m), 6.30–6.41 (1 H, m), 6.51 (1 H, d, J=7.3 Hz), 6.55–6.69 (1 H, m), 6.90–7.10 (4 H, m), 7.30–7.59 (10 H, m), 7.70–7.79 (2 H, m), 7.82–7.93 (3 H, m); I.R. (KBr) vcm⁻¹: 3400, 1780, 1710, 1600, 1510, 1380, 1320, 1250, 1180, 1120.

REFERENCE EXAMPLE 67

(2S, 3aR)-2-Phthalimido-5-[4-[[2-(4-Tolyl) Benzoyl]Amino]Benzoy]-1,2,3,3a,4,5-Hexahydro-Pyrrolo[1,2-a]Quinoxaline

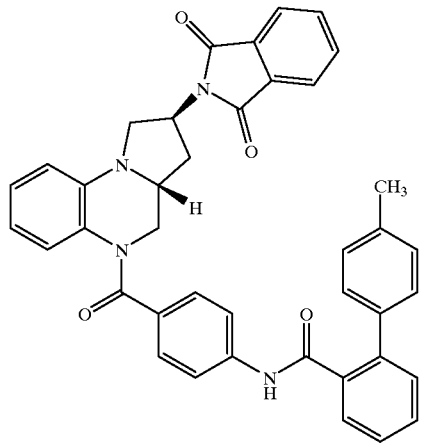

The same procedures used in Reference Example 65 were repeated, using (2R,3aR)-2-hydroxy-5-[4-[[2-(4-tolyl)benzoyl]amino]benzoyl]-1,2,3,3a,4,5-hexahydro-pyrrolo[1,2-a]quinoxaline obtained in Example 14 to give the title compound as amorphous powder. Yield 75.6%.

$^1$H-N.M.R. (CDCl$_3$) δ: 2.02–2.15 (1 H, m), 2.37 (3 H, s), 2.40–2.57 (1 H, m), 2.67–2.78 (1 H, m), 3.64–3.76 (1 H, m), 3.85–3.96 (1 H, m), 4.19–4.32 (1 H, m), 4.87–4.98 (1 H, m), 5.03–5.16 (1 H, m), 6.37 (1 H, t, J=8.1 Hz), 6.51 (1 H, d, J=8.1 Hz), 6.91–7.10 (2 H, m), 7.19–7.29 (2 H, m), 7.30–7.59 (7 H, m), 7.62–7.79 (6 H, m), 7.82–7.95 (3 H, m); I.R. (KBr) νcm$^{-1}$: 3400, 1780, 1710, 1600, 1520, 1380, 1320, 1180, 1120,

EXAMPLE 19

(2S, 3aR)-2-Amino-5-[4-[(2-Phenylbenzoyl)Amino]Benzoyl]-1,2,3,3a,4,5-Hexahydro-Pyrrolo[1,2-a]Quinoxaline

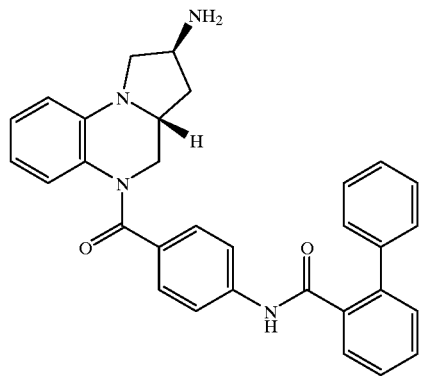

The same procedures used in Example 9 were repeated using (2S, 3aR)-5-[4-[(2-phenylbenzoyl)amino]benzoyl]-2-phthalimido-1,2,3,3a,4,5-hexahydro-pyrrolo[1,2-a]quinoxaline prepared in Reference Example 66 to thus give the title compound as amorphous powder. Yield 69.8%.

$^1$H-N.M.R. (CDCl$_3$) δ: 1.62–1.76 (1 H, m), 2.00 (1 H, d, J=5.1 Hz), 2.41–2.54 (1 H, m), 3.33–3.46 (2 H, m), 3.81–3.88 (1 H, m), 3.95–4.10 (1 H ), 4.92–5.07 (1 H, m), 6.34 (1 H, t, J=7.3 Hz), 6.45–6.59 (2 H, m), 6.90–7.08 (4 H, m), 7.33 (2 H, d, J=8.4 Hz), 7.35–7.58 (8 H, m), 7.85–7.94 (1 H, m); I.R. (KBr) νcm$^{-1}$: 3280, 1635, 1600, 1515, 1505, 1410, 1320.

EXAMPLE 20

(2S, 3aR)-2-Amino-5-[4-[[2-(4-Tolyl) Benzoyl]Amino]Benzoyl]-1,2,3,3a,4,5-Hexahydro-Pyrrolo[1,2-a]Quinoxaline

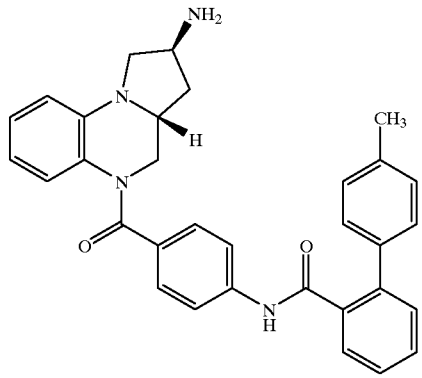

The same procedures used in Example 9 were repeated using (2S, 3aR)-2-phthalimido-5-[4-[[2-(4-tolyl)benzoyl]amino]benzoyl]-1,2,3,3a,4,5-hexahydro-pyrrolo[1,2-a]quinoxaline prepared in Reference Example 67 to thus give the title compound as amorphous powder. Yield 50.5%.

$^1$H-N.M.R. (CDCl$_3$) δ: 1.62–1.78 (1 H, m), 1.95–2.05 (1 H, m), 2.30–2.54 (4 H, m), 3.31–3.48 (2 H, m), 3.81–3.89 (1 H, m), 3.94–4.11 (1 H, m), 4.93–5.10 (1 H, m), 6.34 (1 H, t, J=7.3 Hz), 6.45–6.60 (2 H, m), 6.92–7.12 (4 H, m), 7.17–7.55 (9 H, m), 7.83–7.94 (1 H, m); I.R. (KBr) νcm$^{-1}$: 3290, 1630, 1600, 1515, 1505, 1410, 1320.

EXAMPLE 21

(2S, 3aR)-2-(N,N-Dimethylamino)-5-[4-[(2-Phenylbenzoyl) Amino]Benzoyl]-1,2,3,3a,4,5-Hexahydro-Pyrrolo[1,2-a]Quinoxaline

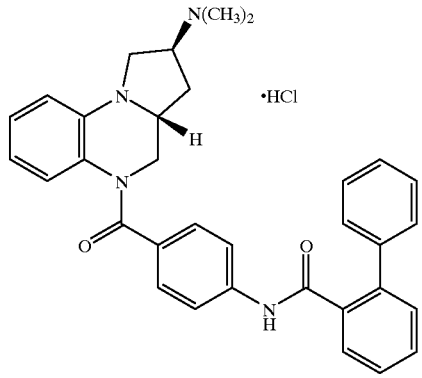

The same procedures used in Example 10 were repeated using (2S, 3aR)-2-amino-5-[4-[(2-phenylbenzoyl)amino]benzoyl]-1,2,3,3a,4,5-hexahydro-pyrrolo[1,2-a]quinoxaline prepared in Example 19 to thus give the title compound. Yield 63.0%.

m.p.: 195–197° C.; $^1$H-N.M.R. (DMSO-d$_6$) δ: 2.05–2.21 (1 H, m), 2.62–2.80 (2 H, m), 2.88 (3 H, s), 2.89 (3 H, s), 3.62–3.76 (1 H, m), 3.80–4.22 (3 H, m), 4.58–4.75 (1 H, m), 6.54 (1 H, t, J=7.7 Hz), 6.75–6.90 (2 H, m), 7.02–7.12 (1 H, m), 7.34–7.72 (13 H, m), 10.53 (1 H, s), 11.15 (11 H, brs); I.R. (KBr) νcm$^{-1}$: 3420, 1635, 1600, 1505, 1410, 1320.

EXAMPLE 22

(2S, 3aR)-2-(N,N-Dimethylamino)-5-[4-[[2-(4-Tolyl) Benzoy]Amino]Benzoyl]-1,2,3,3a,4,5-Hexahydro-Pyrrolo[1,2-a]Quinoxaline Hydrochloride

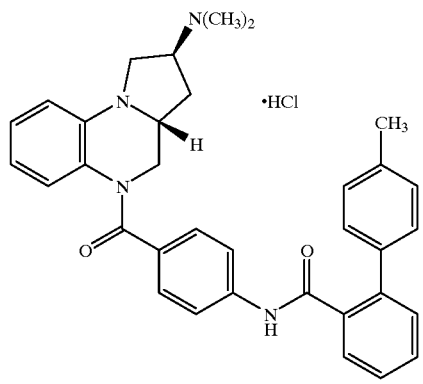

The same procedures used in Example 10 were repeated using (2S, 3aR)-2-amino-5-[4-[[2-(4-tolyl)benzoyl)amino]benzoyl]-1,2,3,3a,4,5-hexahydro-pyrrolo[1,2-a]quinoxaline prepared in Example 20 to thus give the title compound. Yield 85.5%. m.p.: 175° C. (decomposition);

$^1$H-N.M.R. (DMSO-$d_6$) δ: 2.07–2.23 (1 H, m), 2.60–2.80 (2 H, m), 2.90 (3 H, s), 2.93 (3 H, s), 3.55 (3 H, s), 3.63–3.76 (1 H, m), 3.80–4.25 (3 H, m), 4.57–4.79 (1 H, m), 6.56 (1 H, t, J=7.7 Hz), 6.77–6.92 (2 H, m), 7.04–7.12 (1 H, m), 7.33–7.70 (12 H, m), 10.55 (1 H, s ), 11.19 (1 H, brs); I.R. (KBr) vcm$^{-1}$: 3400, 1635, 1600, 1515, 1505, 1405, 1320.

EXAMPLE 23

(2S, 3aR)-2-Fluoro-5-[4-[(2-Phenylbenzoyl) Amino]Benzoyl]-1,2,3,3a,4,5-Hexahydro-Pyrrolo[1,2-a]Quinoxaline

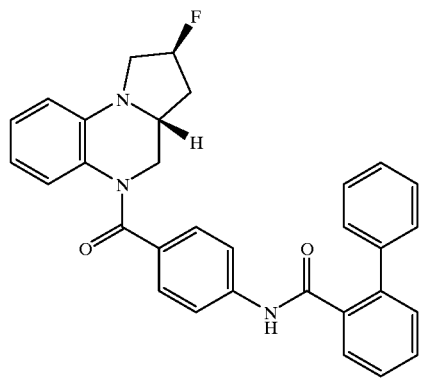

To a solution of (2R,3aR)-2-hydroxy-5-[4-[(2-phenaylbenzoyl)amino]benzoyl]-1,2,3,3a,4,5-hexahydro-pyrrolo[1,2-a]quinoxaline (0.5 g) prepared in Example 13 in anhydrous dichloromethane (25 ml), there was dropwise added, with ice-cooling, a solution of diethylaminosulfur trifluoride (0.23 g) in anhydrous dichloromethane (10 ml) over 10 minutes. The reaction solution was stirred for one hour under ice-cooling, it was washed, in order, with a saturated aqueous solution of sodium bicarbonate, water, a 1N hydrochloric acid solution and water and then dried over anhydrous magnesium sulfate. After concentration of the reaction solution, the resulting residue was subjected to silica gel column chromatography and, eluted with chloroform/ethyl acetate (99/1). The resulting eluate was concentrated and the resulting residue was recrystallized from ethyl acetate-hexane to thus give 0.27 g (yield 41.3%) of the title compound.

m.p.: 136–145° C.; $^1$H-N.M.R. (CDCl$_3$) δ: 1.52–1.82 (1 H, m), 2.41–2.58 (2 H, m), 3.41–3.63 (1 H, m), 3.70–389 (1 H, m), 3.95–4.16 (1 H, m), 5.01–5.14 (1 H, m), 5.30–5.55 (1 H, m), 6.40 (1 H, t, J=8.1 Hz), 6.48–6.56 (2 H, m), 6.90–7.08 (4 H, m), 7.29–7.59 (10 H, m), 7.90 (1 H, d, J=7.3 Hz); I.R. (KBr) vcm$^{-1}$: 3290, 1640, 1600, 1520, 1505, 1405, 1320, 1180.

EXAMPLE 24

(3aR)-4-[[2-(4-Tolyl) Benzoyl]Amino]Benzoyl]-1,2,3,3a,4,5-Hexahydro-Pyrrolo[1,2-a]Quinoxalin-2-One

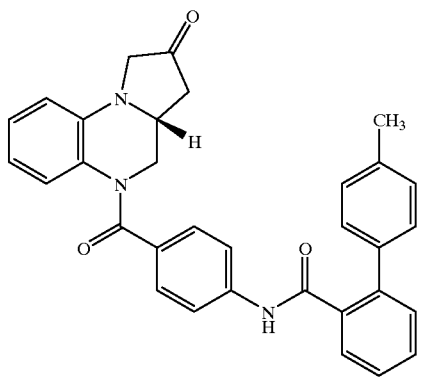

To a solution of dimethyl sulfoxide (0.25 g) in anhydrous dichloromethane (30 ml) cooled to −60° C., there was dropwise added a solution of trifluoroacetic anhydride (0.5 g) in anhydrous dichloromethane (10 ml) over 10 minutes. After stirring the mixture at that temperature for half hour, a solution of (2R,3aR)-2-hydroxy-5-[4-[[2-(4-tolyl)benzoyl]amino]benzoyl]-1,2,3,3a,4,5-hexahydro-pyrrolo[1,2-a]quinoxahine (0.8 g) prepared in Example 14 in anhydrous dichloromethane (10 ml) was dropwise added to the mixture over 10 minutes. After stirring the reaction solution at that temperature for one hour, 0.4 ml of triethylamine was dropwise added thereto and the mixture was stirred at room temperature for 2 hours. The reaction solution was washed, in order, with water, a saturated aqueous sodium bicarbonate solution, a 1N hydrochloic acid solution and water and then dried over anhydrous magnesium sulfate. After concentration of the reaction solution, the resulting residue was subjected to silica gel column chromatography and then eluted with chloroform/ethyl acetate (99/1). The resulting eluate was concentrated and the resulting residue was recrystallized from ethyl acetate-hexane to give 0.44 g (yield 55.3%) of the title compound.

m.p.: 125° C. (decomposition); ¹H-N.M.R. (CDCl₃) δ: 2.35–2.48 (4 H, m), 2.70–2.81 (1 H, m), 2.90–3.00 (1 H, m), 3.69–4.13 (3 H, m), 5.00–5.08 (1 H, m), 6.45–6.51 (1 H, m), 6.97–7.25 (8 H, m), 7.28–7.70 (7 H, m), 7.85–7.90 (1 H, m); I.R. (KBr) vcm⁻¹: 3300, 1760, 1650, 1600, 1505, 1410, 1320, 1250.

EXAMPLE 25

(11aS)-10-[4-[(2-Phenylbenzoyl) Amino]Benzoyl]-1,2,3,10,11, 11a-Hexahydro-5H-Pyrrolo[2,1-c][1,4]Benzodiazepin-5-One

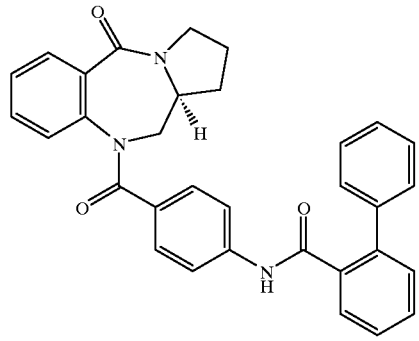

To a solution of 4-[(2-phenylbenzoyl)amino]benzoic acid (1.44 g) in tetrahydrofuran (10 ml), there were added, with ice-cooling, 0.62 g of thionyl chloride and a catalytic amount of N,N-dimethylformamide and the mixture was stirred at room temperature for one hour. After concentration of the reaction solution, the resulting acid chloride was dissolved in 10 ml of tetrahydrofuran and the resulting solution was dropwise added to a solution of (11aS)-1,2,3,10,11,11a-hexahydro-5H-pyrrolo[2,1-c][1,4]benzodiazepin-5-one (4 g) prepared in Reference Example 24 and triethylamine (0.5 g) in tetrahydrofuran (10 ml) with ice-cooling. The reaction solution was stirred for 2 hours under ice-cooling and it was concentrated and dissolved in ethyl acetate. The resulting organic phase was washed with water and then dried over anhydrous magnesium sulfate. The residue obtained after concentration of the reaction solution was subjected to silica gel column chromatography and then eluted with chloroform/ethyl acetate (100/1) to thus give 0.89 g (yield 44.4%) of the title compound.

m.p.: 233–235° C.; ¹H-N.M.R. (CDCl₃) δ: 1.87–1.96 (1 H, m), 2.03–2.19 (3 H, m), 3.58–3.69 (2 H, m), 3.79–3.93 (2 H, m), 4.29 (1 H, t, J=12.8 Hz), 6.64 (1 H, d, J=6.7 Hz), 6.79–6.91 (3 H, m), 7.07 (2 H, d, J=8.4 Hz), 7.13 (1 H, td, J=7.7, 1.8 Hz), 7.23–7.31 (1 H, m), 7.32–7.57 (8 H, m), 7.76 (1 H, dd, J=7.3, 1.5 Hz), 7.86 (1 H, d, J=7.3 Hz); I.R. (KBr) vcm⁻¹: 1630, 1520, 1410, 1360, 1320.

EXAMPLE 26

(11aS)-10-[4-[[2-(4-Tolyl) Benzoyl]Amino]Benzoyl]-1,2,3,10,11,11a-Hexahydro-5H-Pyrrolo[2,1-c][1,4]Benzodiazepin-5-One

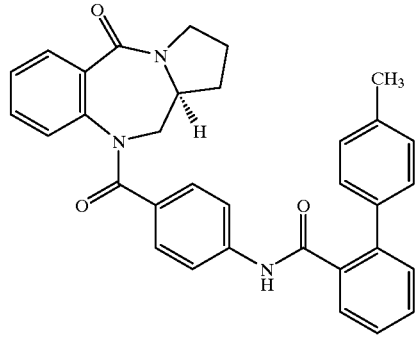

The same procedures used in Example 25 were repeated using (11aS)-1,2,3,10,11,11a-hexahydro-5H-pyrrolo[2,1-c][1,4]benzodiazepin-5-one prepared in Reference Example 24 and 4-[[2-(4-tolyl)benzoyl]amino]benzoic acid to give the title compound. Yield 74.4%.

m.p.: 230–231.5° C.; ¹H-N.M.R. (CDCl₃) δ: 1.86–2.23 (5 H, m), 2.35 (3 H, s), 3.58–3.68 (1 H, m), 3.77–3.94 (1 H, m), 4.29 (1 H, t, J=12.8 Hz), 6.65 (1 H, d, J=9.7 Hz), 6.85–6.94 (3 H, m), 7.05–7.20 (6 H, m), 7.23–7.30 (2 H, m), 7.34–7.55 (3 H, m), 7.76 (1 H, dd, J=7.7, 1.5 Hz), 7.84 (1 H, d, J=7.3 Hz); I.R. (KBr) vcm⁻¹: 1630, 1520, 1460, 1400, 1360, 1320.

REFERENCE EXAMPLE 68

(2R,11aS)-2-(tert-Butyldimethylsilyloxy)-10-[4-[(2-Phenylbenzoyl) Amino]Benzoyl]-1,2,3,10,11,11a-Hexahydro-5H-Pyrrolo [2,1-c][1,4]Benzodiazepin-5-One

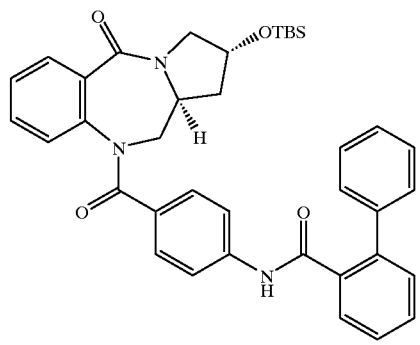

The same procedures used in Example 25 were repeated using (2R, 11aS)-2-(tert-butyldimethylsilyloxy)-1,2,3,10,11,11a-hexahydro-5H-pyrrolo [2,1-c][1,4]benzodiazepin-5-one prepared in Reference Example 26 and 4-[(2-phenylbenzoyl)amino]benzoic acid to give the title compound. Yield 95%.

¹H-N.M.R. (CDCl₃) δ: 0.08 (3 H, s), 0.09 (3 H, s ), 0.86 (9 H, s), 2.04–2.22 (2 H, m), 3.65–3.85 (3 H, m), 3.92–4.40 (1 H, m), 4.24 (1 H, t, J=7.0 Hz), 4.55–4.63 (1 H, m), 6.63 (1 H, d, J=7.8 Hz), 6.80 (1 H, s), 6.89 (2 H, d, J=8.5 Hz), 7.07 (2 H, d, J=8.5 Hz), 7.10–7.17 (1 H, m), 7.27–7.56 (9 H, m), 7.75 (1 H, d, J=7.8 Hz), 7.86 (1 H, d, J=7.8 Hz); I.R. (KBr) vcm⁻¹: 3300, 1630, 1600, 1520, 1400, 1320.

EXAMPLE 27

(2R,11aS)-2-Hydroxy-10-[4-[(2-Phenylbenzoyl)
Amino]Benzoyl]-1,2,3,10,11,11a-Hexahydro-5H-
Pyrrolo[2,1-c][1,4]Benzodiazepin-5-One

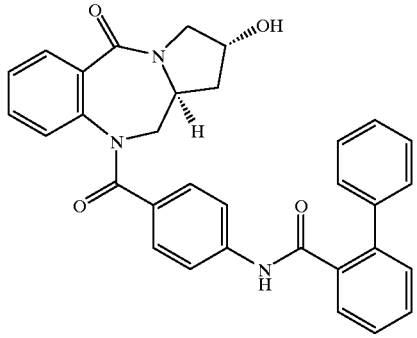

To a solution of (2R,11aS)-2-(tert-butyldimethylsilyloxy)-10-[4-[(2-phenylbenzoyl)amino]benzoyl]-1,2,3,10,11,11a-hexahydro-5H-pyrrolo[2,1-c][1,4]benzodiazepin-5-one (5.53 g) prepared in Reference Example 68 in tetrahydrofuran (20 ml), there was dropwise added, with ice-cooling, a solution of tetrabutylammonium fluoride (4.54 g) in tetrahydrofuran (50 ml) over 5 minutes and the reaction solution was stirred at room temperature for 30 minutes. After the reaction solution was diluted with ethyl acetate, it was washed with water and then dried over anhydrous magnesium sulfate. The residue obtained after concentration of the reaction solution was subjected to silica gel column chromatography and then eluted with chloroform/acetone (1/1) to give 4.1 g (yield 91.0%) of the title compound.

m.p.: 176–178° C.; $^1$H-N.M.R. (CDCl$_3$) δ: 2.00–2.15 (1 H, m), 2.17 (1 H, brs), 2.25–2.35 (1 H, m), 3.65–3.80 (1 H, m), 3.95–4.15 (2 H, m), 4.25 (1 H, t, J=12.4 Hz), 4.65 (1 H, brs), 6.64 (1 H, d, J=7.8 Hz), 6.82–6.92 (3 H, m), 7.04 (2 H, d, J=8.5 Hz), 7.13 (1 H, t, J=7.8 Hz), 7.30–7.55 (9 H, m), 7.74 (1 H, d, J=7.8 Hz), 7.85 (1 H, d, J=7.8 Hz); I.R. (KBr) vcm$^{-1}$: 1630, 1410, 1320.

EXAMPLE 28

(2S, 11aS)-2-Acetoxy-10-[4-[(2-Phenylbenzoyl)
Amino]Benzoyl]-1,2,3,10,11,11a-Hexahydro-5H-
Pyrrolo[2,1-c][1,4]Benzodiazepin-5-One

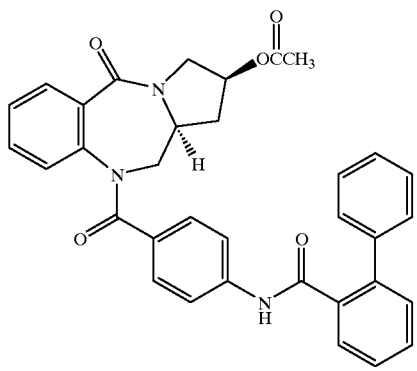

The same procedures used in Example 5 were repeated using (2R, 11aS)-2-hydroxy-10-[4-[(2-phenylbenzoyl)amino]benzoyl]-1,2,3,10,11,11a-hexahydro-5H-pyrrolo[2,1-c][11,4]benzodiazepin-5-one prepared in Example 27 to give the title compound in the form of amorphous powder. Yield 66.6%.

$^1$H-N.M.R. (CDCl$_3$) δ: 2.11 (3 H, s), 2.05–2.55 (1 H, m), 2.42–2.55 (1 H, m), 3.61 (1 H, dd, J=12.7, 4.4 Hz), 3.85–4.10 (3 H, m), 4.69 (1 H, t, J=12.4 Hz), 5.45 (1 H, brs), 6.67 (1 H, d, J=7.8 Hz), 6.85–6.95 (3 H, m), 7.08 (2 H, d, J=8.5 Hz), 7.16 (1 H, t, J=7.8 Hz), 7.30–7.60 (9 H, m), 7.76 (1 H, d, J=7.8 Hz), 7.85 (1 H, d, J=7.8 Hz); I.R. (KBr) vcm$^{-1}$: 3400, 1740, 1640, 1520, 1400, 1240.

EXAMPLE 29

(2S, 11aS)-2-Hydroxy-10-[4-[(2-Phenylbenzoyl)
Amino]Benzoyl]-1,2,3,10,11,11a-Hexahydro-5H-
Pyrrolo[2,1-c][1,4]Benzodiazepin-5-One

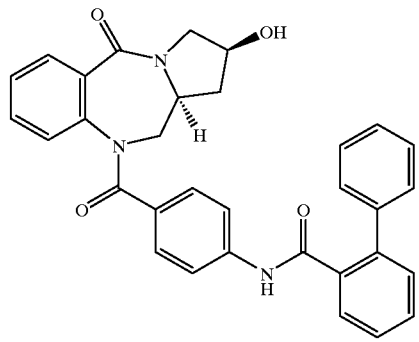

The same procedures used in Example 7 were repeated using (2S, 11aS)-2-acetoxy-10-[4-[(2-phenylbenzoyl)amino]benzoyl]-1,2,3,10,11,11a-hexahydro-5H-pyrrolo[2,1-c][1,4]benzodiazepin-5-one prepared in Example 28 to give the title compound. Yield 70%.

m.p. 254–255° C.; $^1$H-N.M.R. (CDCl$_3$) δ: 2.05 (1 H, brd, J=13.9 Hz), 2.24–2.36 (1 H, m), 3.15 (1 H, d, J=3.4 Hz), 3.62 (1 H, dd, J=12.7, 4.6 Hz), 3.77–3.98 (3 H, m), 4.62 (1 H, brs), 4.89 (1 H, t, J=12.7 Hz), 6.68 (1 H, d, J=7.8 Hz), 6.87 (2 H, d, J=8.5 Hz), 6.99 (1 H, s), 7.04 (2 H, d, J=8.5 Hz), 7.14 (1 H, td, J=7.8, 1.4 Hz), 7.24–7.57 (9 H, m), 7.72 (1 H, dd, J=7.8, 1.4 Hz), 7.83 (1 H, d, J=7.8 Hz); I.R. (KBr) vcm$^{-1}$: 1620, 1520, 1410, 1320.

EXAMPLE 30

(11aS)-10-[4-[(2-Phenylbenzoyl) Amino]Benzoyl]-1,2,3,10,11, 11a-Hexahydro-5H-Pyrrolo [2,1-c][1,4] Benzodiazepin-2,5-Dione

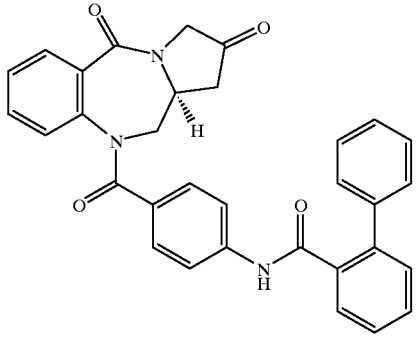

The same procedures used in Example 24 were repeated using (2R, 11aS)-2-hydroxy-10-[4-[(2-phenylbenzoyl)amino]benzoyl]-1,2,3,10,11,11a-hexahydro-5H-pyrrolo[2,1-c][1,4]benzodiazepin-5-one obtained in Example 27 to thus give the title compound. Yield 75.4%.

m.p.: 159–169° C.; $^1$H-N.M.R. (CDCl$_3$) δ:2.50–2.63 (1 H, m), 2.93–3.05 (1 H, m), 3.69–3.83 (1 H, m), 3.98–4.11 (1 H, m), 4.28–4.45 (3 H, m), 6.66–6.72 (1 H, m), 6.84–6.95 (3 H, m), 7.06 (2 H, d, J=8.8 Hz), 7.21 (1 H, td, J=7.7, 1.8 Hz), 7.30–7.58 (9 H, m), 7.76 (1 H, dd, J=7.7, 1.5 Hz), 7.85 (1 H, dd, J=7.7, 1.5 Hz); I.R. (KBr) vcm$^{-1}$: 3300, 1760, 1650, 1600, 1505, 1410, 1320, 1250.

EXAMPLE 31

(11aR)-10-[4-[(2-Phenylbenzoyl) Amino]Benzoyl]-1,2,3,10,11, 11a-Hexahydro-5H-Pyrrolo[2,1-c][1,4] Benzodiazepin-5-One

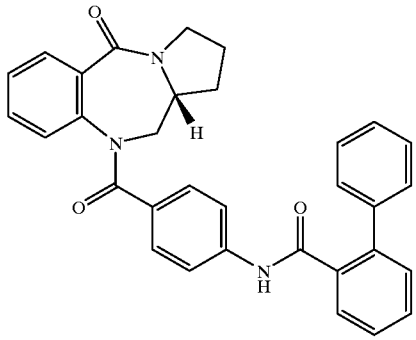

The same procedures used in Example 25 were repeated using (11aR)-1,2,3,10,11,11a-hexahydro-5H-pyrrolo[2,1-c][1,4]benzodiazepin-5-one prepared in Reference Example 25 and 4-[(2-phenylbenzoyl)amino]benzoic acid to thus give the title compound. Yield 43.0%.

m.p.: 233–235° C.; $^1$H-N.M.R. (CDCl$_3$) δ: 1.87–1.96 (1 H, m), 2.03–2.19 (3 H, m), 3.58–3.69 (2 H, m), 3.79–3.93 (2 H, m), 4.29 (1 H, t, J=12.8 Hz), 6.64 (1 H, d, J=6.7 Hz), 6.79–6.91 (3 H, m), 7.07 (2 H, d, J=8.4 Hz), 7.13 (1 H, td, J=7.7, 1.8 Hz), 7.23–7.31 (1 H, m), 7.32–7.57 (8 H, m), 7.76 (1 H, dd, J=7.3, 1.5 Hz), 7.86 (1 H, d, J=7.3 Hz); I.R. (KBr) vcm$^{-1}$: 1630, 1520, 1410, 1360, 1320.

REFERENCE EXAMPLE 69

(2R,11aR)-2-(tert-Butyldimethylsilyloxy) 10-[4-[(2-Phenylbenzoyl) Amino]Benzoyl]-1,2,3,10,11,11a-Hexahydro-5H-Pyrrolo [2,1-c][1,4]Benzodiazepin-5-One

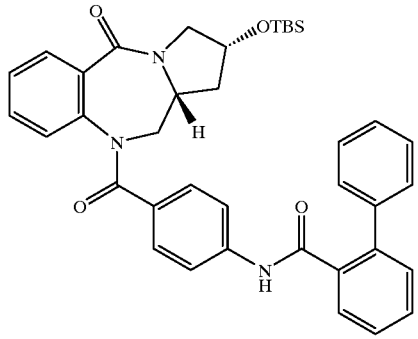

The same procedures used in Example 25 were repeated using (2R, 11aR)-2-(tert-butyldimethylsilyloxy)-1,2,3,10, 11,11a-hexahydro-5H-pyrrolo [2,1-c][1,4]benzodiazepin-5-one prepared in Reference Example 27 and 4-[(2-phenylbenzoyl)amino]benzoic acid to thus give the title compound.

Yield 95.2%.; $^1$H-N.M.R. (CDCl$_3$) δ: 0.10 (3 H, s), 0.12 (3 H, s), 0.91 (9 H, s), 1.88–2.00 (1 H, m), 2.24–2.36 (1 H, m), 3.55–3.99 (4 H, m), 4.51–4.58 (1 H, m), 4.80–4.94 (1 H, m), 6.63 (1 H, d, J=7.6 Hz), 6.83–6.95 (3 H, m), 7.04–7.16 (3 H, m), 7.22–7.57 (8 H, m), 7.71–7.87 (2 H, m); I.R. (KBr) vcm$^{-1}$: 3450, 1640, 1520, 1410, 1360, 1320, 1250.

EXAMPLE 32

(2R,11aR)-2-Hydroxy-10-[4-[(2-Phenylbenzoyl) Amino]Benzoyl]-1,2,3,10,11,11a-Hexahydro-5H-Pyrrolo[2,1-c][1,4]Benzodiazepin-5-One

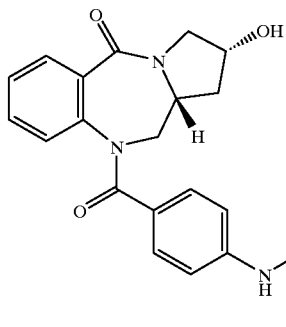

The same procedures used in Example 27 were repeated using (2R, 11aR)-2-(tert-butyldimethylsilyloxy)-1,2,3,10, 11,11a-hexahydro-5H-pyrrolo [2,1-c][1,4]benzodiazepin-5-one prepared in Reference Example 69 to thus give the title compound. Yield 53.6%.

m.p.: 254–255° C. $^1$H-N.M.R. (CDCl$_3$) δ: 1.87 (1 H, d, J=13.9 Hz), 2.18–2.33 (1 H, m), 3.49–3.69 (3 H, m), 3.77–3.90 (1 H, m), 4.39–4.47 (1 H, m), 4.46–4.76 (1 H, m), 5.21 (1 H, brs), 6.75–6.84 (1 H, m), 6.99 (2 H, d, J=8.3 Hz), 7.20–7.64 (14 H, m); I.R. (KBr) vcm$^{-1}$: 3450, 1630, 1520, 1410, 1320, 1260.

EXAMPLE 33

(2S, 11aR)-2-Acetoxy-10-[4-[(2-Phenylbenzoyl) Amino]Benzoyl]-1,2,3,10,11,11a-Hexahydro-5H-Pyrrolo[2,1-c][1,4]Benzodiazepin-5-One

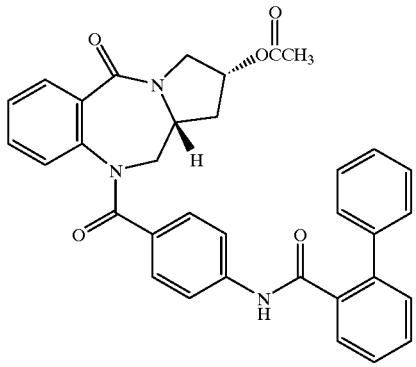

The same procedures used in Example 5 were repeated using (2R, 11aR)-2-hydroxy-10-[4-[(2-phenylbenzoyl)amino]benzoyl]-1,2,3,10,11,11a-hexahydro-5H-pyrrolo[2,1-c][1,4]benzodiazepin-5-one prepared in Example 32 to thus give the title compound as amorphous powder. Yield 66.6%.

$^1$H-N.M.R. (CDCl$_3$) δ: 2.04 (3 H, s), 2.15–2.27 (1 H, m), 2.33–2.46 (1 H, m), 3.74–3.90 (2 H, m), 3.99–4.34 (3 H, m), 5.37–5.46 (1 H, m), 6.65 (1 H, d, J=7.8 Hz), 6.83–6.94 (3 H, m), 7.02–7.20 (3 H, m), 7.25–7.58 (8 H, m), 7.77–7.90 (2 H, m); I.R. (KBr) vcm$^{-1}$: 3400, 1740, 1640, 1520, 1400, 1240.

EXAMPLE 34

(2S, 11aR)-2-Hydroxy-10-[4-[(2-Phenylbenzoyl) Amino]Benzoyl]-1,2,3,10,11,11a-Hexahydro-5H-Pyrrolo[2,1-c][1,4]Benzodiazepin-5-One

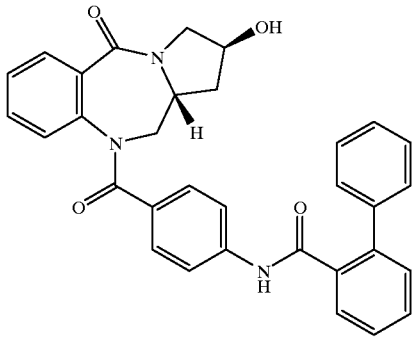

The same procedures used in Example 7 were repeated using (2S, 11aR)-2-acetoxy-10-[4-[(2-phenylbenzoyl)amino]benzoyl]-1,2,3,10,11,11, a-hexahyro-5H-pyrrolo[2,1-c][1,4]benzodiazepin-5-one prepared in Example 33 to thus give the title compound. Yield 67.7%.

m.p.: 169–170° C.; $^1$H-N.M.R. (CDCl$_3$) δ: 2.01–2.18 (1 H, m), 24–2.36 (1 H, m), 3.70–3.81 (2 H, m), 3.94– 4.13 (2 H, m), 4.26 (1 H, t, J=12.5 Hz), 4.62–4.70 (1 H, m), 6.64 (1 H, d, J=7.8 Hz), 6.84–6.93 (3 H, m), 7.05 (2 H, d, J=8.8 Hz), 7.13 (1 H, d t, J=7.8, 1.7 Hz), 7.24–7.57 (8 H, m), 7.74 (1 H, dd, J=7.8, 1.7 Hz), 7.86 (1 H, d, J=7.6 Hz); I.R. (KBr) vcm$^{-1}$: 3400, 1630, 1520, 1400, 1310.

REFERENCE EXAMPLE 70

(2S, 11aR)-10-[4-[(2-Phenylbenzoyl) Amino] Benzoyl]-2-Phthalimido-1,2,3,10,11,11a-Hexahydro-5H-Pyrrolo[2,1-c][1,4]Benzodiazepin-5-One

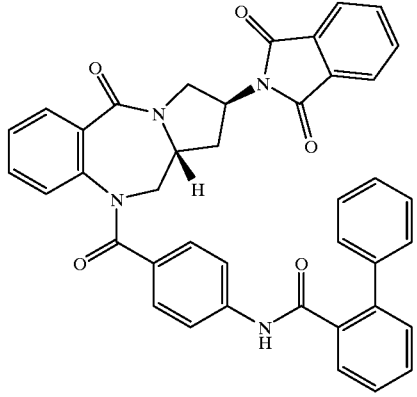

The same procedures used in Reference Example 65 were repeated using (2R,11aR)-2-hydroxy-10-[4-[(2-phenylbenzoyl)amino]benzoyl]-1,2,3,10,11,11a-hexahyro-5H-pyrrolo[2,1-c][1,4]benzodiazepin-5-one obtained in Example 32 to thus give the title compound as amorphous powder. Yield 94.0%.

$^1$H-N.M.R. (CDCl$_3$) δ: 2.11–2.20 (1 H, m), 2.96–3.09 (1 H, m), 3.66–3.74 (1 H, m), 3.97–4.66 (4 H, m), 5.11–5.27 (1 H, m), 6.66 (1 H, d, J=8.1 Hz), 6.86–7.88 (20 H, m); I.R. (KBr) cm$^{-1}$: 3450, 1780, 1720, 1640, 1520, 1400, 1250, 1180.

EXAMPLE 35

(2S, 11 aR)-10-[4-[(2-Phenylbenzoyl) Amino] Benzoyl]-2-Phthalimido-1,2,3,10,11,11a-Hexahydro-5H-Pyrrolo[2,1-c][1,4]Benzodiazepin-5-One

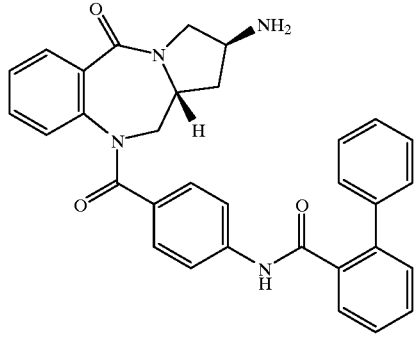

The same procedures used in Example 9 were repeated using (2S, 11aR)-10-[4-[(2-phenylbenzoyl)amino]benzoyl]-2-phthalimido-1,2,3,10,11, 11a-hexahydro-5H-pyrrolo[2,1-c][1,4]benzodiazepin-5-one prepared in Reference Example 70 to thus give the title compound in the form of amorphous powder. Yield 45.5%.

$^1$H-N.M.R. (CDCl$_3$) δ: 1.92–2.16 (2 H, m), 3.43 (1 H, dd, J=11.2, 6.4 Hz), 3.65 (1 H, dd, J=12.7, 4.4 Hz), 3.81–4.05 (3 H, m), 4.30 (1 H, t, J=12.7 Hz), 6.63 (1 H, d, J=7.8 Hz), 6.83–6.91 (3 H, m), 7.02–7.17 (3 H, m), 7.24–7.57 (10 H, m), 7.76 (1 H, dd, J=7.6, 1.7 Hz), 7.86 (1 H, d, J=7.3 Hz); I.R. (KBr) vcm$^{-1}$: 3400, 1630, 1520, 1460, 1410, 1360, 1320, 1250.

EXAMPLE 36

(2S, 11aR)-2-(N,N-Dimethylamino)-10-[4-[(2-Phenylbenzoyl) Amino]Benzoyl]-1,2,3,10,11,11a-Hexahydro-5H-Pyrrolo[2,1-c][1,4]Benzodiazepin-5-One Hydrochloride

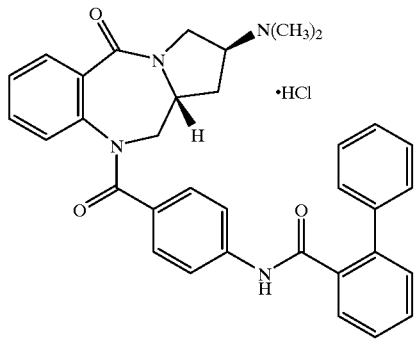

The same procedures used in Example 10 were repeated using (2S, 11aR)-2-amino-10-[4-[(2-phenylbenzoyl)amino] benzoyl]-1,2,3,10,11,11a-hexahydro-5H-pyrrolo[2,1-c][1,4] benzodiazepin-5-one prepared in Example 35 to give the title compound. Yield 67.8%.

m.p: 201–203° C.; $^1$H-N.M.R. (DMSO-d$_6$) δ: 2.30–2.53 (2 H, m), 2.80 (3 H, s), 2.81 (3 H, s), 3.54–3.65 (1 H, m), 3.70–3.83 (1 H, m), 3.96–4.31 (4 H, m), 6.85 (1 H, d, J=7.8 Hz), 6.98 (2 H, d, J=8.3 Hz), 7.23–7.66 (14 H, m), 10.31 (1 H, brs), 11.34 (1 H. brs); I.R. (KBr) vcm$^{-1}$: 3400, 1630, 1520, 1460, 1410, 1320.

EXAMPLE 37

(11aS)-10-[4-[(2-Phenylbenzoyl) Amino]Benzoyl]-1,2,3,10,11, 11a-Hexahydro-5H-Pyrrolo[2,1-c][1,4]Benzodiazepin-5-Thione

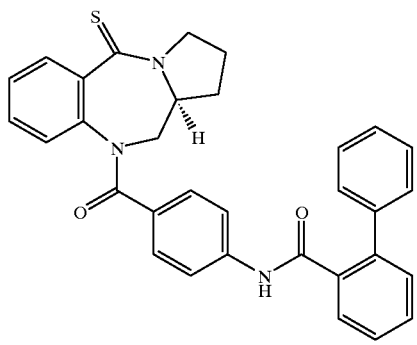

The same procedures used in Example 25 were repeated using (11aS)-1,2,3,10,11,11a-hexahydro-5H-pyrrolo[2,1-c][1,4]benzodiazepin-5-thione prepared in Reference Example 32 and 4-[(2-phenylbenzoyl)amino]benzoic acid to give the title compound. Yield 81.9%.

m.p.: 234–236° C.; $^1$H-N.M.R. (CDCl$_3$) δ: 1.90–2.05 (1 H, m), 2.15–2.35 (3 H, m), 3.62 (1 H, dd, J=12.0, 4.6 Hz), 3.75–3.90 (1 H, m), 4.05–4.30 (2 H, m), 4.43 (1 H, t, J=12.0 Hz), 6.57 (1 H, d, J=7.8 Hz), 6.82 (1 H, s), 6.92 (2 H, t, J=8.3 Hz), 7.05–7.50 (12 H, m), 7.84 (1 H, d, J=7.8 Hz), 7.95 (1 H, d, J=7.8 Hz); I.R. (KBr) vcm$^{-1}$: 1640, 1625, 1515, 1475, 1250.

EXAMPLE 38

(11aS)-10-[4-[[2-(4-Tolyl) Benzoyl]Amino] Benzoyl]-1,2,3,10,11, 11a-Hexahydro-5H-Pyrrolo[2, 1-c][1,4]Benzodiazepin-5-Thione

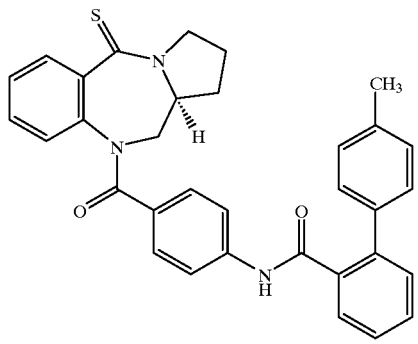

The same procedures used in Example 25 were repeated using (11aS)-1,2,3,10,11,11a-hexahydro-5H-pyrrolo[2,1-c][1,4]benzodiazepin-5-thione prepared in Reference Example 32 and 4-[[2-(4-tolyl)benzoyl]amino]benzoic acid to thus give the title compound. Yield 59.4%.

m.p.: 140–145° C.; $^1$H-N.M.R. (CDCl$_3$) δ: 1.90–2.19 (1 H, m), 2.19–2.31 (3 H, m), 2.35 (3 H, s), 3.62 (1 H, dd, J=12.7, 4.4 Hz), 3.82–3.90 (1 H, m), 4.09–4.25 (2 H, m), 4.44 (1 H, t, J=12.7 Hz), 6.59 (1 H, d, J=7.8 Hz), 6.85–6.94 (3 H, m), 7.07–7.53 (10 H, m), 7.82 (1 H, d, J=6.6 Hz), 7.93 (1 H, d, J=7.8 Hz); I.R. (KBr) vcm$^{-1}$: 3300, 1640, 1600, 1520, 1480, 1330.

EXAMPLE 39

(11R)-10-[4-[(2-Phenylbenzoyl) Amino]Benzoyl]-1, 2,3,10,11, 11a-Hexahydro-5H-Pyrrolo[2,1-c][1,4]Benzodiazepin-5-Thione

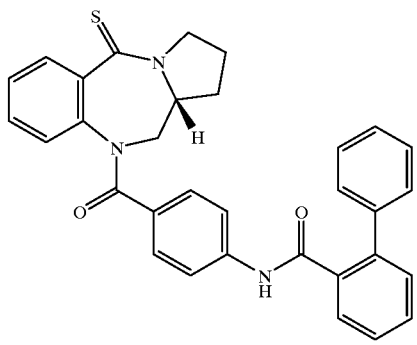

The same procedures used in Example 25 were repeated using (11aR)-1,2,3,10,11,11a-hexahydro-5H-pyrrolo[2,1-c][1,4]benzodiazepin-5-thione prepared in Reference Example 33 and 4-[(2-phenylbenzoyl)amino]benzoic acid to give the title compound. Yield 58%.

m.p.: 234–236° C.; $^1$H-N.M.R. (CDCl$_3$) δ: 1.90–2.05 (1 H, m), 2.15–2.35(3 H, m), 3.62 (1 H, dd, J=12.0, 4.6 Hz), 3.75–3.90 (1 H, m), 4.05–4.30 (2 H, m), 4.43 (1 H, t, J=12.0 Hz), 6.57 (1 H, d, J=7.8 Hz), 6.82 (1 H, s), 6.92 (2 H, t, J=8.3 Hz), 7.05–7.50 (8 H, m), 7.84 (1 H, d, J=7.8 Hz), 7.95 (1 H, d, J=7.8 Hz); I.R. (KBr) vcm$^{-1}$: 1640, 1625, 1515, 1475, 1250.

EXAMPLE 40

(11aS)10-[4-[(2-Phenylbenzoyl) Amino]Benzoyl]-1,2,3,10,11, 11a-Hexahydro-Pyrrolo[1,2-b][1,2,5]Benzothiadiazepin-5,5-Dioxide

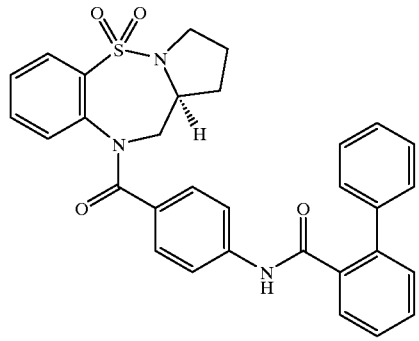

To a solution of 2-phenyl benzoic acid (0.1 g) in tetrahydrofuran (2 ml), there was added, with ice-cooling, 0.075 g of thionyl chloride and a catalytic amount of N,N-dimethylformamide and the mixture was heated under reflux for 2 hours. After concentration of the reaction solution, the resulting acid chloride was dissolved in 3 ml of dichloromethane and the resulting solution was dropwise added to a solution of (11aS)-10-(4-aminobenzoyl)-1,2,3,10,11,11a-hexahydro-pyrrolo[1,2-b][1,2,5]benzothiadiazepin-5,5-dioxide (0.15 g) prepared in Reference Example 37 and pyridine (0.05 g) in dichloromethane (3 ml) at room temperature for 15 minutes. After stirring the reaction solution at room temperature for 3 hours, it was poured into ice water and then extracted with ethyl acetate. The resulting organic phase was washed with water and dried over anhydrous magnesium sulfate. After concentration of the organic phase, the resulting residue was subjected to silica gel column chromatography and then eluted with chloroform/methanol (49/1) to thus give 0.05 g (yield 22.6%) of the title compound.

m.p.: 142–143° C.; $^1$H-N.M.R. (CDCl$_3$) δ: 1.67–2.16 (3 H, m), 2.27–2.43 (1 H, m), 2.61 (1 H, dd, J=14.3, 11.4 Hz), 3.00–3.13 (1 H, m), 3.60–3.71 (1 H, m), 4.34–4.47 (1 H, m), 4.90–5.01 (1 H, m), 6.74–6.96 (4 H, m), 7.20–7.58 (11 H, m), 7.87 (1 H, d, J=7.3 Hz), 8.01 (1 H, dd, J=7.7, 1.5 Hz); I.R. (KBr) vcm$^{-1}$: 1650, 1600, 1520, 1480, 1330, 1160.

EXAMPLE 41

(11aS)-10-[4-[(2-Phenylbenzoyl) Amino]Benzoyl]-1,2,3,10,11, 11a-Hexahydro-5H-Pyrrolo[12,1-c][1,4]Benzodiazepine Hydrochloride

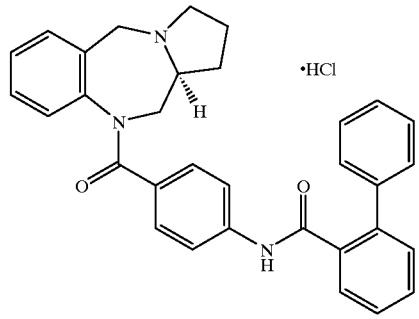

The same procedures used in Example 25 were repeated using (11aS)-1,2,3,10,11,11a-hexahydro-5H-pyrrolo[2,1-c][1,4]benzodiazepine prepared in Reference Example 28 and 4-[(2-phenylbenzoyl)amino]benzoic acid to give (11aS)-10-[4-[(2-phenylbenzoyl)amino]benzoyl]-1,2,3,10,11, 11a-hexahydro-5H-pyrrolo[2,1-c][1,4]benzodiazepine. The resulting (11aS)-10-[4-[(2-phenylbenzoyl)amino]benzoyl]-1,2,3,10,11,11a-hexahydro-5H-pyrrolo[2,1-c][1,4]benzodiazepine was dissolved in ethyl acetate, a 4N hydrochloric acid-ethyl acetate solution was added thereto, the resulting precipitates were recovered through filtration and washed with a small amount of ethyl acetate to thus give the title compound. Yield 62.4%.

m.p.: 176–177° C.; $^1$H-N.M.R. (CDCl$_3$) δ: 1.82–2.26 (4 H, m), 2.82–3.13 (1 H, m), 3.40–3.69 (2 H, m), 3.95–4.18 (1 H, m), 4.30–4.68 (2 H, m), 5.18–5.40 (1 H, m), 6.68–6.73 (1 H, m), 6.99–7.87 (15 H, m), 7.81 (1 H, m), 12.7–13.2 (1 H, m); I.R. (KBr) vcm$^{-1}$: 1640, 1600, 1520, 1400, 1320, 1270.

EXAMPLE 42

(2R,11aS)-2-Hydroxy-10-[4-[(2-Phenylbenzoyl) Amino]Benzoyl]-1,2,3,10,11,11a-Hexahydro-5H-Pyrrolo[2,1-c][1,4]Benzodiazepine Hydrochloride

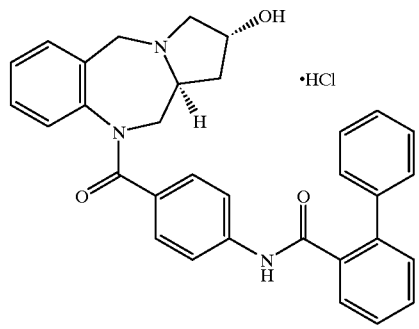

The same procedures used in Example 41 were repeated using (2R, 11aS)-2-hydroxy-1,2,3,10,11,11a-hexahydro-5H-pyrrolo[2,1-c][1,4]Benzodiazepine obtained in Reference Example 30 and 4-[(2-phenylbenzoyl) amino]benzoic acid to thus give the title compound. Yield 86%.

m.p.: 245–248° C.; $^1$H-N.M.R. (DMSO-d$_6$+D$_2$O) δ: 1.91–2.20 (2 H, m), 2.92–3.27 (2 H, m), 3.99–4.21 (2 H, m), 4.40–4.55 (1 H, m), 4.65 (1 H, d, J=13.5 Hz), 4.84–5.00 (1 H, m), 5.14–5.31 (1 H, m), 6.76 (1 H, d, J=7.3 Hz), 7.15 (2 H, d, J=7.7 Hz), 7.21–7.66 (14 H, m), 10.30 (1 H, s); I.R. (KBr) vcm$^{-1}$: 3280, 1630, 1580, 1520, 1410, 1320.

EXAMPLE 43

(11aR)-10-[4-[(2-Phenylbenzoyl) Amino]Benzoyl]-1,2,3,10,11, 11a-Hexahydro-5H-Pyrrolo[2,1-c][1,4] Benzodiazepine Hydrochloride

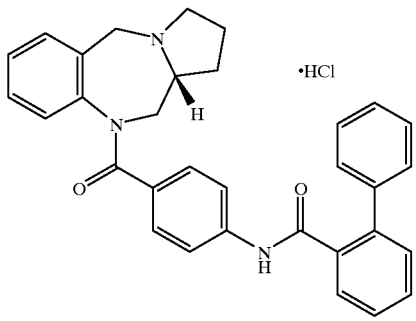

The same procedures used in Example 41 were repeated using (11aR)-1,2,3,10,11,11a-hexahydro-5H-pyrrolo[2,1-c][1,4]benzodiazepine obtained in Reference Example 29 and 4-[(2-phenylbenzoyl)amino]benzoic acid to thus give the title compound. Yield 80.5% m.p.: 176–177° C. $^{1}$H-N.M.R. (CDCl$_{3}$) δ: 1.82–2.26 (4 H, m), 2.82–3.13 (1 H, m), 3.40–3.69 (2 H, m), 3 . 95–4.18 (1 H, m), 4.30–4.68 (2 H, m), 5.18–5.40 (1 H, m), 6.68–6.73 (1 H, m), 6.99–7.87 (15 H, m), 7.81 (1 H, m), 12.7–13.2 (1 H, m); I.R. (KBr) vcm$^{-1}$: 1640, 1600, 1520, 1400, 1320, 1270.

EXAMPLE 44

(11aR)-10-[4-[[2-(4-Tolyl) Benzoyl]Amino]Benzoyl]-1,2,3,10,11, 11-Hexahydro-5H-Pyrrolo[2,1-c][1,4]Benzodiazepine Hydrochloride

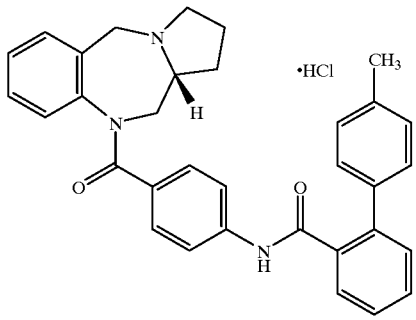

The same procedures used in Example 41 were repeated using (11aR)-1,2,3,10,11,11a-hexahydro-5H-pyrrolo[2,1-c][1,4]benzodiazepine obtained in Reference Example 29 and 4-[[2-(4-tolyl)benzoyl]amino]benzoic acid to thus give the title compound. Yield 53.6%.

m.p.: 200–202° C.; $^{1}$H-N.M.R. (CDCl$_{3}$) δ: 1.51–1.72 (3 H, m), 1.88 (1 H, brs), 2.15–2.26 (1 H, m), 2.35 (3 H, s), 2.42–2.53 (1 H, m), 3.40–3.59 (2 H, m), 3.95–4.08 (1 H, m), 4.68 (1 H, brs), 4.95–5.08 (1 H, m), 6.28–6.38 (1 H, m), 6.51 (2 H, d, J=7.0 Hz), 6.89–7.55 (13 H, m), 7.31–7.58 (2 H, m), 8.26 (1 H, d, J=7.3 Hz); I.R. (KBr) vcm$^{-1}$: 1660, 1640, 1600, 1520, 1400, 1320.

EXAMPLE 45

(2R,11aR)-2-Hydroxy-10-[4-[(2-Phenylbenzoyl) Amino]Benzoyl]-1,2,3,10,11,11a-Hexahydro-5H-Pyrrolo[2,1-c][1,4]Benzodiazepine Hydrochloride

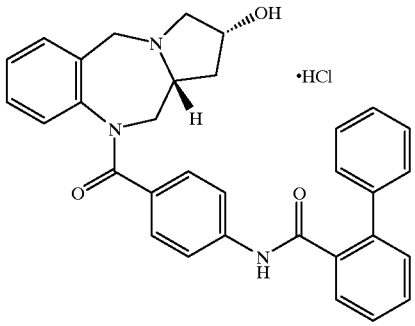

The same procedures used in Example 41 were repeated using (2R, 11aR)-2-hydroxy-1,2,3,10,11,11a-hexahydro-5H-pyrrolo[2,1-c][1,4]benzodiazepine obtained in Reference Example 31 and 4-[(2-phenylbenzoyl) amino]benzoic acid to thus give the title compound. Yield 83.6%.

m.p.: 160–162° C.; $^{1}$H-N.M.R. (CDCl$_{3}$) δ: 1.36–1.48 (1 H, m), 2.18–2.51 (1 H, m), 3.08–3.30 (2 H, m), 3.76–3.88 (2 H, m), 4.21–4.30 (1 H, m), 5.72 (1 H, s), 6.70 (1 H, d, J=7.3 Hz), 6.86–7.15 (7 H, m), 7.26–7.56 (8 H, m), 7.83 (1 H, d, J=7.7 Hz); I.R. (KBr) vcm$^{-1}$: 1620, 1600, 1520, 1400, 1320.

EXAMPLE 46

(2S, 11aR)-2-Acetoxy-10-[4-[(2-Phenylbenzoyl) Amino]Benzoyl]-1,2,3,10,11,11a-Hexahydro-5H-Pyrrolo[2,1-c][1,4]Benzodiazepine

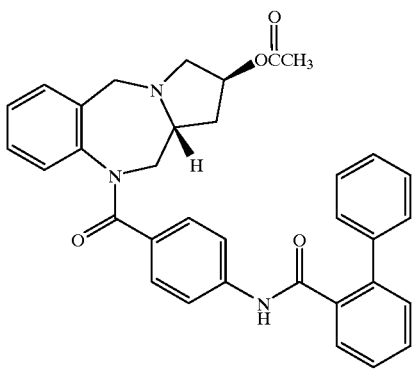

The same procedures used in Example 5 were repeated using (2R, 1aR)-2-hydroxy-10-[4-[(2-phenylbenzoyl) amino]benzoyl]-1,2,3,10,11,11a-hexahydro-5H-pyrrolo[2,1-c][1,4]benzodiazepine prepared in Example 45 and obtained in the form of free base to thus give the title compound. Yield 56.0%.

m.p.: 116–118° C.; $^{1}$H-N.M.R. (CDCl$_{3}$) δ: 1.81–2.00 (1 H, m), 2.04–2.12 (4 H, m), 2.56–2.69 (2 H, m), 2.98–3.13 (1 H, m), 2.56–3.66 (1 H, m), 3.86 (1 H, d, J=13.5 Hz), 3.92 (1 H, d, J=13.5 Hz), 5.05–5.21 (2 H, m), 6.61 (1 H, d, J=7.3 Hz), 6.83–7.15 (7 H, m), 7.24–7.58 (8 H, m), 7.85 (1 H, d, J=7.4 Hz); I.R. (KBr) vcm$^{-1}$: 3250, 1740, 1680, 1630, 1605, 1530, 1325, 1250.

EXAMPLE 47

(2S, 11aR)-2-Hydroxy-10-[4-[(2-Phenylbenzoyl) Amino]Benzoyl]-1,2,3,10,11,11a-Hexahydro-5H-Pyrrolo[2,1-c][1,4]Benzodiazepine Hydrochloride

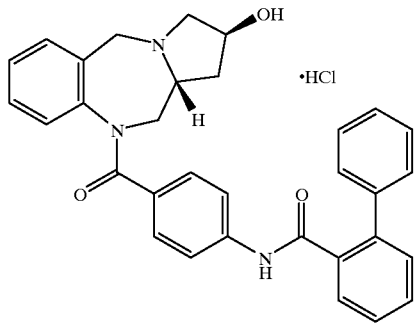

The same procedures used in Example 7 were repeated using (2S, 11aR)-2-acetoxy-10-[4-[(2-phenylbenzoyl)amino]benzoyl]-1,2,3,10,11,11a-hexahydro-5H-pyrrolo[2,1-c][1,4]benzodiazepine obtained in Example 46 to give (2S, 11aR)-2-hydroxy-10-[4-[(2-phenylbenzoyl)amino]benzoyl]-1,2,3,10,11,11a-hexahydro-5H-pyrrolo[2,1-c][1,4]benzodiazepine. The resulting (2S, 11aR)-2-hydroxy-10-[4-[(2-phenylbenzoyl)amino]benzoyl]-1,2,3,10,11,11a-hexahydro-5H-pyrrolo[2,1-c][1,4]benzodiazepine was dissolved in ethyl acetate, followed by addition of a 4N hydrochloric acid-ethyl acetate solution thereto, removal of the resulting precipitates through filtration and washing them with a small amount of ethyl acetate to give the title compound. Yield 33.2%.

m.p.: 245–248° C.; $^1$H-N.M.R. (DMSO-$d_6$+$D_2O$) δ: 1.91–2.20 (2 H, m), 2.92–3.27 (2 H, m), 3.99–4.21 (2 H, m), 4.40–4.55 (1 H, m), 4.65 (1 H, d, J=13.5 Hz ), 4.84–5.00 (1 H, m), 5.14–5.31 (1 H, m), 6.76 (1 H, d, J=7.3 Hz), 7.15 (2 H, d, J=7.7 Hz ), 7.21–7.66 (14 H, m), 10.30 (1 H, s); I.R. (KBr) vcm$^{-1}$: 3280, 1630, 1580, 1520, 1410, 1320.

EXAMPLE 48

(11aR)-10-[4-[(2-Phenylbenzoyl) Amino]Benzoyl]-1,2,3,10,11, 11a-Hexahydro-5H-Pyrrolo[2,1-c][1,4] Benzodiazepin-2-One Hydrochloride

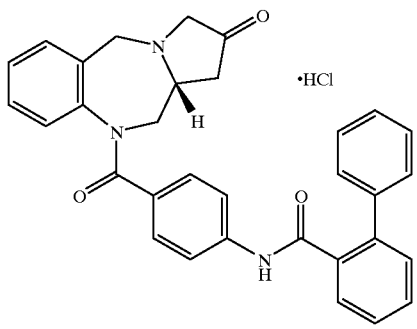

To a solution of (2R,11aR)-2-hydroxy-10-[4-[(2-phenylbenzoyl)amino]benzoyl]-1,2,3,10,11,11a-hexahydro-5H-pyrrolo[2,1-c][1,4]benzodiazepine (0.4 g) prepared in Example 45 and obtained in the form of free base in dimethyl sulfoxide (8 ml), there was added, at room temperature, 1.6 g of N,N'-dicyclohexyl carbodiimide and 0.135 g of trifluoroacetic acid. After stirring the reaction solution at room temperature for 15 hours, a 6N hydrochloric acid solution was added thereto and the reaction solution was stirred for additional 30 minutes. The precipitates separated out were filtered off and washed with water. The filtrate and the wash liquid were combined, the mixture was alkalified with a saturated aqueous solution of sodium carbonate and then extracted with ethyl acetate. The resulting organic phase was washed with water, dried over anhydrous magnesium sulfate and then concentrated. The resulting residue was subjected to silica gel column chromatography and then eluted with chloroform/acetone (4/1) to thus give 0.23 g of (11aR)-10-[4-[(2-phenylbenzoyl)amino]benzoyl]-1,2,3,10,11,11a-hexahydro-5H-pyrrolo[2,1-c][1,4]benzodiazepin-2-one in the form of amorphous powder. The resulting amorphous powder (0.23 g) was dissolved in ethyl acetate and 0.12 ml of a 4N hydrochloric acid-ethyl acetate solution was added to the resulting solution at room temperature. After stirring the mixture at room temperature for one hour, the resulting precipitates separated out were recovered by filtration, followed by washing them with ethyl acetate and then dried to thus give 0.15 g (yield 34.2%) of the title compound.

m.p.: 180° C. (decomposition); $^1$H-N.M.R. (DMSO-$d_6$) δ: 2.80–3.00 (1 H, m), 3.50–4.90 (7 H, m), 5.15 (1 H, brs), 6.86 (1 H, d, J=7.8 Hz), 7.10–7.60 (16 H, m), 10.32 (1 H, s); I.R. (KBr) vcm$^{-1}$: 1780, 1655, 1640, 1600, 1520, 1410, 1320.

EXAMPLE 49

(3aS)-6-[4-[(2-Phenylbenzoyl) Amino]Benzoyl]-2,3, 3a,4,5,6-Hexahydro-1H-Pyrrolo[1,2-a][1,5] Benzodiazepine

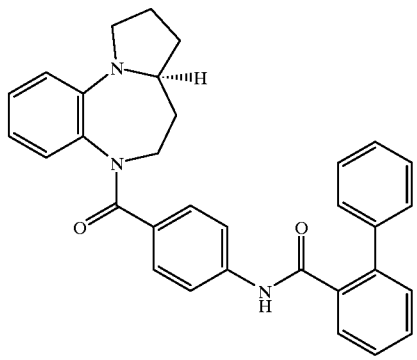

The same procedures used in Example 25 were repeated using (3aS)-2,3,3a,4,5,6-hexahydro-1H-pyrrolo[1,2-a][1,5]benzodiazepine prepared in Reference Example 62 and 4-[(2-phenylbenzoyl)amino]benzoic acid to give the title compound. Yield 37.5%.

m.p.: 215–216.5° C.; $^1$H-N.M.R. (CDCl$_3$) δ: 1.59–1.76 (2 H, m), 1.80–2.25 (4 H, m), 3.21–3.46 (3 H, m), 4.28 (1 H, brs), 4.72 (1 H, brs), 6.27–6.57 (3 H, m), 6.74–7.03 (6 H, m), 7.32–7.58 (8 H, m), 7.80–7.88 (1 H, m); I.R. (KBr) vcm$^{-1}$: 3280, 1645, 1600, 1520, 1500, 1405, 1320.

EXAMPLE 50

(2R,3aR)-2-Hydroxy-6-[4-[(2-Phenylbenzoyl Amino]Benzoyl]-2,3,3a,4,5,6-Hexahydro-1H-Pyrrolo[1,2-a][1,5]Benzodiazepine

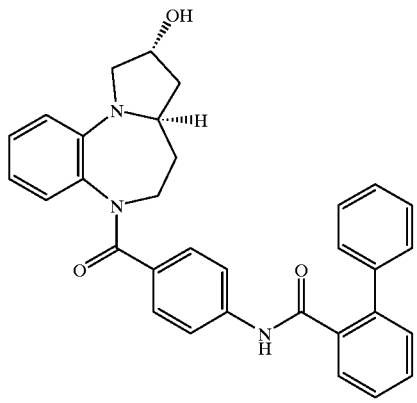

The same procedures used in Reference Example 64 were repeated using 1.85 g of (2R,4R)-2-[4-(tert-butyldimethylsilyloxy)-1-(2-nitrophenyl), pyrrolidin-2-yl] acetonitrile prepared in Reference Example 52 to give 1.08 g (yield 68.3%) of (2R,3aR)-4-(tert-butyldimethylsilyloxy)-2,3,3a,4,5,6-hexahydro-1H-pyrrolo[1,2-a][1,5]benzodiazepine. Then the same procedures used in Example 1 were repeated using 1.08 g of the resulting (2R,3aR)-4-(tert-butyldimethylsilyloxy)-2,3,3a,4,5,6-hexahydro-1H-pyrrolo [1,2-a][1,5]benzodiazepine and 1.44 g of 4-[(2-phenylbenzoyl)amino]benzoic acid to give 1.603 g (yield 76.1%) of (2R,3aR)-2-(tert-butyldimethylsilyloxy)-6-[4-[(2-phenylbenzoyl)amino]benzoyl]-2,3,3a,4,5,6-hexahydro-1H-pyrrolo[1,2-a][1,5]benzodiazepine. Further the same procedures used in Example 27 were repeated using the resulting (2R, 3aR)-2-(tert-butyldimethylsilyloxy)-6-[4-[(2-phenylbenzoyl)amino]benzoyl]-2,3,3a,4,5,6-hexahydro-1H-pyrrolo[1,2-a][1,5]benzodiazepine to give 1.146 g (yield 87.6%) of the title compound, m.p.: 185° C. (decomposition).

$^1$H-N.M.R. (DMSO-d$_6$) δ: 1.71–2.06 (3 H, m), 2.09–2.25 (2 H, m), 3.21–3.69 (4 H, m), 4.35–4.80 (1 H, m), 6.35–6.78 (3 H, m), 6.95–7.70 (14 H, m), 7.82 (1 H, d, J=7.3 Hz); I.R. (KBr) vcm$^{-1}$: 1660, 1600, 1520, 1400, 1320.

EXAMPLE 51

(3aR)-6-[4-[(2-Phenylbenzoyl) Amino]Benzoyl]-2,3,3a,4,5,6-Hexahydro-1H-Pyrrolo[1,2-a][1,5] Benzodiazepine

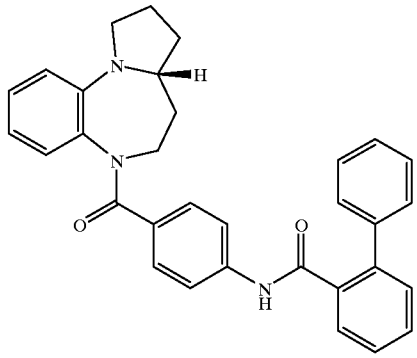

The same procedures used in Example 25 were repeated using (3aR)-2,3,3a,4,5,6-hexahydro-1H-pyrrolo[1,2-a][1,5] benzodiazepine obtained in, Reference Example 63 and 4-[(2-phenylbenzoyl)amino]benzoic acid to thus give the title compound. Yield 30.8%.

m.p.: 215–216.5° C. $^1$H-N.M.R. (CDCl$_3$) δ: 1.59–1.76 (2 H, m), 1.80–2.25 (4 H, m), 3.21–3.46 (3 H, m), 4.28 (1 H, brs), 4.72 (1 H, brs), 6.27–6.57 (3 H, m), 6.74–7.03 (6 H, m), 7.32–7.58 (8 H, m), 7.80–7.88 (1 H, m); I.R. (KBr) vcm$^{-1}$: 3280, 1645, 1600, 1520, 1500, 1405, 1320.

REFERENCE EXAMPLE 71

(2R,3aS)-2-(tert-Butyldimethylsilyloxy)-6-[4-[(2-Phenylbenzoyl) Amino]Benzoyl]-2,3,3a,4,5,6-Hexahydro-1 H-Pyrrolo[1,2-a][1,5]Benzpdiazepine

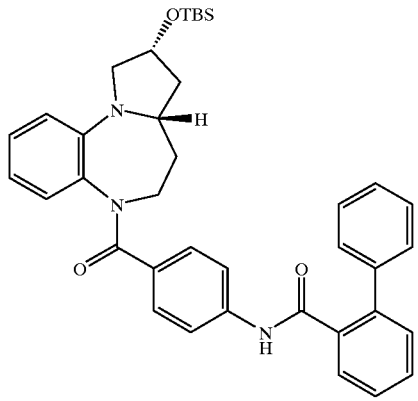

The same procedures used in Example 25 were repeated using (2R, 3aS)-2-(tert-butyldimethylsilyloxy)-2,3,3a,4,5,6-hexahydro-1H-pyrrolo[1,2-a][1,5]benzodiazepine obtained in Reference Example 64 and 4-[(2-phenylbenzoyl)amino] benzoic acid to thus give the title compound. Yield 87%.

$^1$H-N.M.R. (CDCl$_3$) δ: 0.12 (6 H, s), 0.85, 0.88, 0.92 (total9 H, each s), 1.65–1.80 (1 H, m), 2.10–2.60 (3 H, m), 3.20–3.30 (1 H, m), 3.35–355 (2 H, m), 4.30–4.80 (3 H, m), 6.30–6.70 (3 H, m), 6.80–7.60 (14 H, m), 7.80 (1 H, d, J=80 Hz); I.R. (KBr) vcm$^{-1}$: 3270, 1670, 1630, 1595, 1510, 1500, 1320.

EXAMPLE 52

(2R,3aS)-2-Hydroxy-6-[4-[(2-Phenylbenzoyl)
Amino]Benzoyl]-2,3,3a,4,5,6-Hexahydro-1H-
Pyrrolo[1,2-a][1,5]Benzodiazepine

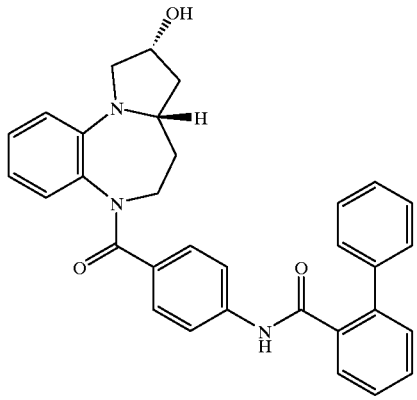

The same procedures used in Example 27 were repeated using (2R, 3aS)-2-(tert-butyldimethylsilyloxy)-6-[4-[(2-phenylbenzoyl)amino]benzoyl]-2,3,3a,4,5,6-hexahydro-1H-pyrrolo[1,2-a][1,5]benzodiazepine prepared in Reference Example 71 to thus give the title compound. Yield 87%.

m.p.: 208–209.5° C.; $^1$H-N.M.R. (CDCl$_3$) δ: 1.65–1.80 (1 H, m), 1.90–2.50 (3 H, m), 2.80–3.00 (1 H, m), 3.20–3.30 (1 H, m), 4.35–5.00 (4 H, m), 5.18 (1 H. brs), 6.35–6.80 (3 H, m), 6.95–7.70 (14 H, m), (10.20, 10.35) (total 1 H, each s); I.R. (KBr) νcm$^{-1}$: 3270, 1660, 1620, 1600, 1520, 1500, 1410, 1320.

EXAMPLE 53

(2S, 3aS)-2-Acetoxy-6-[4-[(2-Phenylbenzoyl)
Amino]Benzo]-2,3,3a,4,5,6-Hexahydro-1H-Pyrrolo
[1,2-a][1,5]Benzodiazepine

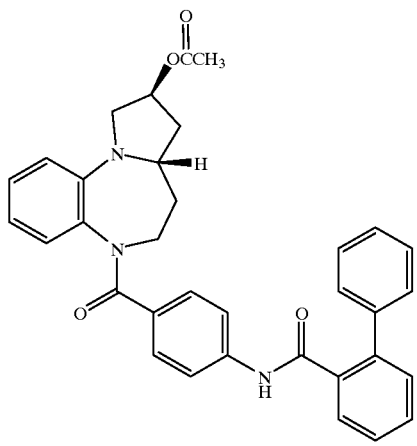

The same procedures used in Example 5 were repeated using (2R, 3aS)-2-hydroxy-6-[4-[(2-phenylbenzoyl)amino]benzoyl]-2,3,3a,4,5,6-hexahydro-1H-pyrrolo[1,2-a][1,5]benzodiazepine prepared in Example 52 to give the title compound as amorphous powder. Yield 91.7%.

$^1$H-N.M.R. (CDCl$_3$) δ: 1.80–2.35 (4 H, m), 2.10 (3 H, s), 3.35–3.50 (2 H, m), 3.55–3.65 (1 H, m), 4.45–4.60 (1 H, m), 4.70–4.85 (1 H, m), 5.45 (1 H, brs), 6.35–7.85 (18 H, m);

EXAMPLE 54

(2S, 3aS)-2-Hydroxy-6-[4-[(2-Phenylbenzoyl)
Amino]Benzoyl]-2,3,3a,4,5,6-Hexahydro-1H-
Pyrrolo[1,2-a][1,5]Benzodiazepine

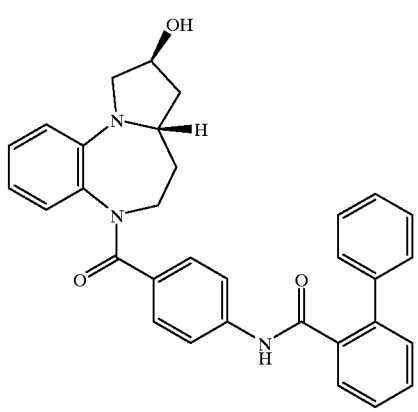

The same procedures used in Example 7 were repeated using (2S, 3aS)-2-acetoxy-6-[4-[(2-phenylbenzoyl)amino]benzoyl]-2,3,3a,4,5,6-hexahydro- 1H-pyrrolo[1,2-a][1,5]benzodiazepine prepared in Example 53 to give the title compound. Yield 65.0%.

m.p.: 198–199.5° C.; $^1$H-N.M.R. (DMSO-d$_6$) δ: 1.70–2.30 (4 H, m), 3.10–3.30 (1 H, m), 3.45–3.60 (1 H, m), 4.40–5.20 (4 H, m), 6.35–6.80 (4 H, m), 6.90–7.70 (12 H, m), (10.00, 10.35) (total 1 H, eash s); I.R. (KBr) νcm$^{-1}$: 1660, 1620, 1600, 1520, 1500, 1410, 1320.

EXAMPLE 55

(2S, 3aR)-2-Amino-6-[4-[(2-Phenylbenzoyl)
Amino]Benzoyl]-2,3,3a,4,5,6-Hexahydro-1H-
Pyrrolo[1,2-a][1,5]Benzodiazepine

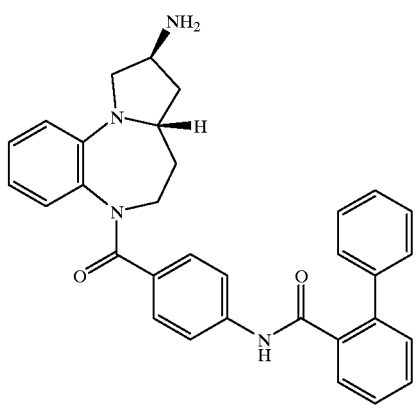

The same procedures used in Reference Example 65 were repeated using (2R,3aS)-6-[4-[(2-phenylbenzoyl)amino] benzoyl]-2-phthalimido-2,3,3a,4,5,6-hexahydro-1H-pyrrolo [1,2-a][1,5]benzodiazepine prepared in Example 52 to give (2S, 3aS)-6-[4-[(2-phenylbenzoyl)amino]benzoyl]-2-phthalimido-2,3,3a,4,5,6-hexahydro-1H-pyrrolo[1,2-a][1,5] benzodiazepine (yield 99.8%). Then the same procedures used in Example 9 were repeated using the resulting (2S, 3aS)-6-[4-[(2-phenylbenzoyl)amino]benzoyl]-2-phthalimido-2,3,3a,4,5,6-hexahydro-1H-pyrrolo[1,2-a][1,5]

benzodiazepine to thus give the title compound as amorphous powder. Yield 61%.

$^1$H-N.M.R. (CDCl$_3$) δ: 1.80–2.30, 2.50–2.70 (total 4 H, each m), 3.00–3.25 (1 H, m), 3.35–3.60 (2 H, m), (4.45–4.60, 4.70–4.85, 5.00–5.15 (total 2 H, each m), 6.30–6.65 (2 H, m), 6.80–7.15 (4 H, m), 7.35–7.60 (11 H, m), 7.85 (1 H, d, J=7.8 Hz).

EXAMPLE 56

(2S, 3aR)-2-(N,N-dimethylamino)-6-[4-[(2-phenylbenzoyl) amino]benzoyl]-2,3,3a,4,5,6-hexahydro-1H-Pyrrolo[1,2-a][1,5]benzodiazepine hydrochloride

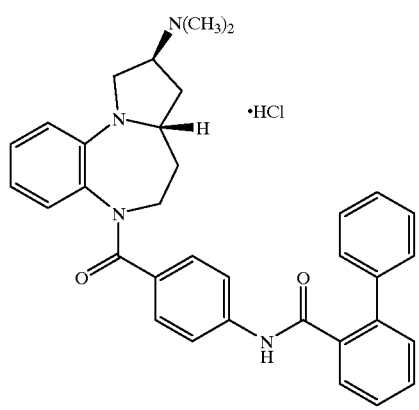

The same procedures used in Example 10 were repeated using (2S, 3aR)-2-amino-6-[4-[(2-phenylbenzoyl)amino]benzoyl]-2,3,3a,4,5,6-hexahydro-1H-pyrrolo[1,2-a][1,5]benzodiazepine prepared in Example 55 to thus give the title compound. Yield 65.4%.

m.p.: 223–225° C.; $^1$H-N.M.R. (DMSO-d$_6$) δ: 1.62–1.90 (1 H, m), 2.04–2.23 (1 H, m), 2.40–2.68 (1 H, m), 2.88 (3 H, s), 2.89 (3 H, s), 3.02–3.20 (1 H, m), 3.22–3.78 (3 H, m), 3.87–4.16 (1 H, m), 4.38–4.70 (1 H, m), 4.77–4.93 (1 H, m), 6.42 (1 H, brs), 6.62–6.70 (2 H, m), 6.90 (2 H, d, J=8.4 Hz), 7.16–7.61 (12 H, m), 10.25 (H, brs), 10.91 (1 H, brs); I.R. (KBr) vcm$^{-1}$: 3400, 1630, 1520, 1500, 1405, 1320.

DRUG PREPATATION EXAMPLE 1

Injection

TABLE 5

| Composition | |
|---|---|
| Compound of Example 43 | 1.0 mg |
| Citric Acid | 0.2 mg |
| Sodium Citrate | 0.4 mg |
| Sodium Chloride | 18.0 mg |
| Water for Injection | ad. 2.0 ml |

To a solution of citric acid (0.1 g) in water for injection (400 ml), there were added 0.5 g of (11aR)-10[4-[(2-phenylbenzoyl)amino]benzoyl]-1,2, 3,10,11,11a-hexahydro-5H-pyrrolo[2,1-c][1,4]benzodiazepine hydrochloride prepared in Example 43, 0.2 g of sodium citrate and 9 g of sodium chloride. The mixture was stirred at 60° C. to give a solution. After cooling the solution to room temperature, the total volume thereof was adjusted to 1000 ml. The solution was filtered through a membrane filter (pore size: 0.22 μm), it was dispensed in ampuls (2 ml each), followed by sterilization by heating to thus prepare injections.

DRUG PREPATATION EXAMPLE 2

Tablet

TABLE 6

| | Composition | |
|---|---|---|
| [Tablet] | Compound of Example 56 | 5.0 mg |
| | Lactose | 71.5 mg |
| | Corn Starch | 20.0 mg |
| | Hydroxypropyl Cellulose | 3.0 mg |
| | Magnesium Stearate | 0.5 mg |
| | Subtotal | 100 mg |
| [Coating] | Hydroxypropylmethyl Cellulose 2910 | 4.0 mg |
| | Polyethylene Glycol 6000 | 0.5 mg |
| | Titanium Oxide | 0.5 mg |
| | Subtotal | 5 mg |
| | Total | 105 mg |

(2S, 3aS)-2-(N,N,-Dimethylamino)-6-[4-[(2-phenylbenzoyl)amino]benzoyl]-2,3,3a,4,5,6-hexahydro-1H-pyrrolo[1,2-a][1,5]benzodiazepine hydrochloride (25 g) prepared in Example 56 was mixed with lactose (357.5 g) and then the mixture was pulverized in Bantam Mill (available from Tokyo Atomizer Co., Ltd.). The pulverized product was uniformly mixed with 100 g of corn starch in a fluidized granulation-coating device (available from Oogawara Mfg. Co., Ltd.) and then the mixture was sprayed with 150 g of a 10% hydroxypropyl cellulose aqueous solution to thus form granules. After drying the granules, they were passed through a 24 mesh sieve, followed by addition of 2.5 g of magnesium stearate and formation of tablets (100 mg each) using 6.5 mm φ×5R mortar and pestle in Rotary Tablet Machine (available from kikusui Mfg. Co., Ltd.). The tablets thus prepared were sprayed with 300 g of an aqueous coating liquid containing 20 g of hydroxypropylmethyl cellulose 2910, 2.5 g of polyethylene glycol 6000 and 2.5 g of titanium oxide using a coating device (Freund Sangyo Co., Ltd.) so that the coated amount was equal to 5 mg per tablet to thus form film coated tablets.

DRUG PREPATATION EXAMPLE 3

Capsule

TABLE 7

| Composition | |
|---|---|
| Compound of Example 25 | 5.0 mg |
| Crystalline Cellulose | 195.0 mg |
| Lactose | 58.0 mg |
| Hydroxypropyl Cellulose of Low Degree Of Substitution | 25.0 mg |
| Polyvinyl Pyrrolidone | 15.0 mg |
| Magnesium Stearate | 2.0 mg |
| Total | 300 mg |

(11aS)-10-[4-[(2-Phenylbenzoyl)amino]benzoyl]-1,2,3,10,11,11a-hexahydro-5H-pyrrolo[2,1-c][1,4]benzodiazepin-5-one prepared in Example 25 was pulverized into powder, then there were added, to 10 g of the powder, 390 g of crystalline cellulose, 116 g of lactose 50 g of hydroxypropyl cellulose having a low degree of substitution and 30 g of polyvinyl pyrrolidone, followed by addition of 120 ml of ethanol, uniform mixing thereof and pulverization. The resulting mixture was dried at 50° C. for 12 to 16 hours, passed through a 25 mesh sieve, followed by addition of 4 g of magnesium stearate, uniform mixing of the mixture and charging of 300 mg each of the mixed powder in No.1 capsule to thus give hard capsules (content of effective component: 5 mg/capsule).

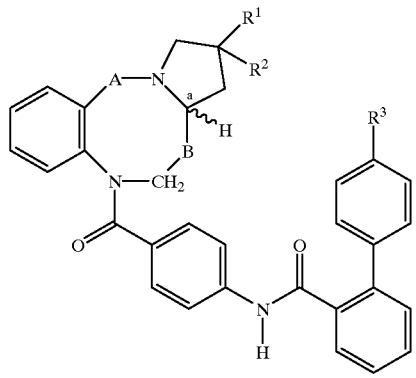

(1)

The compounds synthesized in Examples 1 to 56 are summarized in the following Table 9.

TABLE 9

| Example No. | A | B | a ⁓H | $R^1$ | $R^2$ | $R^3$ | Form |
|---|---|---|---|---|---|---|---|
| 1 | Single bond | Single bond | ....ıııH | H | H | H | Free |
| 2 | " | " | " | " | " | $CH_3$ | " |
| 3 | " | " | " | ....ıııOH | " | H | " |
| 4 | " | " | " | " | " | $CH_3$ | " |
| 5 | " | " | " | ◂$OCCH_3$ (O double bond) | " | H | " |
| 6 | " | " | " | " | " | $CH_3$ | " |
| 7 | " | " | " | ◂OH | " | H | " |
| 8 | " | " | " | " | " | $CH_3$ | " |
| 9 | " | " | " | ◂$NH_2$ | " | H | " |
| 10 | " | " | " | ◂$N(CH_3)_2$ | " | " | HCl salt |
| 11 | " | " | ◂H | H | " | " | Free |
| 12 | " | " | " | " | " | $CH_3$ | " |
| 13 | " | " | " | ....ıııOH | " | H | " |
| 14 | " | " | " | " | " | $CH_3$ | " |
| 15 | " | " | " | ◂$OCCH_3$ (O double bond) | " | H | " |
| 16 | " | " | " | " | " | $CH_3$ | " |
| 17 | " | " | " | ◂OH | " | H | " |
| 18 | " | " | " | " | " | $CH_3$ | " |
| 19 | " | " | " | ◂$NH_2$ | " | H | " |
| 20 | " | " | " | " | " | $CH_3$ | " |

TABLE 9-continued
| Example No. | A | B | a ⌇H | R¹ | R² | R³ | Form |
|---|---|---|---|---|---|---|---|
| 21 | " | " | " | ◀N(CH₃)₂ | " | H | HCl salt |
| 22 | " | " | " | " | " | CH₃ | " |
| 23 | " | " | " | ◀F | " | H | Free |
| 24 | " | " | " | =O | | CH₃ | " |
| 25 |  | " | ⋯⋯H | H | " | H | " |
| 26 | " | " | " | " | " | CH₃ | " |
| 27 | " | " | " | ⋯⋯OH | " | H | " |
| 28 | " | " | " |  | " | " | " |
| 29 | " | " | " | ◀OH | " | " | " |
| 30 | " | " | " | =O | " | " | " |
| 31 | " | " | ◀H | H | " | " | " |
| 32 | " | " | " | ⋯⋯OH | " | " | " |
| 33 | " | " | " |  | " | " | " |
| 34 | " | " | " | ◀OH | " | " | " |
| 35 | " | " | " | ◀NH₂ | " | " | " |
| 36 | " | " | " | ◀N(CH₃)₂ | " | " | HCl salt |
| 37 |  | " | ⋯⋯H | H | " | " | Free |
| 38 | " | " | " | " | " | CH₃ | " |
| 39 | " | " | ◀H | " | " | H | " |

TABLE 9-continued

| Example No. | A | B | a ⁀H | R¹ | R² | R³ | Form |
|---|---|---|---|---|---|---|---|
| 40 | O=S(=O) | " | ......H | " | " | " | " |
| 41 | —CH₂— | " | " | " | " | " | HCl salt |
| 42 | " | " | " | ......OH | " | " | " |
| 43 | " | " | ◂H | H | " | " | " |
| 44 | " | " | " | " | " | CH₃ | " |
| 45 | " | " | " | ......OH | " | H | " |
| 46 | " | " | " | ◂OC(=O)CH₃ | " | " | Free |
| 47 | " | " | " | ◂OH | " | " | HCl salt |
| 48 | " | " | " | =O | " | " | " |
| 49 | Single bond | —CH₂— | ......H | H | " | " | Free |
| 50 | " | " | " | ......OH | " | " | " |
| 51 | " | " | ◂H | H | " | " | " |
| 52 | " | " | " | ......OH | " | " | " |
| 53 | " | " | " | ◂OC(=O)CH₃ | " | " | " |
| 54 | " | " | " | ◂OH | " | " | " |
| 55 | " | " | " | ◂NH₂ | " | " | " |
| 56 | " | " | " | ◂N(CH₃)₂ | " | " | HCl salt |

INDUSTRIAL APPLICABILITY

The compounds of the present invention have novel chemical structures described above and thus novel compounds, which have not yet been described in any literature. In addition, the drug composition comprising the compound of the present invention as an effective component possesses reliable and excellent water diurese. Therefore, the compounds of the present invention would be expected as diuretics, or vasopressin receptor antagonists, or remedies or prophylactics for brain edema, pneumochysis, arginine-vasopressin polyrrhea syndromes, renal failure, pancreatitis, conjestive heart failure or hepatocirrhosis, and may be practically used in other medical fields.

What is claimed is:
1. A biphenyl compound represented by the following formula (I)

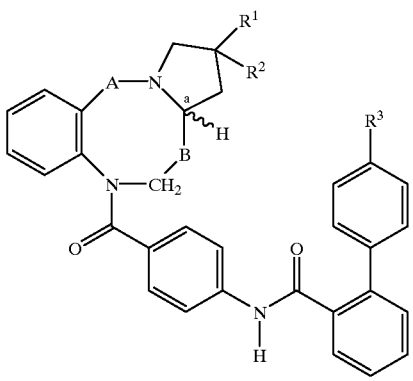

wherein

A represents a single bond, —CH$_2$—, —CO—, —CS—, or —SO$_2$—;

B represents a single bond or —CH$_2$—;

R$^1$ represents a hydrogen atom, —OH, —NR$^{11}$R$^{12}$, wherein R$^{11}$ and R$^{12}$ each, independently, represents a hydrogen atom or an alkyl group having 1 to 4 carbon atoms, —OCOCH$_3$, or a halogen atom;

R$^2$ represents a hydrogen atom, or

R$^1$ and R$^2$, together, form a =O group;

R$^3$ represents a hydrogen atom or an alkyl group having 1 to 4 carbon atoms, provided that in the formula, the absolute configuration of the position a may be either R or S, or a pharmaceutically acceptable salt thereof.

2. A biphenyl compound or a pharmaceutically acceptable salt thereof as set forth in claim 1 wherein A represents a single bond, —CH$_2$— or —CO—; B is a single bond; R$^1$ is a hydrogen atom or —OH; R$^2$ is a hydrogen atom or R$^1$ and R$^2$ form a group =O together; and R$^3$ represents a hydrogen atom or an alkyl group having 1 to 4 carbon atoms.

3. A biphenyl compound or a pharmaceutically acceptable salt thereof as set forth in claim 1 wherein it is selected from the group consisting of (2, S, 3aR)-2-hydroxy-5-[4-[[2-(4-tolyl)benzoyl]amino]benzoyl]-1,2,3,3a,4,5-hexahydro-pyrrolo[1,2-a]quinoxaline; (11aS)-10-[4-[(2-phenylbenzoyl) amino]benzoyl]-1,2,3,10,11,11a-hexahydro-5H-pyrrolo[2,1-c][1,4]benzodiazepin-5-one; (11aS)-10-[4-[(2-phenylbenzoyl)amino]benzoyl]-1,2,3,10, 11,11a-hexahydro-5H-pyrrolo[2,1-c][1,4]benzodiazepin-2, 5-dione; and (2S, 11aR)-2-hydroxy-10-[4-[(2-phenylbenzoyl)amino]benzoyl]-1,2,3,10,11,11a-hexahydro-5H-pyrrolo[2,1-c][1,4]benzodiazepine.

4. A drug composition comprising a biphenyl compound or a pharmaceutically acceptable salt thereof as set forth in claim 1 and a pharmaceutically acceptable carrier.

5. A drug composition comprising a biphenyl compound or a pharmaceutically acceptable salt thereof as set forth in claim 2 and a pharmaceutically acceptable carrier.

6. A drug composition comprising a biphenyl compound or a pharmaceutically acceptable salt thereof as set forth in claim 3 and a pharmaceutically acceptable carrier.

7. A method of treating brain edema, pneumochysis, arginine-vasopressin polyrrhea syndromes, renal failure, pancreatitis, congestive heart failure or hepatocirrhosis, comprising administering to a patient in need thereof an effective amount of the biphenyl compound or a pharmaceutically acceptable salt thereof as set forth in claim 1.

8. A method of treating brain edema, pneumochysis, arginine-vasopressin polyrrhea syndromes, renal failure, pancreatitis, congestive heart failure or hepatocirrhosis, comprising administering to a patient in need thereof an effective amount of the biphenyl compound or a pharmaceutically acceptable salt thereof as set forth in claim 2.

9. A method of treating brain edema, pneumochysis, arginine-vasopressin polyrrhea syndromes, renal failure, pancreatitis, congestive heart failure or hepatocirrhosis, comprising administering to a patient in need thereof an effective amount of the biphenyl compound or a pharmaceutically acceptable salt thereof as set forth in claim 3.

* * * * *